United States Patent
Butler et al.

(10) Patent No.: US 10,023,600 B2
(45) Date of Patent: Jul. 17, 2018

(54) PROCESSES AND INTERMEDIATES FOR THE PREPARATION OF 1'-SUBSTITUTED CARBA-NUCLEOSIDE ANALOGS

(75) Inventors: Thomas Butler, Redwood City, CA (US); Aesop Cho, Mountain View, CA (US); Benjamin R. Graetz, San Mateo, CA (US); Choung U. Kim, San Carlos, CA (US); Samuel E. Metobo, Newark, CA (US); Oliver L. Saunders, San Mateo, CA (US); Andrew W. Waltman, San Francisco, CA (US); Jie Xu, Foster City, CA (US); Lijun Zhang, Los Altos Hills, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 961 days.

(21) Appl. No.: 12/886,248

(22) Filed: Sep. 20, 2010

(65) Prior Publication Data

US 2011/0230654 A1 Sep. 22, 2011

Related U.S. Application Data

(60) Provisional application No. 61/244,299, filed on Sep. 21, 2009.

(51) Int. Cl.
*C07H 19/23* (2006.01)
*C07H 1/00* (2006.01)
*A61K 31/7052* (2006.01)
*A61K 31/7056* (2006.01)
*A61K 31/706* (2006.01)

(52) U.S. Cl.
CPC .............. *C07H 1/00* (2013.01); *C07H 19/23* (2013.01); *A61K 31/706* (2013.01); *A61K 31/7052* (2013.01); *A61K 31/7056* (2013.01)

(58) Field of Classification Search
CPC ................ C07H 19/23; A61K 31/7052; A61K 31/7056; A61K 31/706
See application file for complete search history.

(56) References Cited

U.S. PATENT DOCUMENTS

| | | | |
|---|---|---|---|
| 7,973,013 B2 * | 7/2011 | Cho et al. | 514/23 |
| 8,008,264 B2 * | 8/2011 | Butler et al. | 514/23 |
| 2010/0021425 A1 * | 1/2010 | Butler et al. | 424/85.4 |
| 2010/0203015 A1 * | 8/2010 | Butler et al. | 424/85.4 |
| 2011/0070194 A1 * | 3/2011 | Cho et al. | 424/85.4 |
| 2011/0293563 A1 * | 12/2011 | Butler et al. | 424/85.4 |

FOREIGN PATENT DOCUMENTS

| | | |
|---|---|---|
| WO | WO-2000/56734 A1 | 9/2000 |
| WO | WO-2006/031725 A2 | 3/2006 |
| WO | WO-2007-056170 A2 | 5/2007 |
| WO | WO-2007/064883 A2 | 6/2007 |
| WO | WO-2007/064931 A2 | 6/2007 |
| WO | WO-2008089105 A2 | 7/2008 |
| WO | WO-2008116064 A2 | 9/2008 |
| WO | WO 2008/141079 A1 * | 11/2008 ........... C07D 519/00 |
| WO | WO-2008/141079 A1 | 11/2008 |
| WO | WO-2009/131926 A1 | 10/2009 |
| WO | WO-2009/132123 A1 | 10/2009 |
| WO | WO-2009/132135 A1 | 10/2009 |
| WO | WO-2010/002877 A2 | 1/2010 |
| WO | WO-2010/036407 A2 | 4/2010 |

OTHER PUBLICATIONS

Hoffman, M., Rychlewski, J. (2002) When, in the Context of Drug Design, Can a Fluorine Atom Successfully Substitute a Hydroxyl Group? International Journal of Quantum Chemistry, vol. 89, p. 419-427.*
Greene, T.W. and Wuts, P.G.M. (1991) Protective Groups in Organic Synthesis, published by John Wiley & Sons, Inc., p. 1-4, 10-14, 47-53 and 100-103.*
Greene, T.W. and Wuts, P.G.M. (1991) Protective Groups in Organic Synthesis, published by John Wiley & Sons, Inc., p. 118-142.*
Bojack, G. et al. (2001) "Design and Synthesis of Inhibitors of Adenosine and AMP Deaminases," *Organic Letters* 3(6):839-842.
Dudfield, P. et al. (1999) "Synthesis of C-ribosyl imidazo[2,1-f][1,2,4]triazines as inhibitors of adenosine and AMP deaminases," *J. Chem. Soc, Perkin Trans I* 2929-2936.
Haraguchi, K. et al. (1995) "Stereoselective Synthesis of 1'-C-Branched Uracil Nucleosides From Uridine," *Nucleosides & Nucleotides* 14(3-5):417-420.
Hayashi, M. et al. (1992) "C-Nucleosides, A Synthesis of 2-Substituted 7-(β-D-Ribofuranosyl)-Pyrrolo[2,1-f]-1,2,4-Triazines. A New Type of "Purine Like" C-Nucleoside," *Heterocycles* 34(3):569-574.
International Search Report for PCT/US2010/049508, filed Sep. 20, 2010, dated Nov. 5, 2010.
Itoh, Y. et al. (1995) "Divergent and Stereocontrolled Approach to the Synthesis of Uracil Nucleosides Branched at the Anomeric Position," *J. Org. Chem,.* 60:656-662.

(Continued)

*Primary Examiner* — Leigh C Maier
(74) *Attorney, Agent, or Firm* — Mintz, Levin, Cohn, Ferris, Glovsky and Popeo, P.C.

(57) ABSTRACT

Provided are processes and intermediates for the syntheses of nucleosides of pyrrolo[1,2-f][1,2,4]triazinyl and imidazo [1,2-f][1,2,4]triazinyl heterocycles of Formula I.

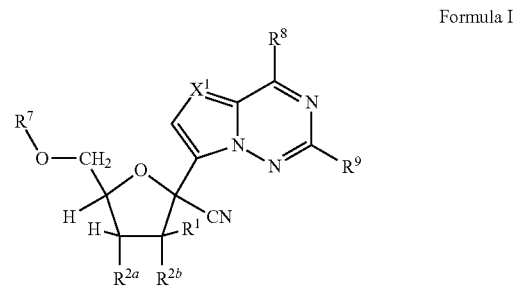

Formula I

2 Claims, No Drawings

(56) References Cited

OTHER PUBLICATIONS

Knutsen, L. et al. (1984) "Synthesis of Imidazo-fused Bridgehead-nitrogen C-Nucleosides via Dehydrative Coupling Reactions of 2,5-Anhydro-3,4,6-tri-O-benzoyl-D-allonic Acid," *J. Chem. Soc. Perkin Trans I* pp. 229-238.
Knutsen, L. et al. (1985) "Synthesis of Imidazo-fused Bridgehead-nitrogen C-Nucleosides : Coupling-Elimination Reactions of 2,5-Anhydro-3,4,6-tri-O-benzoyl-D-allonic Acid," *J. Chem. Soc. Perkin Trans I* pp. 621-630.
Nishimura, N. (2001) "Synthesis of pyrrolo[2,1-f][1,2,4]triazine C-nucleosides. Isosteres of sangivamycin, tubercidin, and toyocamycin," *Carbohydrate Research* 331:77-82.
Otter, B. et al. (1996) "Conformational Properties of Purine-Like C-Nucleosides," *Nucleosides & Nucleotides* 15(1-3):793-807.
Patil, S. et al. (1994) "4-Aza-7,9-Dideazaadenosine, a New Cytotoxic Synthetic C-Nucleoside Analogue of Adenosine," *Tetrahedron Letters* 35(30):5339-5342.
Written Opinion for PCT/US2010/049508, filed Sep. 20, 2010, dated Nov. 5, 2010.
Yoshimura, Y. et al. (1996) "Synthesis and Biological Evaluation of 1'-C-Cyano-Pyrimidine Nucleosides," *Nucleosides & Nucleotides* 15(1-3):305-324.

\* cited by examiner

PROCESSES AND INTERMEDIATES FOR THE PREPARATION OF 1'-SUBSTITUTED CARBA-NUCLEOSIDE ANALOGS

This application is filed under 35 U.S.C. 111(a) claiming the benefit under 35 U.S.C. 119(e) of U.S. provisional application 61/244,299 filed Sep. 21, 2009 which is herein incorporated by reference in its entirety for all purposes.

FIELD OF THE INVENTION

The invention relates generally to methods and intermediates for preparing compounds with antiviral activity, more particularly methods and intermediates for preparing nucleosides active against Flaviviridae infections.

BACKGROUND OF THE INVENTION

Viruses comprising the Flaviviridae family comprise at least three distinguishable genera including *pestiviruses, flavivir uses,* and *hepaeiviruses* (Calisher, et al., J. Gen. Virol., 1993, 70, 37-43). While pestiviruses cause many economically important animal diseases such as bovine viral diarrhea virus (BVDV), classical swine fever virus (CSFV, hog cholera) and border disease of sheep (BDV), their importance in human disease is less well characterized (Moennig, V., et al., Adv. Vir. Res. 1992, 48, 53-98). *Flaviviruses* are responsible for important human diseases such as dengue fever and yellow fever while hepaciviruses cause hepatitis C virus infections in humans. Other important viral infections caused by the Flaviviridae family include West Nile virus (WNV) Japanese encephalitis virus (JEV), tick-borne encephalitis virus, Junjin virus, Murray Valley encephalitis, St Louis enchaplitis, Omsk hemorrhagic fever virus and Zika virus. Combined, infections from the Flaviviridae virus family cause significant mortality, morbidity and economic losses throughout the world. Therefore, there is a need to develop effective treatments for Flaviviridae virus infections.

The hepatitis C virus (HCV) is the leading cause of chronic liver disease worldwide (Boyer, N. et al. J Hepatol. 32:98-112, 2000) so a significant focus of current antiviral research is directed toward the development of improved methods of treatment of chronic HCV infections in humans (Di Besceglie, A. M. and Bacon, B. R., Scientific American, October: 80-85, (1999); Gordon, C. P., et al., J. Med. Chem. 2005, 48, 1-20; Maradpour, D.; et al., Nat. Rev. Micro. 2007, 5(6), 453-463). A number of HCV treatments are reviewed by Bymock et al. in Antiviral Chemistry & Chemotherapy, 11:2; 79-95 (2000).

RNA-dependent RNA polymerase (RdRp) is one of the best studied targets for the development of novel HCV therapeutic agents. The NS5B polymerase is a target for inhibitors in early human clinical trials (Sommadossi, J., WO 01/90121 A2, US 2004/0006002 A1). These enzymes have been extensively characterized at the biochemical and structural level, with screening assays for identifying selective inhibitors (De Clercq, E. (2001) J. Pharmacol. Exp. Ther. 297:1-10; De Clercq, E. (2001) J. Clin. Viral. 22:73-89). Biochemical targets such as NS5B are important in developing HCV therapies since HCV does not replicate in the laboratory and there are difficulties in developing cell-based assays and preclinical animal systems.

Currently, there are primarily two antiviral compounds, ribavirin, a nucleoside analog, and interferon-alpha (α) (IFN), which are used for the treatment of chronic HCV infections in humans. Ribavirin alone is not effective in reducing viral RNA levels, has significant toxicity, and is known to induce anemia. The combination of IFN and ribavirin has been reported to be effective in the management of chronic hepatitis C (Scott, L. J., et al. *Drugs* 2002, 62, 507-556) but less than half the patients given this treatment show a persistent benefit. Other patent applications disclosing the use of nucleoside analogs to treat hepatitis C virus include WO 01/32153, WO 01/60315, WO 02/057425, WO 02/057287, WO 02/032920, WO 02/18404, WO 04/046331, WO2008/089105 and WO2008/141079 but additional treatments for HCV infections have not yet become available for patients. Therefore, drugs having improved antiviral and pharmacokinetic properties with enhanced activity against development of HCV resistance, improved oral bioavailability, greater efficacy, fewer undesirable side effects and extended effective half-life in vivo (De Francesco, R. et al. (2003) Antiviral Research 58:1-16) are urgently needed.

Certain ribosides of the nucleobases pyrrolo[1,2-f][1,2,4]triazine, imidazo[1,5-f][1,2,4]triazine, imidazo[1,2-f][1,2,4]triazine, and [1,2,4]triazolo[4,3-f][1,2,4]triazine have been disclosed in *Carbohydrate Research* 2001, 331(1), 77-82; *Nucleosides & Nucleotides* (1996), 15(1-3), 793-807; *Tetrahedron Letters* (1994), 35(30), 5339-42; *Heterocycles* (1992), 34(3), 569-74; *J. Chem. Soc. Perkin. Trans.* 1 1985, 3, 621-30; *J. Chem. Soc. Perkin Trans.* 1 1984, 2, 229-38; WO 2000056734; *Organic Letters* (2001), 3(6), 839-842; *J. Chem. Soc. Perkin Trans.* 1 1999, 20, 2929-2936; and *J. Med. Chem.* 1986, 29(11), 2231-5. However, these compounds have not been disclosed as useful for the treatment of HCV.

Ribosides of pyrrolo[1,2-f][1,2,4]triazinyl, imidazo[1,5-f][1,2,4]triazinyl, imidazo[1,2-f][1,2,4]triazinyl, and [1,2,4]triazolo[4,3-f][1,2,4]triazinyl nucleobases with antiviral, anti-HCV, and anti-RdRp activity have been disclosed by Babu, Y. S., WO2008/089105 and WO2008/141079; Cho, et al., WO2009/132123 and Francorn, et al. WO2010/002877.

Butler, et al., WO2009/132135, has disclosed anti-viral pyrrolo[1,2-f][1,2,4]triazinyl, imidazo[1,5-f][1,2,4]triazinyl, imidazo[1,2-f][1,2,4]triazinyl, and [1,2,4]triazolo[4,3-f][1,2,4]triazinyl nucleosides wherein the 1' position of the nucleoside sugar is substituted with a cyano group. However, the methods described for introducing the 1' cyano group only produced about a 3:1 ratio of β to α anomers and, in certain circumstances, the cyanation reactions was particularly slow. Therefore, there is a need to develop more efficient processes and intermediates for the syntheses of nucleosides of pyrrolo[1,2-f][1,2,4]triazinyl and imidazo[1,2-f][1,2,4]triazinyl heterocycles.

SUMMARY OF THE INVENTION

Provided are processes and intermediates for the syntheses of nucleosides of pyrrolo[1,2-f][1,2,4]triazinyl and imidazo[1,2-f][1,2,4]triazinyl heterocycles.

Provided are methods for preparing a compound of Formula I:

Formula I

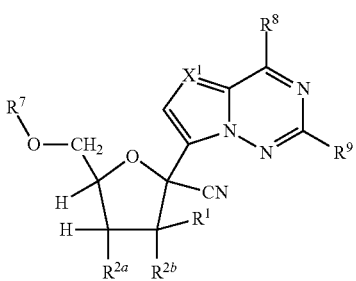

or an acceptable salt, thereof;
wherein:
$R^1$ is H, $(C_1$-$C_8)$alkyl, $(C_4$-$C_8)$carbocyclylalkyl, $(C_1$-$C_8)$ substituted alkyl, $(C_2$-$C_8)$alkenyl, $(C_2$-$C_8)$substituted alkenyl, $(C_2$-$C_8)$alkynyl, $(C_2$-$C_8)$substituted alkynyl, or aryl $(C_1$-$C_8)$alkyl;

each $R^{2a}$ or $R^{2b}$ is independently H, F or $OR^4$;

each $R^3$ is independently $(C_1$-$C_8)$alkyl, $(C_1$-$C_8)$ substituted alkyl, $C_6$-$C_{20}$ aryl, $C_6$-$C_{20}$ substituted aryl, $C_2$-$C_{20}$ heterocyclyl, $C_2$-$C_{20}$ substituted heterocyclyl, $C_7$-$C_{20}$ arylalkyl, $C_7$-$C_{20}$ substituted arylalkyl, $(C_1$-$C_8)$alkoxy, or $(C_1$-$C_8)$ substituted alkoxy;

each $R^4$ or $R^7$ is independently H, optionally substituted allyl, $-C(R^5)_2R^6$, $Si(R^3)_3$, $C(O)R^5$, $-C(O)OR^5$, $-C(R^5)_2)_m-R^{15}$ or

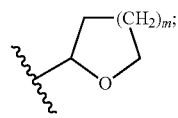

or any two of $R^4$ or $R^7$ when taken together are $-C(R^{19})_2-$, $-C(O)-$ or $-Si(R^3)_2(X^2)_mSi(R^3)_2-$;

each $R^{15}$ is independently $-O-C(R^5)_2R^6$, $-Si(R^3)_3$, $C(O)OR^5$, $-OC(O)R^5$ or

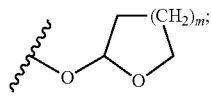

each $R^5$, $R^{18}$ or $R^{19}$ is independently H, $(C_1$-$C_8)$alkyl, $(C_1$-$C_8)$ substituted alkyl, $(C_2$-$C_8)$alkenyl, $(C_2$-$C_8)$ substituted alkenyl, $(C_2$-$C_8)$alkynyl, $(C_2$-$C_8)$ substituted alkynyl, $C_6$-$C_{20}$ aryl, $C_6$-$C_{20}$ substituted aryl, $C_2$-$C_{10}$ heterocyclyl, $C_2$-$C_{20}$ substituted heterocyclyl, $C_7$-$C_{20}$ arylalkyl or $C_7$-$C_{20}$ substituted arylalkyl;

each $R^6$ is independently $C_6$-$C_{20}$ aryl, $C_6$-$C_{20}$ substituted aryl, or optionally substituted heteroaryl;

each $R^a$ is independently H, $(C_1$-$C_8)$alkyl, $(C_2$-$C_8)$alkenyl, $(C_2$-$C_8)$alkynyl, aryl$(C_1$-$C_8)$alkyl, $(C_4$-$C_8)$carbocyclylalkyl, $-C(=O)R^{11}$, $-C(=O)OR^{11}$, $-C(=O)NR^{11}R^{12}$, $-C(=O)SR^{11}$, $-S(O)R^{11}$, $-S(O)_2R^{11}$, $-S(O)(OR^{11})$, $-S(O)_2(OR^{11})$, or $-SO_2NR^{11}R^{12}$;

$X^1$ is C—$R^{10}$ or N;
each $X^2$ is O or $CH_2$;
each m is 1 or 2;
each n is independently 0, 1 or 2;
each $R^8$ is halogen, $NR^{11}R^{12}$, $N(R^{11})OR^{11}$, $NR^{11}NR^{11}R^{12}$, $N_3$, NO, $NO_2$, CHO, $CH(=NR^{11})$, $-CH=NHNR^{11}$, $-CH=N(OR^{11})$, $-CH(OR^{11})_2$, $-C(=O)NR^{11}R^{12}$, $-C(=S)NR^{11}R^{12}$, $-C(=O)OR^{11}$, $(C_1$-$C_8)$alkyl, $(C_2$-$C_8)$alkenyl, $(C_2$-$C_8)$alkynyl, $(C_4$-$C_8)$carbocyclylalkyl, optionally substituted aryl, optionally substituted heteroaryl, $-C(=O)(C_1$-$C_8)$alkyl, $-S(O)_n(C_1$-$C_8)$alkyl, aryl$(C_1$-$C_8)$alkyl, CN, $OR^{11}$ or $SR^{11}$;

each $R^9$ or $R^{10}$ is independently H, halogen, $NR^{11}R^{12}$, $N(R^{11})OR^{11}$, $N(R^{11})N(R^{11})(R^{12})$, $N_3$, NO, $NO_2$, CHO, CN, $-CH(=NR^{11})$, $-CH=NNH(R^{11})$, $-CH=N(OR^{11})$, $-CH(OR^{11})_2$, $-C(=O)NR^{11}R^{12}$, $-C(=S)NR^{11}R^{12}$, $-C(=O)OR^{11}$, $R^{11}$, $OR^{11}$ or $SR^{11}$;

each $R^{11}$ or $R^{12}$ is independently H, $(C_1$-$C_8)$alkyl, $(C_2$-$C_8)$alkenyl, $(C_2$-$C_8)$alkynyl, $(C_3$-$C_8)$carbocyclyl, $(C_4$-$C_8)$carbocyclylalkyl, optionally substituted aryl, optionally substituted heteroaryl, $-C(=O)(C_1$-$C_8)$alkyl, $-S(O)_n(C_1$-$C_8)$alkyl, aryl$(C_1$-$C_8)$alkyl or $Si(R^3)_3$; or $R^{11}$ and $R^{12}$ taken together with a nitrogen to which they are both attached form a 3 to 7 membered heterocyclic ring wherein any one carbon atom of said heterocyclic ring can optionally be replaced with $-O-$, $-S(O)_n-$ or $-NR^a-$; or $R^{11}$ and $R^{12}$ taken together are $-Si(R^3)_2(X^2)_mSi(R^3)_2-$;

each $R^{20}$ is independently H, $(C_1$-$C_8)$alkyl, substituted $(C_1$-$C_8)$alkyl or halo;

wherein each $(C_1$-$C_8)$alkyl, $(C_2$-$C_8)$alkenyl, $(C_2$-$C_8)$alkynyl or aryl$(C_1$-$C_8)$alkyl of each $R^1$, $R^3$, $R^4$, $R^5$, $R^6$, $R^{18}$, $R^{19}$, $R^{20}$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1$-$C_8)$alkyl is optionally replaced with $-O-$, $-S(O)_n-$ or $-NR^a-$;

said method comprising:
(a) providing a compound of Formula II

Formula II

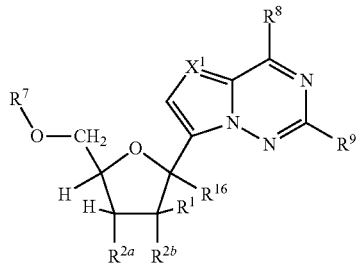

or an acceptable salt thereof;
wherein $R^{16}$ is OH, $OR^{18}$, $-OC(O)OR^{18}$ or $-OC(O)R^{18}$;

(b) treating the compound of Formula II with a cyanide reagent and a Lewis acid;
thereby forming the compound of Formula I;
provided that when the compound of Formula II is:

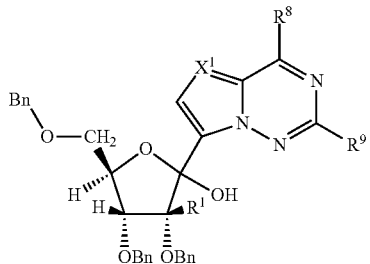

wherein $X^1$ is CH or N, $R^1$ is $CH_3$, $R^8$ is $NH_2$, and $R^9$ is $NH_2$ or H or;

wherein $X^1$ is CH, $R^1$ is $CH_3$, $R^8$ is OH, and $R^9$ is $NH_2$ or;

wherein $X^1$ is CH, each $R^1$ and $R^9$ is H and $R^8$ is $NH_2$;

then said cyanide reagent is not $(CH_3)_3SiCN$ or said Lewis acid is not $BF_3$—$O(CH_2CH_3)_2$.

Also provided are compounds of Formula II that are useful intermediates for the preparation of compounds of Formula I. Provided are compounds of Formula II represented by Formula VI:

Formula VI

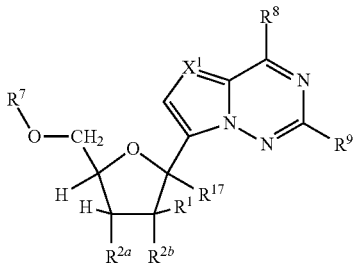

or an acceptable salt, thereof;
wherein:
$R^1$ is H, $(C_1-C_8)$alkyl, $(C_4-C_8)$carbocyclylalkyl, $(C_1-C_8)$ substituted alkyl, $(C_2-C_8)$alkenyl, $(C_2-C_8)$substituted alkenyl, $(C_2-C_8)$alkynyl, $(C_2-C_8)$substituted alkynyl, or aryl $(C_1-C_8)$alkyl;

each $R^{2a}$ or $R^{2b}$ is independently H, F or $OR^4$;

each $R^3$ is independently $(C_1-C_8)$alkyl, $(C_1-C_8)$ substituted alkyl, $C_6-C_{20}$ aryl, $C_6-C_{20}$ substituted aryl, $C_2-C_{20}$ heterocyclyl, $C_2-C_{20}$ substituted heterocyclyl, $C_7-C_{20}$ arylalkyl, $C_7-C_{20}$ substituted arylalkyl, $(C_1-C_8)$alkoxy, or $(C_1-C_8)$ substituted alkoxy;

each $R^4$ or $R^7$ is independently H, optionally substituted allyl, —$C(R^5)_2R^6$, $Si(R^3)_3$, $C(O)R^5$, $C(O)OR^5$, —$C(R^5)_2)_m$—$R^{15}$ or

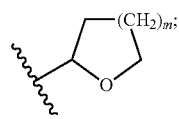

or any two of $R^4$ or $R^7$ when taken together are —$C(R^{19})_2$—, —$C(O)$— or —$Si(R^3)_2(X^2)_mSi(R^3)_2$—;

each $R^{15}$ is independently —O—$C(R^5)_2R^6$, —$Si(R^3)_3$, $C(O)OR^5$, —$OC(O)R^5$ or

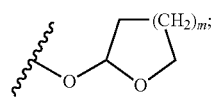

each $R^5$, $R^{18}$ or $R^{19}$ is independently H, $(C_1-C_8)$alkyl, $(C_1-C_8)$ substituted alkyl, $(C_2-C_8)$alkenyl, $(C_2-C_8)$ substituted alkenyl, $(C_2-C_8)$alkynyl, $(C_2-C_8)$ substituted alkynyl, $C_6-C_{20}$ aryl, $C_6-C_{20}$ substituted aryl, $C_2-C_{20}$ heterocyclyl, $C_2-C_{20}$ substituted heterocyclyl, $C_7-C_{20}$ arylalkyl, or $C_7-C_{20}$ substituted arylalkyl;

each $R^6$ is independently $C_6-C_{20}$ aryl, $C_6-C_{20}$ substituted aryl, or optionally substituted heteroaryl;

each $R^a$ is independently H, $(C_1-C_8)$alkyl, $(C_2-C_8)$alkenyl, $(C_2-C_8)$alkynyl, aryl$(C_1-C_8)$alkyl, $(C_4-C_8)$carbocyclylalkyl, —$C(=O)OR^{11}$, —$C(=O)OR^{11}$, —$C(=O)NR^{11}R^{12}$, —$C(=O)SR^{11}$, —$S(O)R^{11}$, —$S(O)_2R^{11}$, —$S(O)(OR^{11})$, —$S(O)_2(OR^{11})$, or —$SO_2NR^{11}R^{12}$;

$X^1$ is C—$R^{10}$ or N;
each $X^2$ is O or $CH_2$;
each n is 1 or 2;
each n is independently 0, 1 or 2;

each $R^8$ is halogen, $NR^{11}R^{12}$, $N(R^{11})OR^{11}$, $NR^{11}NR^{11}R^{12}$, $N_3$, NO, $NO_2$, CHO, CH(=$NR^{11}$), —CH=$NHNR^{11}$, —CH=$N(OR^{11})$, —$CH(OR^{11})_2$, —$C(=O)NR^{11}R^{12}$, —$C(=S)NR^{11}R^{12}$, —$C(=O)OR^{11}$, $(C_1-C_8)$alkyl, $(C_2-C_8)$alkenyl, $(C_2-C_8)$alkynyl, $(C_4-C_8)$carbocyclylalkyl, optionally substituted aryl, optionally substituted heteroaryl, —$C(=O)(C_1-C_8)$alkyl, —$S(O)_n(C_1-C_8)$alkyl, aryl$(C_1-C_8)$alkyl, CN, $OR^{11}$ or $SR^{11}$;

each $R^9$ or $R^{10}$ is independently H, halogen, $NR^{11}R^{12}$, $N(R^{11})OR^{11}$, $N(R^{11})N(R^{11})(R^{12})$, $N_3$, NO, $NO_2$, CHO, CN, —CH(=$NR^{11}$), —CH=$NNH(R^{11})$, —CH=$N(OR^{11})$, —$CH(OR^{11})_2$, —$C(=O)NR^{11}R^{12}$, —$C(=S)NR^{11}R^{12}$, —$C(=O)OR^{11}$, $R^{11}$, $OR^{11}$ or $SR^{11}$;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$ carbocyclylalkyl, optionally substituted aryl, optionally substituted heteroaryl, —$C(=O)(C_1-C_8)$alkyl, —$S(O)_n(C_1-C_8)$ alkyl, aryl$(C_1-C_8)$alkyl or $Si(R^3)_3$; or $R^{11}$ and $R^{12}$ taken together with a nitrogen to which they are both attached form a 3 to 7 membered heterocyclic ring wherein any one carbon atom of said heterocyclic ring can optionally be replaced with —O—, —$S(O)_n$— or —$NR^a$—; or $R^{11}$ and $R^{12}$ taken together are —$Si(R^3)_2(X^2)_mSi(R^3)_2$—;

$R^{17}$ is OH, $OR^{18}$, —$OC(O)OR^{18}$ or —$OC(O)R^{18}$;

wherein each $(C_1-C_8)$alkyl, $(C_2-C_8)$alkenyl, $(C_2-C_8)$alkynyl or aryl$(C_1-C_8)$alkyl of each $R^1$, $R^3$, $R^4$, $R^5$, $R^6$, $R^{18}$, $R^{19}$, $R^{11}$ or $R^{12}$ is, independently, optionally substituted with one or more halo, hydroxy, CN, $N_3$, $N(R^a)_2$ or $OR^a$; and wherein one or more of the non-terminal carbon atoms of each said $(C_1-C_8)$alkyl is optionally replaced with —O—, —$S(O)_n$— or —$NR^a$—;

provided that when $R^{17}$ is OH or $OCH_3$, $R^1$ is H or $CH_3$ and each $R^{2a}$ and $R^{2b}$ is $OR^4$, then each $R^7$ and each $R^4$ is not H; and provided that the compound of Formula VI is not a compound of Formula VII Formula VII

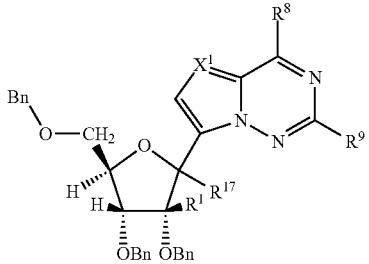

wherein $R^{17}$ is OH and
(a) $X^1$ is CH, $R^1$ is $CH_3$, $R^8$ is $NH_2$ and $R^9$ is $NH_2$ or H; or
(b) $X^1$ is CH, $R^1$ is $CH_3$, $R^8$ is OH and $R^9$ is $NH_2$; or
(c) $X^1$ is CH, each $R^1$ and $R^9$ is H and $R^8$ is $NH_2$; or
(d) $X^1$ is N, $R^1$ is $CH_3$, $R^8$ is $NH_2$, and $R^9$ is H, $NH_2$ or $SCH_3$;
(e) $X^1$ is N, $R^1$ is $CH_3$, $R^8$ is $SCH_3$ or $NHCH_3$, and $R^9$ is $SCH_3$; or
(f) $X^1$ is N, $R^1$ is $CH_3$, $R^8$ is $OCH_3$, and $R^9$ is $SCH_3$, $SO_2CH_3$ or $NH_2$;

or wherein $R^{17}$ is $OCH_3$, $X^1$ is CH, each $R^1$ and $R^9$ is H and $R^8$ is $NH_2$.

DETAILED DESCRIPTION OF EXEMPLARY EMBODIMENTS

Reference will now be made in detail to certain embodiments of the invention, examples of which are illustrated in the accompanying description, structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention.

In one embodiment, provided is a method of preparing a compound of Formula I represented by a compound of Formula Ib

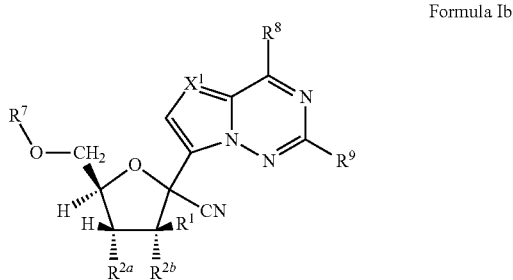

Formula Ib or an acceptable salt, thereof;
wherein the variables are defined as for Formula I;
said method comprising:
(a) providing a compound of Formula IIb

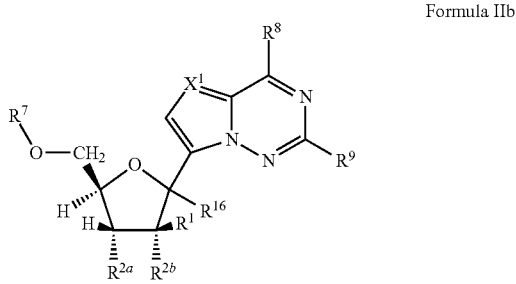

Formula IIb or an acceptable salt thereof;
wherein the variables are defined as for Formula II;
(b) treating the compound of Formula IIb with a cyanide reagent and a Lewis acid;
thereby forming the compound of Formula Ib;
provided that when the compound of Formula IIb is:

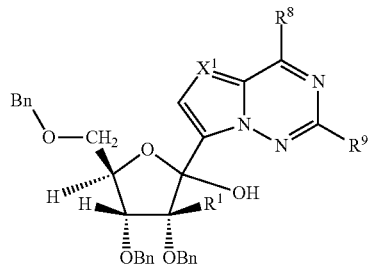

wherein $X^1$ is CH or N, $R^1$ is $CH_3$, $R^8$ is $NH_2$, and $R^9$ is $NH_2$ or H or;
wherein $X^1$ is CH, $R^1$ is $CH_3$, $R^8$ is OH, and $R^9$ is $NH_2$ or;
wherein $X^1$ is CH, each $R^1$ and $R^9$ is H and $R^8$ is $NH_2$;
then said cyanide reagent is not $(CH_3)_3SiCN$ or said Lewis acid is not $BF_3$—$O(CH_2CH_3)_2$.

In another embodiment of the method of preparing a compound of Formula Ib from a compound of Formula IIb, $R^{16}$ of Formula IIb is OH or $OR^{18}$. The following additional independent aspects of this embodiment are as follows:
(a) $R^1$ is H. $R^1$ is $CH_3$.
(b) $X^1$ is C—$R^{10}$, $X^1$ is C—H, $X^1$ is N.
(c) $R^8$ is $NR^{11}R^{12}$, $R^8$ is $OR^{11}$, $R^8$ is $SR^{11}$.
(d) $R^9$ is H, $R^9$ is $NR^{11}R^{12}$, $R^9$ is $SR^{11}$.
(e) $R^{2b}$ is $OR^4$, $R^{2b}$ is F. Each $R^{2a}$ and $R^{2b}$ is independently $OR^4$, $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is OH. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are —$C(R^{19})_2$—. Each $R^{2a}$ and $R^{2b}$ is $OR^4$ wherein the two $R^4$ taken together are —$C(CH_3)_2$—. Each $R^{2a}$ and $R^{2b}$ is $OR^4$ wherein the two $R^4$ taken together are —$CH(R^{19})$—. Each $R^{2a}$ and $R^{2b}$ is $OR^4$ wherein the two $R^4$ taken together are —$CH(R^{19})$— wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F, $R^{2a}$ is H.
(f) $R^7$ is $C(O)R^5$. $R^7$ is H, $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2(t$-butyl) wherein each $R^3$ is $CH_3$. $R^7$ is $Si(R^3)_2(t$-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are —$C(CH_3)_2$—. $R^7$ is $Si(R^3)_3$ and each $R^{2a}$ and $R^{2b}$ is $OR^4$ wherein the two $R^4$ taken together are —$C(CH_3)_2$—. $R^7$ is $Si(R^3)_2(t$-butyl) wherein each $R^3$ is $CH_3$ and each $R^{2a}$ and $R^{2b}$ is $OR^4$ wherein the two $R^4$ taken together are —$C(CH_3)_2$—. $R^7$ is $Si(R^3)_2(t$-butyl) wherein each $R^3$ is independently phenyl or substituted phenyl and each $R^{2a}$ and $R^{2b}$ is $OR^4$ wherein the two $R^4$ taken together are —$C(CH_3)_2$—. $R^7$ is tetrahydro-2H-pyran-2-yl and each $R^{2a}$ and $R^{2b}$ is $OR^4$ wherein the two $R^4$ taken together are —$C(CH_3)_2$—. $R^7$ is $C(O)R^5$ and each $R^{2a}$ and $R^{2b}$ is $OR^4$ wherein the two $R^4$ taken together are —$C(CH_3)_2$—. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are —$CH(R^{19})$— wherein $R^{19}$ is phenyl or substituted phenyl. $R^7$ is $Si(R^3)_3$ and each $R^{2a}$ and $R^{2b}$ is $OR^4$ wherein the two $R^4$ taken together are —$CH(R^{19})$— wherein $R^{19}$ is phenyl or substituted phenyl. $R^7$ is $Si(R^3)_2(t$-butyl) wherein each $R^3$ is $CH_3$ and each $R^{2a}$ and $R^{2b}$ is $OR^4$ wherein the two $R^4$ taken together are —$CH(R^{19})$— wherein $R^{19}$ is phenyl or substituted phenyl. $R^7$ is $Si(R^3)_2(t$-butyl) wherein each $R^3$ is independently phenyl or substituted phenyl and each $R^{2a}$ and $R^{2b}$ is $OR^4$ wherein the two $R^4$ taken together are —$CH(R^{19})$— wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are —CH($R^{19}$)— wherein $R^{19}$ is phenyl or substituted phenyl. $R^7$ is C(O)$R^5$ and each $R^{2a}$ and $R^{2b}$ is $OR^4$ wherein the two $R^4$ taken together are —CH($R^{19}$)— wherein $R^{19}$ is phenyl or substituted phenyl. $R^7$ is C(O)$R^5$ wherein $R^5$ is phenyl or substituted phenyl and $R^{2b}$ is F. $R^7$ is H, each $R^{2a}$ and $R^{2b}$ is $OR^4$, each $R^4$ is H and $R^{16}$ is $OR^{18}$. $R^7$ is H, each $R^{2a}$ and $R^{2b}$ is $OR^4$, each $R^4$ is H and $R^{16}$ is $OR^{18}$ wherein $R^{18}$ is optionally substituted (C$_1$-C$_8$)alkyl.

(g) The cyanide reagent is ($R^3$)$_3$SiCN. The cyanide reagent is (CH$_3$)$_3$SiCN. The cyanide reagent is $R^5$C(O)CN. The cyanide reagent is $R^5$C(O)CN wherein $R^5$ is (C$_1$-C$_8$) alkoxy or (C$_1$-C$_8$) substituted alkoxy.

(h) The Lewis acid comprises boron. The Lewis acid comprises BF$_3$ or BCl$_3$. The Lewis acid is BF$_3$—O($R^{13}$)$_2$, BF$_3$—S($R^{13}$)$_2$, BCl$_3$—O($R^{13}$)$_2$ or BCl$_3$—S($R^{13}$)$_2$ wherein each $R^{13}$ is independently (C$_1$-C$_8$)alkyl, (C$_1$-C$_8$) substituted alkyl, (C$_2$-C$_8$)alkenyl, (C$_2$-C$_8$) substituted alkenyl, (C$_2$-C$_8$) alkynyl, (C$_2$-C$_8$) substituted alkynyl, C$_6$-C$_{20}$ aryl, C$_6$-C$_{20}$ substituted aryl, C$_2$-C$_{20}$ heterocyclyl, C$_2$-C$_{20}$ substituted heterocyclyl, C$_7$-C$_{20}$ arylalkyl, or C$_7$-C$_{20}$ substituted arylalkyl; wherein each (C$_1$-C$_8$)alkyl, (C$_2$-C$_8$)alkenyl, (C$_2$-C$_8$) alkynyl or aryl(C$_1$-C$_8$)alkyl of each $R^{13}$ is, independently, optionally substituted with one or more halogens and wherein one or more of the non-terminal carbon atoms of each said (C$_1$-C$_8$)alkyl is optionally replaced with —O— or —S(O)$_n$—; or two $R^{13}$ when taken together with the oxygen to which they are both attached form a 3 to 7 membered heterocyclic ring wherein one carbon atom of said heterocyclic ring can optionally be replaced with —O— or —S(O)$_n$—. The Lewis acid is BF$_3$—O($R^{13}$)$_2$ and $R^{13}$ is (C$_1$-C$_8$)alkyl. The Lewis acid is ($R^{20}$)$_3$CS(O)$_2$OSi($R^3$)$_3$ wherein at least two $R^{20}$ are halo. The Lewis acid is ($R^{20}$)$_3$CS(O)$_2$OSi(CH$_3$)$_3$ wherein at least two $R^{20}$ are fluorine. The Lewis acid is trimethylsilyltriflate. The Lewis acid is a transition metal salt of ($R^{20}$)$_3$CS(O)$_2$OH wherein at least two $R^{20}$ are halo. The Lewis acid is a transition metal salt of ($R^{20}$)$_3$CS(O)$_2$OH wherein at least two $R^{20}$ are fluorine. The Lewis acid is a transition metal triflate. The Lewis acid is a lanthanide salt of ($R^{20}$)$_3$CS(O)$_2$OH wherein at least two $R^{20}$ are halo. The Lewis acid is a lanthanide salt of ($R^{20}$)$_3$CS(O)$_2$OH wherein at least two $R^{20}$ are fluorine. The Lewis acid is a lanthanide triflate. The Lewis acid is an alkaline earth metal salt of ($R^{20}$)$_3$CS(O)$_2$OH wherein at least two $R^{20}$ are halo. The Lewis acid is an alkaline earth metal salt of ($R^{20}$)$_3$CS(O)$_2$OH wherein at least two $R^{20}$ are fluorine. The Lewis acid is an alkaline earth metal triflate. The Lewis acid is a aluminum, gallium, indium, thallium, tin, lead or bismuth salt of ($R^{20}$)$_3$CS(O)$_2$OH wherein at least two $R^{20}$ are halo. The Lewis acid is a aluminum, gallium, indium, thallium, tin, lead or bismuth salt of ($R^{20}$)$_3$CS(O)$_2$OH wherein at least two $R^{20}$ are fluorine. The Lewis acid is a triflate of aluminum, gallium, indium, thallium, tin, lead or bismuth. The Lewis acid comprises a transition metal or salt thereof. The Lewis acid comprises titanium or a salt thereof. The Lewis acid comprises TiCl$_4$. The Lewis acid comprises a lanthanide or a salt thereof. The Lewis acid comprises scandium or a salt thereof. The Lewis acid comprises vanadium or a salt thereof. The Lewis acid comprises tin or a salt thereof. The Lewis acid comprises SnCl$_4$. The Lewis acid comprises zinc or a salt thereof. The Lewis acid comprises ZnCl$_2$. The Lewis acid comprises samarium or a salt thereof. The Lewis acid comprises nickel or a salt thereof. The Lewis acid comprises copper or a salt thereof. The Lewis acid comprises aluminum or a salt thereof. The Lewis acid comprises gold or a salt thereof.

In another embodiment of a method of preparing a compound of Formula Ib, $R^{16}$ of Formula IIb is —OC(O)$R^{18}$. The following are additional independent aspects of this embodiment:

(a) $R^1$ is H. $R^1$ is CH$_3$.

(b) $X^1$ is C—$R^{10}$, $X^1$ is C—H. $X^1$ is N.

(c) $R^8$ is N$R^{11}R^{12}$. $R^8$ is O$R^{11}$, $R^8$ is S$R^{11}$.

(d) $R^9$ is H. $R^9$ is N$R^{11}R^{12}$, $R^9$ is S$R^{11}$.

(e) $R^{2b}$ is $OR^4$, $R^{2b}$ is F. Each $R^{2a}$ and $R^{2b}$ is independently $OR^4$, $R^{2a}$ is $OR^4$ and $R^{2b}$ is F. $R^{2a}$ is $OR^4$, $R^{2b}$ is F and $R^4$ is C(O)$R^5$. $R^{2a}$ is $OR^4$, $R^{2b}$ is F and $R^4$ is C(O)$R^5$ wherein $R^5$ is phenyl or substituted phenyl. $R^{2b}$ is $OR^4$ wherein $R^4$ is C($R^5$)$_2$$R^6$ and $R^6$ is phenyl or substituted phenyl. $R^{2b}$ is $OR^4$ wherein $R^4$ is CH$_2$$R^6$ and $R^6$ is phenyl. $R^{2b}$ is $OR^4$ wherein $R^4$ is CH$_2$$R^6$ and $R^6$ is substituted phenyl. Each $R^{2a}$ and $R^{2b}$ is OH. Each $R^{2a}$ and $R^{2b}$ is $OR^4$ wherein each $R^4$ is independently C($R^5$)$_2$$R^6$ and $R^6$ is phenyl or substituted phenyl. Each $R^{2a}$ and $R^{2b}$ is $OR^4$ wherein each $R^4$ is CH$_2$$R^6$ and $R^6$ is phenyl. Each $R^{2a}$ and $R^{2b}$ is $OR^4$ wherein each $R^4$ is CH$_2$$R^6$ and each $R^6$ is independently substituted phenyl. Each $R^{2a}$ and $R^{2b}$ is $OR^4$ wherein the two $R^4$ taken together are —C($R^{19}$)$_2$—. Each $R^{2a}$ and $R^{2b}$ is $OR^4$ wherein the two $R^4$ taken together are —C(CH$_3$)$_2$—. Each $R^{2a}$ and $R^{2b}$ is $OR^4$ wherein the two $R^4$ taken together are —CH($R^{19}$)—. Each $R^{2a}$ and $R^{2b}$ is $OR^4$ wherein the two $R^4$ taken together are —CH($R^{19}$)— wherein $R^{19}$ is phenyl or substituted phenyl. $R^{2a}$ is $OR^4$ wherein $R^4$ is C($R^5$)$_2$$R^6$, $R^6$ is phenyl or substituted phenyl and $R^{2b}$ is F. $R^{2a}$ is H.

(f) $R^7$ is C(O)$R^5$. $R^7$ is H. $R^7$ is C($R^5$)$_2$$R^6$ and $R^6$ is phenyl or substituted phenyl. $R^7$ is CH$_2$$R^6$ and $R^6$ is phenyl. $R^7$ is CH$_2$$R^6$ and $R^6$ is substituted phenyl. $R^7$ is C($R^5$)$_2$$R^6$ and each $R^5$ and $R^6$ is independently phenyl or substituted phenyl. $R^7$ is Si($R^3$)$_3$. $R^7$ is Si($R^3$)$_2$(t-butyl) wherein each $R^3$ is CH$_3$. $R^7$ is Si($R^3$)$_2$(t-butyl) wherein each $R^3$ is independently phenyl or substituted phenyl. $R^7$ is tetrahydro-2H-pyran-2-yl. $R^7$ is C($R^5$)$_2$$R^6$ wherein each $R^5$ and $R^6$ is independently phenyl or substituted phenyl and each $R^{2a}$ and $R^{2b}$ is $OR^4$ wherein the two $R^4$ taken together are —C(CH$_3$)$_2$—. $R^7$ is Si($R^3$)$_3$ and each $R^{2a}$ and $R^{2b}$ is $OR^4$ wherein the two $R^4$ taken together are —C(CH$_3$)$_2$—. $R^7$ is Si($R^3$)$_2$(t-butyl) wherein each $R^3$ is CH$_3$ and each $R^{2a}$ and $R^{2b}$ is $OR^4$ wherein the two $R^4$ taken together are —C(CH$_3$)$_2$—. $R^7$ is Si($R^3$)$_2$(t-butyl) wherein each $R^3$ is independently phenyl or substituted phenyl and each $R^{2a}$ and $R^{2b}$ is $OR^4$ wherein the two $R^4$ taken together are —C(CH$_3$)$_2$—. $R^7$ is tetrahydro-2H-pyran-2-yl and each $R^{2a}$ and $R^{2b}$ is $OR^4$ wherein the two $R^4$ taken together are —C(C$_1$-C$_3$)$_3$—. $R^7$ is C(O)$R^5$ each $R^{2a}$ and $R^{2b}$ is $OR^4$ wherein the two $R^4$ taken together are —C(CH$_3$)$_2$—. $R^7$ is C($R^5$)$_2$$R^6$ wherein each $R^5$ and $R^6$ is independently phenyl or substituted phenyl and each $R^{2a}$ and $R^{2b}$ is $OR^4$ wherein the two $R^4$ taken together are —CH($R^{19}$)— wherein $R^{19}$ is phenyl or substituted phenyl. $R^7$ is Si($R^3$)$_3$ and each $R^{2a}$ and $R^{2b}$ is $OR^4$ wherein the two $R^4$ taken together are —CH($R^{19}$)— wherein $R^{19}$ is phenyl or substituted phenyl. $R^7$ is Si($R^3$)$_2$(t-butyl) wherein each $R^3$ is CH$_3$ and each $R^{2a}$ and $R^{2b}$ is $OR^4$ wherein the two $R^4$ taken together are —CH($R^{19}$)— wherein $R^{19}$ is phenyl or substituted phenyl. $R^7$ is Si($R^3$)$_2$(t-butyl) wherein each $R^3$ is independently phenyl or substituted phenyl and each $R^{2a}$ and $R^{2b}$ is $OR^4$ wherein the two $R^4$ taken together are —CH($R^{19}$)— wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are —CH($R^{19}$)— wherein $R^{19}$ is phenyl or substituted phenyl. $R^7$ is C(O)$R^5$ and each $R^{2a}$ and $R^{2b}$ is $OR^4$ wherein the two $R^4$ taken together are —CH($R^{19}$)— wherein $R^{19}$ is phenyl or substituted phenyl. $R^7$ is C(O)$R^5$ wherein $R^5$ is phenyl or substituted phenyl and $R^{2b}$ is F.

(g) The cyanide reagent is $(R^3)_3SiCN$. The cyanide reagent is $(CH_3)_3SiCN$. The cyanide reagent is $R^5C(O)CN$. The cyanide reagent is $R^5C(O)CN$ wherein $R^5$ is $(C_1-C_8)$ alkoxy or $(C_1-C_8)$ substituted alkoxy.

(h) The Lewis acid comprises boron. The Lewis acid comprises $BF_3$ or $BCl_3$. The Lewis acid is $BF_3$—$O(R^{13})_2$, $BF_3$—$S(R^{13})_2$, $BCl_3$—$O(R^{13})_2$ or $BCl_3$—$S(R^{13})_2$ wherein each $R^{13}$ is independently $(C_1-C_8)$alkyl, $(C_1-C_8)$ substituted alkyl, $(C_2-C_8)$alkenyl, $(C_2-C_8)$ substituted alkenyl, $(C_2-C_8)$ alkynyl, $(C_2-C_8)$ substituted alkynyl, $C_6-C_{20}$ aryl, $C_6-C_{20}$ substituted aryl, $C_2-C_{20}$ heterocyclyl, $C_2-C_{20}$ substituted heterocyclyl, $C_7-C_{20}$ arylalkyl, or $C_7-C_{20}$ substituted arylalkyl; wherein each $(C_1-C_8)$alkyl, $(C_2-C_8)$alkenyl, $(C_2-C_8)$ alkynyl or aryl$(C_1-C_8)$alkyl of each $R^{13}$ is, independently, optionally substituted with one or more halogens and wherein one or more of the non-terminal carbon atoms of each said $(C_1-C_8)$alkyl is optionally replaced with —O— or —S(O)$_n$—; or two $R^{13}$ when taken together with the oxygen to which they are both attached form a 3 to 7 membered heterocyclic ring wherein one carbon atom of said heterocyclic ring can optionally be replaced with —O— or —S(O)$_n$—. The Lewis acid is $BF_3$—$O(R^{13})_2$ and $R^{13}$ is $(C_1-C_8)$alkyl. The Lewis acid is $(R^{20})_3CS(O)_2OSi(R^3)_3$ wherein at least $R^{20}$ are halo. The Lewis acid is $(R^{20})_3CS(O)_2OSi(CH_3)_3$ wherein at least two $R^{20}$ are fluorine. The Lewis acid is trimethylsilyltriflate. The Lewis acid is a transition metal triflate. The Lewis acid is a lanthanide triflate. The Lewis acid is an alkaline metal triflate. The Lewis acid is a triflate of aluminum, gallium, indium, thallium, tin, lead or bismuth. The Lewis acid comprises a transition metal or salt thereof. The Lewis acid comprises titanium or a salt thereof. The Lewis acid comprises $TiCl_4$. The Lewis acid comprises a lanthanide or a salt thereof. The Lewis acid comprises scandium or a salt thereof. The Lewis acid comprises vanadium or a salt thereof. The Lewis acid comprises tin or a salt thereof. The Lewis acid comprises $SnCl_4$. The Lewis acid comprises zinc or a salt thereof. The Lewis acid comprises $ZnCl_2$. The Lewis acid comprises samarium or a salt thereof. The Lewis acid comprises nickel or a salt thereof. The Lewis acid comprises copper or a salt thereof. The Lewis acid comprises aluminum or a salt thereof. The Lewis acid comprises gold or a salt thereof.

(i) $R^{18}$ is $(C_1-C_8)$alkyl or substituted $(C_1-C_8)$alkyl. $R^{18}$ is $(C_1-C_8)$alkyl. $R^{18}$ is methyl.

In another embodiment of the method of preparing a compound of Formula Ib, the compound of Formula Ib is represented by Formula Ic Formula Ic or a salt thereof; and the compound of Formula IIb is represented by Formula IIc Formula IIc or a salt thereof;
wherein:
$R^{16}$ is OH or $OR^{18}$;
$R^{18}$ is optionally substituted $(C_1-C_8)$alkyl;
the Lewis acid is $(R^{20})_3CS(O)_2OSi(R^3)_3$ or a metal salt of $(R^{20})_3CS(O)_2OH$;
at least two $R^{20}$ are halogen; and
said metal is selected from the group consisting aluminum, gallium, indium, thallium, tin, lead, bismuth, an alkaline earth metal, a transition metal and a lanthanide; and
the remaining variables are defined as for Formula IIb. The following are additional independent aspects of this embodiment:

(a) $R^1$ is H. $R^1$ is $CH_3$.
(b) $X^1$ is C—$R^{10}$. $X^1$ is C—H. $X^1$ is N.
(c) $R^8$ is $NR^{11}R^{12}$. $R^8$ is $OR^{11}$. $R^8$ is $SR^{11}$.
(d) $R^9$ is H. $R^9$ is $NR^{11}R^{12}$. $R^9$ is $SR^{11}$.
(e) $R^{2b}$ is $OR^4$. $R^{2b}$ is F. $R^{2b}$ is F and $R^4$ is $C(O)R^5$. $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $OR^4$ and $R^{2b}$ is OH. $R^{2b}$ is $OR^4$ wherein each $R^4$ is independently $C(R^5)_2R^6$ and $R^6$ is phenyl or substituted phenyl. $R^{2b}$ is $OR^4$ wherein each $R^4$ is $CH_2R^6$ and $R^6$ is phenyl. $R^{2b}$ is $OR^4$ wherein each $R^4$ is $CH_2R^6$ and each $R^6$ is independently substituted phenyl. $R^{2b}$ is $OR^4$ wherein the two $R^4$ taken together are —$C(R^{19})_2$—. $R^{2b}$ is $OR^4$ wherein the two is $R^4$ taken together are —$C(CH_3)_2$—. $R^{2b}$ wherein the two $R^4$ taken together are —$CH(R^{19})$—. $R^{2b}$ is $OR^4$ wherein the two $R^4$ taken together are —CH($R^{19}$)— wherein $R^{19}$ is phenyl or substituted phenyl. $R^4$ is $C(R^5)_2R^6$, $R^6$ is phenyl or substituted phenyl and $R^{2b}$ is F.

(f) $R^7$ is $C(O)R^5$. $R^7$ is H. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and $R^{2b}$ is $OR^4$ wherein the two $R^4$ taken together are —$C(CH_3)_2$—. $R^7$ is $Si(R^3)_3$ and $R^{2b}$ is $OR^4$ wherein the two $R^4$ taken together are —$C(CH_3)_2$—. $R^7$ is $Si(R^3)_2$(t-butyl) wherein each $R^3$ is $CH_3$ and $R^{2b}$ is $OR^4$ wherein the two $R^4$ taken together are —$C(CH_3)_2$—. $R^7$ is $Si(R^3)_2$(t-butyl) wherein each $R^3$ is independently phenyl or substituted phenyl and $R^{2b}$ is $OR^4$ wherein the two $R^4$ taken together are —$C(CH_3)_2$—. $R^7$ is tetrahydro-2H-pyran-2-yl and $R^{2b}$ is $OR^4$ wherein the two $R^4$ taken together are —$C(CH_3)_2$—. $R^7$ is $C(O)R^5$ and $R^{2b}$ is $OR^4$ wherein the two $R^4$ taken together are —$C(CH_3)_2$—. $R^7$ is $C(R^5)_2R^6$ wherein each $R^5$ and $R^6$ is independently phenyl or substituted phenyl and $R^{2b}$ is $OR^4$ wherein the two $R^4$ taken together are —CH($R^{19}$)— wherein $R^{19}$ is phenyl or substituted phenyl. $R^7$ is Si($R^3$)$_3$ and $R^{2b}$ is $OR^4$ wherein the two $R^4$ taken together are —CH($R^{19}$)— wherein $R^{19}$ is phenyl or substituted phenyl. $R^7$ is Si($R^3$)$_2$(t-butyl) wherein each $R^3$ is $CH_3$ and $R^{2b}$ is $OR^4$ wherein the two $R^4$ taken together are —CH($R^{19}$)— wherein $R^{19}$ is phenyl or substituted phenyl. $R^7$ is Si($R^3$)$_2$(t-butyl) wherein each $R^3$ is independently phenyl or substituted phenyl and $R^{2b}$ is $OR^4$ wherein the two $R^4$ taken together are —CH($R^{19}$)— wherein $R^{19}$ is phenyl or substituted phenyl. $R^7$ is tetrahydro-2H-pyran-2-yl and $R^{2b}$ is $OR^4$ wherein the two $R^4$ taken together are —CH($R^{19}$)— wherein $R^{19}$ is phenyl or substituted phenyl. $R^7$ is C(O)$R^5$ and $R^{2b}$ is $OR^4$ wherein the two $R^4$ taken together are —CH($R^{19}$)— wherein $R^{19}$ is phenyl or substituted phenyl. $R^7$ is C(O)$R^5$ wherein $R^5$ is phenyl or substituted phenyl and $R^{2b}$ is F. $R^7$ is H, $R^{2b}$ is $OR^4$, each $R^4$ is H and $R^{16}$ is $OR^{18}$. $R^7$ is H, $R^{2b}$ is $OR^4$, each $R^4$ is H and $R^{16}$ is $OR^{18}$ wherein $R^{18}$ is optionally substituted ($C_1$-$C_8$)alkyl.

(g) The cyanide reagent is ($R^3$)$_3$SiCN. The cyanide reagent is ($CH_3$)$_3$SiCN. The cyanide reagent is $R^5$C(O)CN. The cyanide reagent is $R^5$C(O)CN wherein $R^5$ is ($C_1$-$C_8$) alkoxy or ($C_1$-$C_8$) substituted alkoxy.

(h) The Lewis acid is ($R^{20}$)$_3$CS(O)$_2$OSi($R^3$)$_3$ wherein at least two $R^{20}$ are halo. The Lewis acid is ($R^{20}$)$_3$CS(O)$_2$OSi($CH_3$)$_3$ wherein at least two $R^{20}$ are fluorine. The Lewis acid is trimethylsilyltriflate. The Lewis acid is a transition metal salt of ($R^{20}$)$_3$CS(O)$_2$OH wherein at least two $R^{20}$ are halo. The Lewis acid is a transition metal salt of ($R^{20}$)$_3$CS(O)$_2$OH wherein at least two $R^{20}$ are fluorine. The Lewis acid is a transition metal triflate. The Lewis acid is a lanthanide salt of ($R^{20}$)$_3$CS(O)$_2$OH wherein at least two $R^{20}$ are halo. The Lewis acid is a lanthanide salt of) ($R^{20}$)$_3$CS(O)$_2$OH wherein at least two $R^{20}$ are fluorine. The Lewis acid is a lanthanide triflate. The Lewis acid is an alkaline earth metal salt of ($R^{20}$)$_3$CS(O)$_2$OH wherein at least two $R^{20}$ are halo. The Lewis acid is a alkaline earth metal salt of ($R^{20}$)$_3$CS(O)$_2$OH wherein at least two $R^{20}$ are fluorine. The Lewis acid is an alkaline earth metal triflate. The Lewis acid is a aluminum, gallium, indium, thallium, tin, lead or bismuth salt of ($R^{20}$)$_3$CS(O)$_2$OH wherein at least two $R^{20}$ are halo. The Lewis acid is a aluminum, gallium, indium, thallium, tin, lead or bismuth salt of) ($R^{20}$)$_3$CS(O)$_2$OH wherein at least two $R^{20}$ are fluorine. The Lewis acid is a triflate of aluminum, gallium, indium, thallium, tin, lead or bismuth. The Lewis acid is a triflate of indium.

In another embodiment of the method of preparing a compound of Formula Ic from a compound of Formula IIc, each $X^1$ is CH and each $R^8$ is $NR^{11}R^{12}$. In another aspect of this embodiment, each $R^8$ is $NH_2$. In another aspect of this embodiment, each $R^9$ is H. In another aspect of this embodiment, each $R^8$ is NH, and each $R^9$ is H. In another aspect of this embodiment, the Lewis acid is ($R^{20}$)$_3$CS(O)$_2$OSi($CH_3$)$_3$ wherein at least two $R^{20}$ are fluorine. In another aspect of this embodiment, the Lewis acid is trimethylsilyl triflate. In another aspect of this embodiment, the Lewis acid is a transition metal triflate. In another aspect of this embodiment, the Lewis acid is a lanthanide triflate. In another aspect of this embodiment, the Lewis acid is an alkaline earth metal triflate. In another aspect of this embodiment, the Lewis acid is a triflate of aluminum, gallium, indium, thallium, tin, lead or bismuth. In another aspect of this embodiment, the Lewis acid is a triflate of indium. In another aspect of this embodiment, the cyanide reagent is ($R^3$)$_3$SiCN. In another aspect of this embodiment, the cyanide reagent is ($CH_3$)$_3$SiCN. In another aspect of this embodiment, the Lewis acid is ($R^{20}$)$_3$CS(O)$_2$OSi($CH_3$)$_3$ wherein at least two $R^{20}$ are fluorine and the cyanide reagent is ($R^3$)$_3$SiCN. In another aspect of this embodiment, the Lewis acid is trimethylsilyl triflate and the cyanide reagent is ($R^3$)$_3$SiCN. In another aspect of this embodiment, the Lewis acid is trimethylsilyl triflate and the cyanide reagent is ($CH_3$)$_3$SiCN. In another aspect of this embodiment, $R^7$ is C(O)$R^5$. In another aspect of this embodiment, $R^7$ is H. In another aspect of this embodiment, $R^7$ is $CH_2R^6$ and $R^6$ is phenyl or substituted phenyl. In another aspect of this embodiment, $R^7$ is Si($R^3$)$_3$. In another aspect of this embodiment, $R^7$ is tetrahydro-2H-pyran-2-yl. In another aspect of this embodiment, $R^7$ is Si($R^3$)$_3$ and $R^{2b}$ is $OR^4$ wherein the two $R^4$ taken together are —C($CH_3$)$_2$—. In another aspect of this embodiment, $R^7$ is tetrahydro-2H-pyran-2-yl and $R^{2b}$ is $OR^4$ wherein the two $R^4$ taken together are —C($CH_3$)$_2$—. In another aspect of this embodiment, $R^7$ is C(O)$R^5$ and $R^{2b}$ is $OR^4$ wherein the two $R^4$ taken together are —C($CH_3$)$_2$—. In another aspect of this embodiment, $R^7$ is C(O)$R^5$ wherein $R^5$ is phenyl or substituted phenyl and $R^{2b}$ is F. In another aspect of this embodiment, $R^7$ is H, $R^{2b}$ is $OR^4$, each $R^4$ is H and $R^{16}$ is $OR^{18}$. In another aspect of this embodiment, $R^7$ is H, $R^{2b}$ is $OR^4$, each $R^4$ is H and $R^{16}$ is $OR^{18}$ wherein $R^{18}$ is optionally substituted ($C_1$-$C_8$)alkyl.

In another embodiment of the method of preparing a compound of Formula Ic from a compound of Formula IIc, each $X^1$ is CH, each $R^1$ is H or ($C_1$-$C_8$)alkyl, each $R^8$ is $NH_2$ and each $R^9$ is H. In another aspect of this embodiment, the Lewis acid is ($R^{20}$)$_3$CS(O)$_2$OSi($CH_3$)$_3$ wherein at least two $R^{20}$ are fluorine. In another aspect of this embodiment, the Lewis acid is trimethylsilyl triflate. In another aspect of this embodiment, the Lewis acid is a transition metal triflate. In another aspect of this embodiment, the Lewis acid is a lanthanide triflate. In another aspect of this embodiment, the Lewis acid is an alkaline earth metal triflate. In another aspect of this embodiment, the Lewis acid is a triflate of aluminum, gallium, indium, thallium, tin, lead or bismuth. In another aspect of this embodiment, the Lewis acid is a triflate of indium. In another aspect of this embodiment, the cyanide reagent is ($R^3$)$_3$SiCN. In another aspect of this embodiment, the cyanide reagent is ($CH_3$)$_3$SiCN. In another aspect of this embodiment, the Lewis acid is ($R^{20}$)$_3$CS(O)$_2$OSi($CH_3$)$_3$ wherein at least two $R^{20}$ are fluorine and the cyanide reagent is ($R^3$)$_3$SiCN. In another aspect of this embodiment, the Lewis acid is trimethylsilyl triflate and the cyanide reagent is ($R^3$)$_3$SiCN. In another aspect of this embodiment, the Lewis acid is trimethylsilyl triflate and the cyanide reagent is ($CH_3$)$_3$SiCN. In another aspect of this embodiment, $R^7$ is C(O)$R^5$. In another aspect of this embodiment, $R^7$ is H. In another aspect of this embodiment, $R^7$ is $CH_2R^6$ and $R^6$ is phenyl or substituted phenyl. In another aspect of this embodiment, $R^7$ is Si($R^3$)$_3$. In another aspect of this embodiment, $R^7$ is tetrahydro-2H-pyran-2-yl. In another aspect of this embodiment, $R^7$ is Si($R^3$)$_3$ and $R^{2b}$ is $OR^4$ wherein the two $R^4$ taken together are —C($CH_3$)$_2$—. In another aspect of this embodiment, $R^7$ is tetrahydro-2H-pyran-2-yl and $R^{2b}$ is $OR^4$ wherein the two $R^4$ taken together are —C($CH_3$)$_2$—. In another aspect of this embodiment, $R^7$ is C(O)$R^5$ and $R^{2b}$ is $OR^4$ wherein the two $R^4$ taken together are —C($CH_3$)$_2$—. In another aspect of this embodiment, $R^7$ is C(O)$R^5$ wherein $R^5$ is phenyl or substituted phenyl and $R^{2b}$ is F. In another aspect of this embodiment, $R^7$ is H, $R^{2b}$ is $OR^4$, each $R^4$ is H and $R^{16}$ is $OR^{18}$. In another aspect of this embodiment, $R^7$ is H, $R^{2b}$ is $OR^4$, each $R^4$ is H and $R^{16}$ is $OR^{18}$ wherein $R^{18}$ is optionally substituted ($C_1$-$C_8$)alkyl.

Typically, the method of preparing compounds of Formula I, Ib or Ic from a compound of Formula II, IIb or IIc, respectively, are preformed in a suitable aprotic solvent at about −78 to 80° C. for about 10 minutes about 3 days. Non-limiting examples of suitable aprotic solvents include $CH_2Cl_2$, acetonitrile, $CH_2ClCH_2Cl$ or other halocarbon solvents. More typically, the method is performed at about −20 to about 65° C. for about 10 minutes to 4 hours. The mole ratio of the compound of Formula II, IIb or IIc to cyanide reagent is about 1:1 to 1:10, more typically about 1:2 to 1:6. The mole ratio of the compound of Formula II, IIb or IIc to Lewis acid is about 1:0.1 to about 1:10, more typically about 1:0.7 to about 1:6.

The conversion of the compounds of Formula II, IIb or IIc to a compound of Formula I, Ib or Ic, respectively, is promoted by Lewis acids. Many Lewis acids may promote this conversion including many that are commercially available. Non-limiting examples of Lewis acids comprising boron that are suitable for promoting this conversion are boron trifluoride etherates of methyl, ethyl, propyl, and butyl ethers; boron trifluoride-tert-butyl methyl etherate; boron trifluoride and boron trifluoride methyl sulfide complex. Non-limiting examples of Lewis acids comprising trialkylsilyl groups that are suitable for promoting this conversion are tri-($C_1$-$C_{12}$ alkyl)silyl-polyfluoro($C_1$-$C_{12}$)alkylsulfonates, trimethylsilyl polyfluoro($C_1$-$C_{12}$)alkylsulfonates, trimethylsilyl trifluoromethanesulfonate, tert-butyldimethylsilyl trifluoromethanesulfonate and triethylsilyl trifluoromethanesulfonate. Additional non-limiting examples of Lewis acids suitable for promoting this conversion are transition metal polyfluoro($C_1$-$C_{12}$)alkyisulfonates, lanthanide polyfluoro($C_1$-$C_{12}$)alkylsulfonates, alkaline earth metal polyfluoro($C_1$-$C_{12}$)alkylsulfonates, polyfluoro($C_1$-$C_{12}$)alkylsulfonates of aluminium, gallium, indium, thallium, tin, lead and bismuth, $TiCl_4$, $AlCl_3$, $ZnCl_7$, $ZnI_2$, $SnCl_4$, $InCl_3$, Sc(trifluoromethanesulfonate)$_3$, Sn(trifluoromethanesulfonate)$_2$, $InBr_3$, indium(trifluoromethanesulfonate)$_3$, $AuCl_3$, montmorilite clays, Cu(trifluoromethanesulfonate)$_2$, vanadyl trifluoromethanesulfonate, and salen complexes of Ti and Vn (Belokon, et al., Tetrahedron 2001, 771). In a preferred embodiment, the Lewis acid is trimethylsilyl trifluoromethanesulfonate. In another preferred embodiment, the Lewis acid is trimethylsilyl trifluoromethanesulfonate and the yield of the compound of Formula I, Ib or Ic is about 50% or greater. In another preferred embodiment, the Lewis acid is trimethylsilyl trifluoromethanesulfonate and the yield of the compound of Formula I, Ib or Ic is about 70% or greater. In another preferred embodiment, the Lewis acid is trimethylsilyl trifluoromethanesulfonate and the yield of the compound of Formula I, Ib or Ic is about 90% or greater. In another preferred embodiment, the Lewis acid is trimethylsilyl trifluoromethanesulfonate and the ratio of β to α anomer of the compound of formula I, Ib, or Ic is about 3.5 to 1 or greater. In another preferred embodiment, the Lewis acid is trimethylsilyl trifluoromethanesulfonate and the ratio of β to α anomer of the compound of Formula I, Ib, or Ic is about 4 to 1 or greater. In another preferred embodiment, the Lewis acid is trimethylsilyl trifluoromethanesulfonate and the ratio of β to α anomer of the compound of formula I, Ib, or Ic is about 5 to 1 or greater. In another preferred embodiment, the Lewis acid is trimethylsilyl trifluoromethanesulfonate and the ratio of β to α anomer of the compound of formula I, Ib, or Ic is about 6 to 1 or greater. In another preferred embodiment, the Lewis acid is trimethylsilyl trifluoromethanesulfonate and the ratio of β to α anomer of the compound of formula I, Ib, or Ic is about 8 to 1 or greater. In another preferred embodiment, the Lewis acid is trimethylsilyl trifluoromethanesulfonate and the ratio of β to α anomer of the compound of formula I, Ib, or Ic is about 10 to 1 or greater.

In another embodiment, provided is a method of preparing a compound of Formula II or IIb wherein $R^{16}$ is —OC(O)$R^{18}$, the method comprising:

(c) providing a compound of Formula II or IIb wherein $R^{16}$ is OH; and (d) treating the compound of Formula II or IIb wherein $R^{16}$ is OH with YC(O)$R^{18}$ wherein Y is selected from halogen, cyano, imidazol-1-yl; pyrazol-1-yl, O—C(O)$R^{18}$ or —O—C(O)O$R^{18}$;

thereby forming a compound of Formula II or IIb wherein $R^{16}$ is —OC(O)$R^{18}$.

In another embodiment, the method of preparing the compound of Formula II or IIb wherein $R^{16}$ is OC(O)$R^{18}$ has the following additional independent aspects.

(a) $R^1$ is H. $R^1$ is $CH_3$.

(b) $X^1$ is C—$R^{10}$. $X^1$ is C—H. $X^1$ is N.

(c) $R^8$ is $NR^{11}R^{12}$. $R^8$ is $OR^{11}$. $R^8$ is $SR^{11}$.

(d) $R^9$ is H. $R^9$ is $NR^{11}R^{12}$. $R^9$ is $SR^{11}$.

(e) $R^{2b}$ is $OR^4$. $R^{2b}$ is F. Each $R^{2a}$ and $R^{2b}$ is independently $OR^4$, $R^{2a}$ is $OR^4$ and $R^{2b}$ is F. $R^{2a}$ is $OR^4$, $R^{2b}$ is F and $R^4$ is C(O)$R^5$. $R^{2a}$ is $OR^4$, $R^{2b}$ is F and $R^4$ is C(O)$R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are —$C(R^{19})_2$—. Each $R^{2a}$ and $R^{2b}$ is $OR^4$ wherein the two $R^4$ taken together are —$C(CH_3)_2$—. Each $R^{2a}$ and $R^{2b}$ is $OR^4$ wherein the two $R^4$ taken together are —$CH(R^{19})$—. Each $R^{2a}$ and $R^{2b}$ is $OR^4$ wherein the two $R^4$ taken together are —$CH(R^{19})$— wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.

(f) $R^7$ is C(O)$R^5$. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are —$C(CH_3)_2$—. $R^7$ is $Si(R^3)_3$ and each $R^{2a}$ and $R^{2b}$ is $OR^4$ wherein the two $R^4$ taken together are —$C(CH_3)_2$. $R^7$ is $Si(R^3)_2$(t-butyl) wherein each $R^3$ is $CH_3$ and each $R^{2a}$ and $R^{2b}$ is $OR^4$ wherein the two $R^4$ taken together are —$C(CH_3)_2$. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are —$C(CH_3)_2$—. $R^7$ is tetrahydro-2H-pyran-2-yl and each $R^{2a}$ and $R^{2b}$ is $OR^4$ wherein the two $R^4$ taken together are —$C(CH_3)_2$—. $R^7$ is C(O)$R^5$ and each $R^{2a}$ and $R^{2b}$ is $OR^4$ wherein the two $R^4$ taken together are —$C(CH_3)_2$—. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are —$CH(R^{19})$— wherein $R^{19}$ is phenyl or substituted phenyl. $R^7$ is $Si(R^3)_3$ and each $R^{2a}$ and $R^{2b}$ is $OR^4$ wherein the two $R^4$ taken together are —CH$(R^{19})$— wherein $R^{19}$ is phenyl or substituted phenyl. $R^7$ is $Si(R^3)_2$(t-butyl) wherein each $R^3$ is $CH_3$ and each $R^{2a}$ and $R^{2b}$ is $OR^4$ wherein the two $R^4$ taken together are —CH ($R^{19}$)— wherein $R^{19}$ is phenyl or substituted phenyl. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are —CH($R^{19}$)— wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are —CH($R^{19}$)— wherein $R^{19}$ is phenyl or substituted phenyl. $R^7$ is C(O)$R^5$ and each $R^{2a}$ and $R^{2b}$ is $OR^4$ wherein the two $R^4$ taken together are —CH($R^{19}$)— wherein $R^{19}$ is phenyl or substituted phenyl. $R^7$ is C(O)$R^5$ wherein $R^5$ is phenyl or substituted phenyl and $R^{2b}$ is F.

(g) $R^{18}$ is ($C_1$-$C_8$)alkyl or substituted ($C_1$-$C_8$)alkyl. $R^{18}$ is ($C_1$-$C_8$)alkyl. $R^{18}$ methyl.

In one embodiment, the mole ratio of the compound of Formula II, IIb or IIc wherein $R^{16}$ is OH to YC(O)$R^{18}$ is about 1:1 to about 1:10, preferably about 1:1 to about 1:6.5. Typically, the compound of Formula II, IIb or IIc wherein $R^{16}$ is OH is treated with YC(O)$R^{18}$ in an aprotic solvent such as, but not limited to, pyridine, THF or ether at about −30 to about 125° C. for about 30 minutes to about 24 hours. In one embodiment, Y is halogen. In another embodiment, Y is Cl. In another embodiment, Y is cyano. In another embodiment, Y is imidazol-1-yl. In another embodiment, Y is pyrazol-1-yl. In another embodiment, Y is —O—C(O)$R^{18}$. In another embodiment, Y is —O—C(O)O$R^{18}$. In a particular embodiment, $R^{18}$ is $C_1$-$C_6$ alkyl. In another particular embodiment, $R^{18}$ is $CH_3$. In another embodiment, $R^{18}$ is $C_1$-$C_6$ alkyl and Y is —O—C(O)$R^{18}$. In another embodiment, $R^{18}$ is $CH_3$ and Y—O—C(O)$R^{18}$.

The reaction of the compound of Formula II, IIb or IIc wherein $R^{16}$ is OH with YC(O)$R^{18}$ may be catalyzed or accelerated in the presence of a suitable base. Non-limiting examples of suitable bases include triethylamine, di-isopropylethylamine, pyridine, 4-dimethylaminopyridine, DBU, NaH and KR. The mole ratio of YC(O)$R^{18}$ to base is typically about 1:1 to 1:4.

In another embodiment, provided is a method of preparing a compound of Formula H wherein $R^{16}$ is OH,
the method comprising:
(e) providing a compound of Formula II:

Formula III

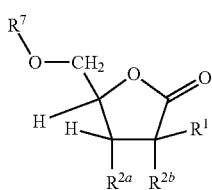

(f) treating the compound of Formula III with an organometallic compound of Formula IV:

Formula IV

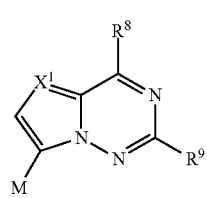

wherein M is Mg$X^3$ or Li and $X^3$ is halogen;
thereby forming a compound of Formula II wherein $R^{16}$ is OH;

provided that when M is Li, the compound of Formula II is not a compound of Formula VII Formula VII

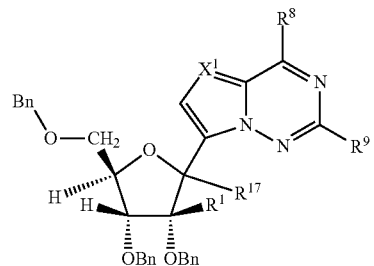

wherein $R^{17}$ is OH; and
(a) $X^1$ is CH, $R^1$ is $CH_3$, $R^8$ is $NH_2$ and $R^9$ is $NH_2$ or H; or
(b) $X^1$ is CH, $R^1$ is $CH_3$, $R^8$ is OH and $R^9$ is $NH_2$; or
(c) $X^1$ is CH, each $R^1$ and $R^9$ is H and $R^8$ is $NH_2$; or
(d) $X^1$ is N, $R^1$ is $CH_3$, $R^8$ is $NH_2$, and $R^9$ is H, $NH_2$ or $SCH_3$; or
(e) $X^1$ is N, $R^1$ is $CH_3$, $R^8$ is $SCH_3$ or $NHCH_3$, and $R^9$ is $SCH_3$; or
(f) $X^1$ is N, $R^1$ is $CH_3$, $R^8$ is $OCH_3$, and $R^9$ is $SCH_3$, $SO_2CH_3$ or $NH_2$.

In another embodiment of the method of preparing a compound of Formula II wherein $R^{16}$ is OH, the compound of Formula II is Formula IIb wherein $R^{16}$ is OH and the compound of Formula III is a compound of Formula IIIb:

Formula IIIb

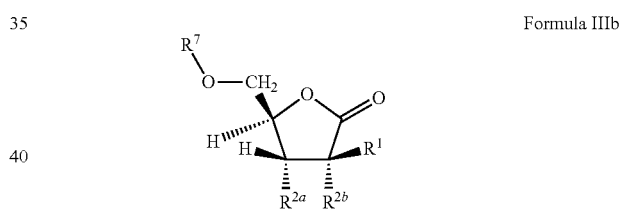

provided that when M is Li, the compound of Formula IIb is not a compound of Formula VII Formula VII

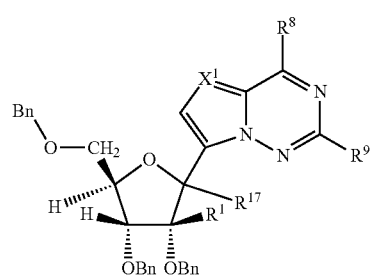

wherein $R^{17}$ is OH; and
(a) $X^1$ is CH, $R^1$ is $CH_3$, $R^8$ is $NH_2$ and $R^9$ is $NH_2$ or H; or
(b) $X^1$ is CH, $R^1$ is $CH_3$, $R^8$ is OH and $R^9$ is $NH_2$; or
(c) $X^1$ is CH, each $R^1$ and $R^9$ is H and $R^8$ is $NH_2$; or
(d) $X^1$ is N, $R^1$ is $CH_3$, $R^8$ is $NH_2$, and $R^9$ is H, $NH_2$ or $SCH_3$; or (e) $X^1$ is N, $R^1$ is $CH_3$, $R^8$ is $SCH_3$ or $NHCH_3$, and $R^9$ is $SCH_3$; or (f) $X^1$ is N, $R^1$ is $CH_3$, $R^8$ is $OCH_3$, and $R^9$ is $SCH_3$, $SO_2CH_3$ or $NH_2$.

The following are additional independent aspects of this embodiment:

(a) $R^1$ is H. $R^1$ is $CH_3$.

(b) $R^{2b}$ is $OR^4$. $R^{2b}$ is F. Each $R^{2a}$ and $R^{2b}$ is independently $OR^4$. $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is OH. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are $—C(R^{19})_2—$. Each $R^{2a}$ and $R^{2b}$ is $OR^4$ wherein the two $R^4$ taken together are $—C(CH_3)_2—$. Each $R^{2a}$ and $R^{2b}$ is $OR^4$ wherein the two $R^4$ taken together are $—CH(R^{19})—$. Each $R^{2a}$ and $R^{2b}$ is $OR^4$ wherein the two $R^4$ taken together are $—CH(R^{19})—$ wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.

(c) $R^7$ is $C(O)R^5$. $R^7$ is H. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $—C(CH_3)_2—$. $R^7$ is $Si(R^3)_3$ and each $R^{2a}$ and $R^{2b}$ is $OR^4$ wherein the two $R^4$ taken together are $—C(CH_3)_2—$. $R^7$ is $Si(R^3)_2$(t-butyl) wherein each $R^3$ is $CH_3$ and each $R^{2a}$ and $R^{2b}$ is $OR^4$ wherein the two $R^4$ taken together are $—C(CH_3)_2—$. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are $—C(CH_3)_2—$. $R^7$ is tetrahydro-2H-pyran-2-yl and each $R^{2a}$ and $R^{2b}$ is $OR^4$ wherein the two $R^4$ taken together are $—C(CH_3)_2—$. $R^7$ is $C(O)R^5$ and each $R^{2a}$ and $R^{2b}$ is $OR^4$ wherein the two $R^4$ taken together are $—C(CH_3)_2—$. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $—CH(R^{19})—$ wherein $R^{19}$ is phenyl or substituted phenyl. $R^7$ is $Si(R^3)_3$ and each $R^{2a}$ and $R^{2b}$ is $OR^4$ wherein the two $R^4$ taken together are $—CH(R^{19})—$ wherein $R^{19}$ is phenyl or substituted phenyl. $R^7$ is $Si(R^3)_2$(t-butyl) wherein each $R^3$ is $CH_3$ and each $R^{2a}$ and $R^{2b}$ is $OR^4$ wherein the two $R^4$ taken together are $—CH(R^{19})—$ wherein $R^{19}$ is phenyl or substituted phenyl. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are $—CH(R^{19})—$ wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are $—CH(R^{19})—$ wherein $R^{19}$ is phenyl or substituted phenyl. $R^7$ is $C(O)R^5$ and each $R^{2a}$ and $R^{2b}$ is $OR^4$ wherein the two $R^4$ taken together are $—CH(R^{19})—$ wherein $R^{19}$ is phenyl or substituted phenyl. $R^7$ is $C(O)R^5$ wherein $R^5$ is phenyl or substituted phenyl and $R^{2b}$ is F.

(d) $X^1$ is $C—R^{10}$. $X^1$ is $C—H$. $X^1$ is N.

(e) $R^8$ is $NR^{11}R^{12}$. $R^8$ is $OR^{11}$. $R^8$ is $SR^{11}$.

(f) $R^9$ is H. $R^9$ is $NR^{11}R^{12}$. $R^9$ is $SR^{11}$.

(g) Each $R^{11}$ or $R^{12}$ is independently $(C_1-C_8)$alkyl, $—C(=O)(C_1-C_8)$alkyl, $—S(O)_n(C_1-C_8)$alkyl, aryl$(C_1-C_8)$alkyl or $Si(R^3)_3$; or $R^{11}$ and $R^{12}$ taken together with a nitrogen to which they are both attached form a 3 to 7 membered heterocyclic ring; or $R^{11}$ and $R^{12}$ taken together are $—Si(R^3)_2(X^2)_mSi(R^3)_2—$. Each $R^{11}$ or $R^{12}$ is independently $(C_1-C_8)$alkyl. Each $R^{11}$ or $R^{12}$ is independently $Si(R^3)_3$. Each $R^{11}$ or $R^{12}$ is independently $Si(R^3)_3$ wherein at least two of $R^3$ are $CH_3$ or phenyl. Each $R^{11}$ or $R^{12}$ is independently $Si(CH_3)_3$. Each $R^{11}$ and $R^{12}$ of $NR^{11}R^{12}$ is independently selected from $Si(R^3)_3$ or $R^{11}$ and $R^{12}$ of $NR^{11}R^{12}$ taken together are $—Si(R^3)_2(X^2)_mSi(R^3)_2—$. Each $R^{11}$ and $R^{12}$ of $NR^{11}R^{12}$ is independently selected from $Si(R^3)_3$ or $R^{11}$ and $R^{12}$ of $NR^{11}R^{12}$ taken together are $—Si(R^3)_2(X^2)_mSi(R^3)_2—$; and each $R^3$ is methyl.

(h) M is $MgX^3$. M is Li.

In another embodiment of the method of preparing a compound of Formula IIb wherein $R^{16}$ is OH, the compound of Formula IIb is Formula IIc and the compound of Formula IIIb is a compound of Formula Inc:

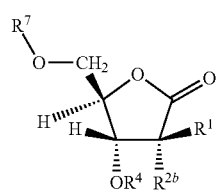

Formula IIIc provided that when M is Li, the compound of Formula IIe is not a compound of Formula VII

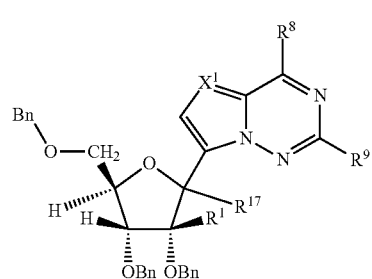

Formula VII wherein $R^{17}$ is OH; and (a) $X^1$ is CH, $R^1$ is $CH_3$, $R^8$ is $NH_2$ and $R^9$ is $NH_2$ or H; or (b) $X^1$ is CH, $R^1$ is $CH_3$, $R^8$ is OH and $R^9$ is $NH_2$; or (c) $X^1$ is CH, each $R^1$ and $R^9$ is H and $R^8$ is $NH_2$; or (d) $X^1$ is N, $R^1$ is $CH_3$, $R^8$ is $NH_2$, and $R^9$ is H, NH, or $SCH_3$; or (e) $X^1$ is N, $R^1$ is $CH_3$, $R^8$ is $SCH_3$ or $NHCH_3$, and $R^9$ is $SCH_3$; or (f) $X^1$ is N, $R^1$ is $CH_3$, $R^8$ is $OCH_3$, and $R^9$ is $SCH_3$, $SO_2CH_3$ or $NH_2$.

The following are additional independent aspects of this embodiment:

(a) $R^1$ is H. $R^1$ is $CH_3$.

(b) $R^{2b}$ is $OR^4$. $R^{2b}$ is F. $R^{2b}$ is F and $R^4$ is $C(O)R^5$. $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $OR^4$ and $R^{2b}$ is OH. $R^{2b}$ is $OR^4$ wherein each $R^4$ is independently $C(R^5)_2R^6$ and $R^6$ is phenyl or substituted phenyl. $R^{2b}$ is $OR^4$ wherein each $R^4$ is $CH_2R^6$ and $R^6$ is phenyl. $R^{2b}$ is $OR^4$ wherein each $R^4$ is $CH_2R^6$ and each $R^6$ is independently substituted phenyl. $R^{2b}$ is $OR^4$ wherein the two $R^4$ taken together are $-C(R^{19})_2-$. $R^{2b}$ is $OR^4$ wherein the two $R^4$ taken together are $-C(CH_3)_2-$. $R^{2b}$ is $OR^4$ wherein the two $R^4$ taken together are $-CH(R^{19})-$. $R^{2b}$ is $OR^4$ wherein the two $R^4$ taken together are $-CH(R^{19})-$ wherein $R^{19}$ is phenyl or substituted phenyl. $R^4$ is $C(R^5)_2R^6$, $R^6$ is phenyl or substituted phenyl and $R^{2b}$ is F.

(c) $R^7$ is $C(O)R^5$. $R^7$ is H. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and $R^{2b}$ is $OR^4$ wherein the two $R^4$ taken together are $-C(CH_3)_2-$. $R^7$ is $Si(R^3)_3$ and $R^{2b}$ is $OR^4$ wherein the two $R^4$ taken together are $-C(CH_3)_2-$. $R^7$ is $Si(R^3)_2$(t-butyl) wherein each $R^3$ is $CH_3$ and $R^{2b}$ is $OR^4$ wherein the two $R^4$ taken together are $-C(CH_3)_2-$. $R^7$ is $Si(R^3)_2$(t-butyl) wherein each $R^3$ is independently phenyl or substituted phenyl and $R^{2b}$ is $OR^4$ wherein the two $R^4$ taken together are $-C(CH_3)_2-$. $R^7$ is tetrahydro-2H-pyran-2-yl and $R^{2b}$ is $OR^4$ wherein the two $R^4$ taken together are $-C(CH_3)_2-$. $R^7$ is $C(O)R^5$ and $R^{2b}$ is $OR^4$ wherein the two $R^4$ taken together are $-C(CH_3)_2-$. $R^7$ is $C(R^5)_2R^6$ wherein each $R^5$ and $R^6$ is independently phenyl or substituted phenyl and $R^{2b}$ is $OR^4$ wherein the two $R^4$ taken together are $-CH(R^{19})-$ wherein $R^{19}$ is phenyl or substituted phenyl. $R^7$ is $Si(R^3)_3$ and $R^{2b}$ is $OR^4$ wherein the two $R^4$ taken together are $-CH(R^{19})-$ wherein $R^{19}$ is phenyl or substituted phenyl. $R^7$ is $Si(R^3)_2$(t-butyl) wherein each $R^3$ is $CH_3$ and $R^{2b}$ is $OR^4$ wherein the two $R^4$ taken together are $-CH(R^{19})-$ wherein $R^{19}$ is phenyl or substituted phenyl. $R^7$ is $Si(R^3)_2$(t-butyl) wherein each $R^3$ is independently phenyl or substituted phenyl and $R^{2b}$ is $OR^4$ wherein the two $R^4$ taken together are $-CH(R^{19})-$ wherein $R^{19}$ is phenyl or substituted phenyl. $R^7$ is tetrahydro-2H-pyran-2-yl and $R^{2b}$ is $OR^4$ wherein the two $R^4$ taken together are $-CH(R^{19})-$ wherein $R^{19}$ is phenyl or substituted phenyl. $R^7$ is $C(O)R^5$ and $R^{2b}$ is $OR^4$ wherein the two $R^4$ taken together are $-CH(R^{19})-$ wherein $R^{19}$ is phenyl or substituted phenyl. $R^7$ is $C(O)R^5$ wherein $R^5$ is phenyl or substituted phenyl and $R^{2b}$ is F.

(d) $X^1$ is $C-R^{10}$. $X^1$ is $C-H$. $X^1$ is N.

(e) $R^8$ is $NR^{11}R^{12}$. $R^8$ is $OR^{11}$. $R^8$ is $SR^{11}$.

(f) $R^9$ is H. $R^9$ is $NR^{11}R^{12}$. $R^9$ is $SR^{11}$.

(g) Each $R^{11}$ or $R^{12}$ is independently $(C_1-C_8)$alkyl, $-C(=O)(C_1-C_8)$alkyl, $-S(O)_n(C_1-C_8)$alkyl, aryl$(C_1-C_8)$alkyl or $Si(R^3)_3$; or $R^{11}$ and $R^{12}$ taken together nitrogen to which they are both attached form a 3 to 7 membered heterocyclic ring; or $R^{11}$ and $R^{12}$ taken together are $-Si(R^3)_2(X^2)_mSi(R^3)_2-$. Each $R^{11}$ or $R^{12}$ is independently $(C_1-C_8)$alkyl. Each $R^{11}$ or $R^{12}$ is independently $Si(R^3)_3$. Each $R^{11}$ or $R^{12}$ is independently $Si(R^3)_3$ wherein at least two of $R^3$ are $CH_3$ or phenyl. Each $R^{11}$ or $R^{12}$ is independently $Si(CH_3)_3$. Each $R^{11}$ and $R^{12}$ of $NR^{11}R^{12}$ is independently selected from $Si(R^3)_3$ or $R^{11}$ and $R^{12}$ taken together are $-Si(R^3)_2(X^2)_mSi(R^3)_2-$. Each $R^{11}$ and $R^{12}$ of $NR^{11}R^{12}$ is independently selected from $Si(R^3)_3$ or $R^{11}$ and $R^{12}$ of $NR^{11}R^{12}$ taken together are $-Si(R^3)_2(X^2)_mSi(R^3)_2-$; and each $R^3$ is methyl.

(h) M is $MgX^3$. M is Li.

In another embodiment, the method of preparing a compound of Formula I further comprises the method of preparing a compound of Formula II wherein $R^{16}$ is OH.

In another embodiment, the method of preparing a compound of Formula Ib further comprises a method for preparing the compound of Formula III wherein $R^{16}$ is OH.

In another embodiment, the method of preparing a compound of Formula Ic further comprises the method for preparing a compound of Formula IIc wherein $R^{16}$ is OH.

Typically, the method of preparing a compound of Formula II, IIb or IIc wherein $R^{16}$ is OH from a compound of Formula III, IIIb or IIIc, respectively, is performed in a suitable aprotic solvent at about −100 to about to abut 50° C. for about 5 minutes to 24 hours. Non-limiting examples of suitable aprotic solvents include THF, dioxane and ether. More typically, the suitable solvent is THF and the preferred temperature is about −78 to 0° C. The mole ratio of the compound of Formula IV to the compound of Formula III, IIIb or IIIc is about 1:2 to 2:1; preferably about 1:1.

In another embodiment, the method of preparing a compound of Formula II, IIb or IIc wherein $R^{16}$ is OH from a compound of Formula III, IIIb or IIIc, respectively, further comprises a method of preparing a compound of Formula IV wherein M is $MgX^3$ or Li and $X^3$ is halogen, the method comprising:

(g) providing a compound of Formula V:

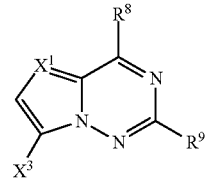

Formula V wherein $X^3$ is Cl, Br or I and (h) treating the compound of Formula V with an organometallic reagent comprising an organomagnesium or organolithium compound;

thereby forming a compound of Formula IV.

In another embodiment, the method of preparing a compound of Formula IV from a compound of Formula V comprises the following independent aspects:

(a) $X^1$ is $C-R^{10}$. $X^1$ is $C-H$. $X^1$ is N.

(b) $R^8$ is $NR^{11}R^{12}$. $R^8$ is $OR^{11}$. $R^8$ is $SR^{11}$.

(c) $R^9$ is H. $R^9$ is $NR^{11}R^{12}$. $R^9$ is $SR^{11}$.

(d) Each $R^{11}$ or $R^{12}$ is independently $(C_1-C_8)$alkyl, $-C(=O)(C_1-C_8)$alkyl, $-S(O)_n(C_1-C_8)$alkyl, aryl$(C_1-C_8)$alkyl or $Si(R^3)_3$; or $R^{11}$ and $R^{12}$ taken together with a nitrogen to which they are both attached form a 3 to 7 membered heterocyclic ring; or $R^{11}$ and $R^{12}$ taken together are $-Si(R^3)_2(X^2)_mSi(R^3)_2-$. Each $R^{11}$ or $R^{12}$ is independently $(C_1-C_8)$alkyl. Each $R^{11}$ or $R^{12}$ is independently $Si(R^3)_3$. Each $R^{11}$ or $R^{12}$ is independently $Si(R^3)_3$ wherein at least two of $R^3$ are $CH_3$ or phenyl. Each $R^{11}$ or $R^{12}$ is independently $Si(CH_3)_3$. Each $R^{11}$ and $R^{12}$ of $NR^{11}R^{12}$ is independently selected from $Si(R^3)_3$ or $R^{11}$ and $R^{12}$ of $NR^{11}R^{12}$ taken together are $-Si(R^3)_2(X^2)_mSi(R^3)_2-$. Each $R^{11}$ and $R^{12}$ of $NR^{11}R^{12}$ is independently selected from $Si(R^3)_3$ or $R^{11}$ and $R^{12}$ of $NR^{11}R^{12}$ taken together are $-Si(R^3)_2(X^2)_mSi(R^3)_2-$; and each $R^3$ is methyl.

(e) $X^3$ is Cl. $X^3$ is Br. $X^3$ is I.

In one embodiment, the method of preparing a compound of Formula IV comprises treating a compound of Formula V with a organomagnesium compound. Typically, the transmetalation reaction is performed in a suitable aprotic solvent at about −78 to about to abut 50° C. for about 5 minutes to 24 hours. Non-limiting examples of suitable aprotic solvents include THF, dioxane and ether. In one embodiment, the mole ratio of the compound of Formula V to organomagnesium compound is about 1:1 to about 1:3, preferably about 1:2. In one embodiment, the organomagnesium compound comprises an alkylmagnesium chloride, bromide, or iodide. In another embodiment, the organomagnesium compound comprises 2-propylmagnesium chloride. In one embodiment, the organomagnesium compound comprises an alkylmagnesium chloride, bromide, or iodide and lithium chloride. In another embodiment, the organomagnesium compound comprises 2-propylmagnesium chloride and lithium chloride. In another embodiment, the organomagnesium compound is 2-propylmagnesium choride and lithium choride in about a 1:1 mole ratio. In a preferred embodiment, the organomagnesium compound comprises 2-propylmagnesium chloride and lithium chloride in a 1:1 mole ratio and the $X^3$ of Formula V is Br or I.

In another aspect wherein the compound of Formula IV is prepared by treating a compound of Formula V with a organomagnesium compound, the compound of Formula V may be treated with more than one organomagnesium compound. This procedure would be preferable when the compound of Formula V comprises a substituent with an acidic hydrogen. Non-limiting examples of the substituents with acidic hydrogens are $NH_2$, OH, SH, $NH(C_1-C_6$ alkyl) and the like. One skilled in the art will recognize that the acidic hydrogen group of the substituent of the compound of Formula V will consume one mole equivalent of the organomagnesium compound. The organomagnesium compound consumed may be different from the organomagnesium compound that produces the transmetalation reaction. For example, but not by way of limitation, treating the compound of Formula V with about one mole equivalent of methylmagnesium chloride would neutralize an acidic hydrogen of $NH(C_1-C_6$ alkyl), OH, or SH substituent by forming a magnesium salt and the $X^3$ group (Cl, Br, or I group) of the compound of Formula V may be transmetalated with another organomagnesium compound such as 2-propylmagnesium chloride or 2-propylmagnesium chloride and lithium chloride. Similarly, if additional acidic hydrogens are present, an additional about equivalent amount of organomagnesium compound would be required to neutralize each additional acidic hydrogen, e.g., each additional $NH_2$ substituent would require about two additional equivalents of organomagnesium compound. Typically, the transmetalation reactions of this aspect are performed in a suitable aprotic solvent at about −78 to about to abut 50° C. for about 5 minutes to 24 hours. Non-limiting examples of suitable aprotic solvents include THF, dioxane and ether. In one embodiment, the compound of Formula IV is prepared by treating the compound of Formula V with about one mole equivalent of a first organomagnesium compound for each acidic hydrogen in a substitutent followed by treatment with a second organomagnesium compound to transmetallate the $X^3$ group of Formula V. In one embodiment, the mole ratio of the first organomagnesium compound to each acid hydrogen in a substituent of a molecule of Formula V is about 1:1 to about 1:1.4 and the mole ratio of the second organomagnesium compound to the compound of Formula V is about 1:0.8 to about 1:2. In one embodiment, the first organomagnesium compound comprises an alkylmagnesium chloride, bromide, or iodide. In another embodiment, the first organomagnesium compound comprises methylmagnesium chloride. In another embodiment, the second organomagnesium compound comprises an alkylmagnesium chloride, bromide, or iodide. In another embodiment, the second alkylmagnesium compound comprises 2-propylmagnesium chloride. In one embodiment, the second organomagnesium compound comprises an alkylmagnesium chloride, bromide, or iodide and lithium chloride. In another embodiment the second organomagnesium compound is 2-propylmagnesium chloride and lithium chloride in a 1:1 mole ratio. In a preferred embodiment, the first organornagnesium compound is methylmagnesiurn chloride and the second organomagnesium compound comprises 2-propylmagnesium chloride. In another preferred embodiment the first organomagnesium compound is methylmagnesium chloride and the second organomagnesium compound is 2-propylmagnesium chloride and lithium chloride in a 1:1 mole ratio. In another preferred embodiment the first organomagnesium compound is methylmagnesium chloride, the second organomagnesium compound is 2-propylmagnesium chloride and lithium chloride in about 1:1 mole ratio, and the $X^3$ of Formula V is Br or I. In another preferred embodiment the first organomagnesium compound is methylmagnesium chloride, the second organomagnesium compound is 2-propylmagnesium chloride and lithium chloride in about 1:1 mole ratio, the $X^3$ of Formula V is Br or I. and $R^8$ is $NH_2$.

The magnesium salts of the substituents of Formula V discussed above may be converted to a protected form of the substituent such as, but not limited to, a silyl protected substituent. Subsequently, the $X^3$ group (Cl, Br, or I group) of the compound of Formula V may be transmetalated with the same or a different organomagnesium compound such as 2-propylmagnesium chloride or 2-propylmagnesium chloride and lithium chloride. Similarly, if additional acidic hydrogens are present, an additional about one equivalent amount of organomagnesium compound would be required to neutralize each additional acidic hydrogen, e.g., each additional $NH_2$ substituent would require about two additional equivalents of organomagnesium compound and the resulting magnesium salts could be converted to protecting groups, such as but not limited to, silyl protecting groups. Non-limiting examples of the resulting protected substituents would be $OSi(R^3)_3$, $SSi(R^3)_3$, $N[Si(R^3)_3][C_1-C_6$ alkyl], $N[Si(R^3)_2(CH_2)_2Si(R^3)_2]$ and $N[Si(R^3)]_2$. All such intermediates with protected substituents are within the scope of the instant invention. Non-limiting examples of silylating reagents to convert the intermediate magnesium salt of the substituents to protected substituents include $X^3Si(R^3)_3$, $X^3Si(R^3)_2(CH_2)_2Si(R^3)_2X^3$ and $(R^{20})_3CS(O)_2OSi(R^3)_3$, more specifically $ClSi(R^3)_3$, $ClSi(R^3)_2(CH_2)_2Si(R^3)_2Cl$ and $CF_3S(O)_2OSi(R^3)_3$; and most specifically $ClSi(CH_3)_3$, $ClSi(CH_3)_2(CH_2)_2Si(CH_3)_2Cl$ and $CF_3S(O)_2OSi(CH_3)_3$. These silylating reagents may be present before the addition of the initial organometallic agent if the temperature of the reaction is sufficiently controlled or they may be added after conversion of the substituent to the magnesium salt.

Typically, the conversion of substituents of Formula V with acidic hydrogens to protected substituents are performed in a suitable aprotic solvent at about −78 to about to abut 50° C. for about 5 minutes to 24 hours. Non-limiting examples of suitable aprotic solvents include THF, dioxane and ether.

In one embodiment, the compound of Formula IV is prepared by treating the compound of Formula V comprising substituents with acidic hydrogens with about one mole equivalent of a first organomagnesium compound for each acidic hydrogen in a substitutent, treatment with about 1-1.4 equivalents of protecting group reagent for each acid hydrogen, and treatment with 1-2 equivalents of the same or a different organomagnesium compound to transmetallate the $X^3$ group of Formula V.

In another embodiment, the compound of Formula IV is prepared by treating a mixture of compound of Formula V and about 1-1.4 equivalents of protecting group reagent per acidic hydrogen in Formula V with about 1-1.4 equivalents of a first organomagnesium compound for each acid hydrogen in a substitutent, followed by treatment with 1-2 equivalents of the same or a different organomagnesium compound to transmetallate the $X^3$ group of Formula V.

In another embodiment, the compound of Formula IV is prepared by treating a mixture of compound of Formula V and about 1-1.4 equivalents of protecting reagent per acidic hydrogen in Formula V with about 1-1.4 equivalents of a organomagnesium compound for each acid hydrogen in a substitutent and an additional 1-2 equivalents of organomagnesium compound to transmetallate the $X^3$ group of Formula V. In another aspect of this embodiment, the $X^3$ of Formula V is Br or I and $R^8$ of Formula V is NH—.

In another embodiment, the method of preparing a compound of Formula I or Formula Ib further comprises a method of preparing a compound of Formula IV wherein M is Li by treating a compound of Formula V with an organolithium compound. Typically, the transmetalation reaction is performed in a suitable aprotic solvent at about −100 to about to abut 20° C. for about 5 minutes to 24 hours. Non-limiting examples of suitable aprotic solvents include THF and ether. In one aspect of this embodiment, the mole ratio of the compound of Formula V to organolithium compound is about 1:1 to about 1:3, preferably about 1:1.4. In another aspect of this embodiment, the organolithium compound comprises an alkyllithium compound. In another aspect of this embodiment, the organolithium compound comprises n-butyllithium. In another aspect of this embodiment, the organolithium compound comprises iso-butyllithium. In another aspect of this embodiment, the organolithium compound comprises tert-butyllithium. In a preferred aspect of this embodiment, the organolithium compound comprises an alkyllithium compound and the $X^3$ of Formula V is Br or I.

In another embodiment wherein the compound of Formula IV is prepared by treating a compound of Formula V with an organolithium compound, the compound of Formula V may be treated with more than one mole equivalent of organolithium compound. This procedure would be preferable when the compound of Formula V is comprised of a substituent with an acidic hydrogen. Non-limiting examples of the substituents with acidic hydrogens are $NH_2$, OH, SH, $NH(C_1-C_6$ alkyl) and the like. One skilled in the art will recognize that the acidic hydrogen group of the substituent of the compound of Formula V will consume one mole equivalent of the organolithium compound. For example, but not by way of limitation, treating the compound of Formula V with about one mole equivalent of organolithium compound would neutralize an acidic hydrogen of $NH(C_1-C_6$ alkyl), OH, or SH substituent by forming a lithium salt and the $X^3$ group (Cl, Br, or I group) of the compound of Formula V may be transmetalated with another mole equivalent of organolithium compound. Similarly, if additional acidic hydrogens are present, an additional about equivalent amount of organolithium compound would be required to neutralize each additional acidic hydrogen, e.g., each additional $NH$ substituent would require about two additional equivalents of organolithium compound. Typically, the transmetalation reactions of this aspect are performed in a suitable aprotic solvent at about −100 to about to abut 20° C. for about 5 minutes to 24 hours. Non-limiting examples of suitable aprotic solvents include THF, dioxane and ether. In one embodiment, the mole ratio of the organolithium compound to the each acid hydrogen in a substituent of a molecule of Formula V is about 1:1 to about 1:1.4 and the mole ratio of the additional amount of organolithium compound to the compound of Formula V is about 1:0.8 to about 1:1.4. In another aspect of this embodiment, the organolithium compound comprises an alkyllithium compound. In another embodiment, the organolithium compound comprises n-butyllithium. In another embodiment, the organolithium compound comprises iso-butyllithium. In another embodiment, the organolithium compound comprises tert-butyllithium. In a preferred embodiment, the organolithium compound comprises a $(C_1-C_6)$alkyllithium compound and the $X^3$ of Formula V is Br or I.

The lithium salts of the substituents of Formula V discussed above may be converted to a protected form of the substituent such as, but not limited to, a silyl protected substituent. Subsequently, the $X^3$ group (Cl, Br, or I group) of the compound of Formula V may be transmetalated with the same or a different organolithium compound. Similarly, if additional acidic hydrogens are present, an additional about one equivalent amount of organolithium compound would be required to neutralize each additional acidic hydrogen, e.g., each additional $NH_2$ substituent would require about two additional equivalents of organolithium compound and the resulting lithium salts could be converted to protecting groups, such as but not limited to, silyl protecting groups. Non-limiting examples of the resulting protected substituents would be $OSi(R^3)_3$, $SSi(R^3)_3$, $N[Si(R^3)_3][C_1-C_6$ alkyl], $N[Si(R^3)_2(CH_2)_2Si(R^3)_2]$ and $N[Si(R^3)_3]_2$. All such intermediates with protected substituents are within the scope of the instant invention. Non-limiting examples of silylating reagents to convert the intermediate lithium salt of the substituents to protected substituents include $X^3Si(R^3)_3$, $X^3Si(R^3)_2(CH_2)_2Si(R^3)_2X^3$ and $(R^{20})_3CS(O)_2OSi(R^3)_3$ more specifically $ClSi(R^3)_3$, $ClSi(R^3)_2(CH_2)_2Si(R^3)_2Cl$ and $CF_3S(O)_2OSi(R^3)_3$, and most specifically $ClSi(CH_3)_3$, $ClSi(CH_3)_2(CH_2)_2Si(CH_3)_2Cl$ and $CF_3S(O)_2OSi(CH_3)_3$. These silylating reagents may be present before the addition of the initial organometallic agent if the temperature of the reaction is sufficiently controlled or they may be added after conversion of the substituent to the lithium salt.

Typically, the conversion of substituents of Formula V with acid hydrogens to protected substituents are performed in a suitable aprotic solvent at about −100 to about to abut 20° C. for about 5 minutes to 24 hours. Non-limiting examples of suitable aprotic solvents include THF, dioxane and ether.

In one embodiment, the compound of Formula IV is prepared by treating the compound of Formula V comprising substituents with acid hydrogens with about 1-1.4 mole equivalent of a organolithium compound for each acid hydrogen in a substitutent, treatment with about 1-1.4 equivalents of protecting group reagent for each acid hydrogen, and treatment with 1-1.4 equivalents of the same or a different organolithium compound to transmetallate the $X^3$ group of Formula V.

In another embodiment, the compound of Formula IV is prepared by treating a mixture of compound of Formula V and about 1-1.4 equivalents of protecting group reagent per acidic hydrogen in Formula V with about 1-1.4 equivalents of a first organolithium compound for each acid hydrogen in a substitutent, followed by treatment with 1-1.4 equivalents of the same or a different organolithium compound to transmetallate the $X^3$ group of Formula V.

In another embodiment, the compound of Formula IV is prepared by treating a mixture of compound of Formula V and about 1-1.4 equivalents of protecting reagent per acidic hydrogen in Formula V with about 1-1.4 equivalents of a organolithium compound for each acid hydrogen in a substitutent and an additional 1-1.4 equivalents of organolithium compound to transmetallate the $X^3$ group of Formula V. In another aspect of this embodiment, the $X^3$ of Formula V is Br or I. and $R^8$ of Formula V is $NH_2$. In another aspect of this embodiment, the organolithium compound comprises an alkyllithium compound. In another embodiment, the organolithium compound comprises n-butyllithium. In another embodiment, the organolithium compound comprises iso-butyllithium. In another embodiment, the organolithium compound comprises tert-butyllithium. In a preferred embodiment, the organolithium compound comprises a $(C_1-C_6)$alkyllithium compound and the $X^3$ of Formula V is Br or I. In another embodiment, the protecting group reagent is a silylating reagent. In another embodiment, the protecting group reagent is $X^3Si(R^3)_3$ or $(R^{20})_3CS(O)_2OSi(R^3)_3$. In another embodiment, the protecting group reagent is $ClSi(R^3)_3$ or $CF_3S(O)_2OSi(R^3)_3$. In another embodiment, the protecting group reagent is $ClSi(CH_3)_3$ or $CF_3S(O)_2OSi(CH_3)_3$.

In another embodiment, provided are useful intermediates for the syntheses of compounds of Formula I represented by Formula VI. In one embodiment, $R^{17}$ is OH. In another embodiment, $R^{17}$ is $-OC(O)R^{18}$. In another embodiment, $R^{17}$ is $-OC(O)OR^{18}$. In another embodiment, $R^{17}$ is $OR^{18}$.

In another embodiment, provided is a compound of Formula IIb represented by Formula VIb:

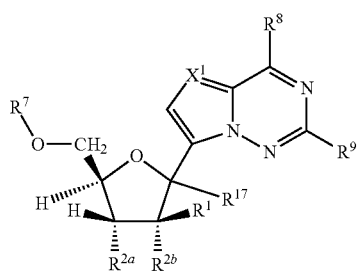

Formula VIb or an acceptable salt, thereof;
wherein the variables are defined as for Formula VI.

In one embodiment of the compound of Formula VIb, $R^{17}$ is OH. The following are additional independent aspects of this embodiment:

(a) $R^1$ is H. $R^1$ is $CH_3$.
(b) $X^1$ is C—$R^{10}$. $X^1$ is C—H. $X^1$ is N.
(c) $R^8$ is $NR^{11}R^{12}$. $R^8$ is $OR^{11}$. $R^8$ is $SR^{11}$.
(d) $R^9$ is H. $R^9$ is $NR^{11}R^{12}$. $R^9$ is $SR^{11}$.
(e) $R^{2b}$ is $OR^4$. $R^{2b}$ is F. Each $R^{2a}$ and $R^{2b}$ is independently $OR^4$. $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are $-C(R^{19})_2-$. Each $R^{2a}$ and $R^{2b}$ is $OR^4$ wherein the two $R^4$ taken together are $-C(CH_3)_2-$. Each $R^{2a}$ and $R^{2b}$ is $OR^4$ wherein the two $R^4$ taken together are $-CH(R^{19})-$. Each $R^{2a}$ and $R^{2b}$ is $OR^4$ wherein the two $R^4$ taken together are $-CH(R^{19})-$ wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.

(f) $R^7$ is $C(O)R^5$. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $-C(CH_3)_2-$. $R^7$ is $Si(R^3)_3$ and each $R^{2a}$ and $R^{2b}$ is $OR^4$ wherein the two $R^4$ taken together are $-C(CH_3)_2-$. $R^7$ is $Si(R^3)_2$(t-butyl) wherein each $R^3$ is $CH_3$ and each $R^{2a}$ and $R^{2b}$ is $OR^4$ wherein the two $R^4$ taken together are $-C(CH_3)_2-$. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are $-C(CH_3)_2-$. $R^7$ is tetrahydro-2H-pyran-2-yl and each $R^{2a}$ and $R^{2b}$ is $OR^4$ wherein the two $R^4$ taken together are $-C(CH_3)_2-$. $R^7$ is $C(O)R^5$ and each $R^{2a}$ and $R^{2b}$ is $OR^4$ wherein the two $R^4$ taken together are $-C(CH_3)_2-$. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $Si(R^3)_3$ and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $Si(R^3)_2$(t-butyl) wherein each $R^3$ is $CH_3$ and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are $-CH(R^{19})-$ wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $C(O)R^5$ and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $C(O)R^5$ wherein $R^5$ is phenyl or substituted phenyl and $R^{2b}$ is F.

(g) $R^1$ is H, $X^1$ is CH, and $R^8$ is $NR^{11}R^{12}$. $R^1$ is H, $X^1$ is CH, and $R^8$ is $NH_2$. $R^1$ is $CH_3$, $X^1$ is CH, and $R^8$ is $NR^{11}R^{12}$. $R^1$ is $CH_3$, $X^1$ is CH, and $R^8$ is $NH_2$. $R^1$ is H, $X^1$ is N, and $R^8$ is $NR^{11}R^{12}$. $R^1$ is H, $X^1$ is N, and $R^8$ is $NH_2$. $R^1$ is $CH_3$, $X^1$ is N, and $R^8$ is $NR^{11}R^{12}$. $R^1$ is $CH_3$, $X^1$ is N, and $R^8$ is $NH_2$. $R^1$ is H, $X^1$ is CH, and $R^9$ is $NR^{11}R^{12}$. $R^1$ is H, $X^1$ is CH, and $R^9$ is $NH_2$. $R^1$ is H, $X^1$ is CH, and $R^9$ is $SR^{11}$. $R^1$ is H, $X^1$ is CH, and $R^9$ is SH. $R^1$ is H, is CH, and $R^9$ is H. $R^1$ is $CH_3$, $X^1$ is CH, and $R^9$ is $NR^{11}R^{12}$. $R^1$ is $CH_3$, $X^1$ is CH, and $R^9$ is $NH_2$. $R^1$ is $CH_3$, $X^1$ is CH, and $R^9$ is $SR^{11}$. $R^1$ is $CH_3$, $X^1$ is CH, and $R^9$ is SH. $R^1$ is $CH_3$, $X^1$ is CH, and $R^9$ is H.

(h) $R^1$ is H, $X^1$ is CH, and $R^8$ is $OR^{11}$. $R^1$ is H, $X^1$ is CH, and $R^8$ is OH. $R^1$ is $CH_3$, $X^1$ is CH, and $R^8$ is $OR^{11}$. $R^1$ is $CH_3$, $X^1$ is CH, and $R^8$ is OH. $R^1$ is H, $X^1$ is N, and $R^8$ is $OR^{11}$. $R^1$ is H, $X^1$ is N, and $R^8$ is OH. $R^1$ is $CH_3$, $X^1$ is N, and $R^8$ is $OR^{11}$. $R^1$ is $CH_3$, $X^1$ is N, and $R^8$ is OH.

(i) $R^1$ is H, $X^1$ is CH, and $R^8$ is $SR^{11}$. $R^1$ is H, $X^1$ is CH, and $R^8$ is SH. $R^1$ is $CH_3$, $X^1$ is CH, and $R^8$ is $SR^{11}$. $R^1$ is $CH_3$, $X^1$ is CH, and $R^8$ is SH. $R^1$ is H, $X^1$ is N, and $R^8$ is $SR^{11}$. $R^1$ is H, $X^1$ is N, and $R^8$ is SH. $R^1$ is $CH_3$, $X^1$ is N, and $R^8$ is $SR^{11}$, $R^1$ is $CH_3$, $X^1$ is N, and $R^8$ is SH.

(j) $R^1$ is H, $X^1$ is CH, $R^9$ is H and $R^8$ is $NR^{11}R^{12}$. $R^1$ is H, $X^1$ is CH, $R^9$ is H and $R^8$ is $NH_2$. $R^1$ is $CH_3$, $X^1$ is CH, $R^9$ is H and $R^8$ is $NR^{11}R^{12}$. $R^1$ is $CH_3$, $X^1$ is CH, $R^9$ is H and $R^8$ is $NH_2$. $R^1$ is H, $X^1$ is N, $R^9$ is H and $R^8$ is $NR^{11}R^{12}$. $R^1$ is H, $X^1$ is N, $R^9$ is H, and $R^8$ is $NH_2$. $R^1$ is $CH_3$, $X^1$ is N, $R^9$ is H and $R^8$ is $NR^{11}R^{12}$. $R^1$ is $CH_3$, $X^1$ is N, $R^9$ is H and $R^8$ is $NH_2$. $R^1$ is H, $X^1$ is CH, $R^9$ is $NR^{11}R^{12}$ and $R^8$ is $NR^{11}R^{12}$, $R^1$ is H, $X^1$ is CH, $R^9$ is $NR^{11}R^{12}$ and $R^8$ is $NH_2$. $R^1$ is $CH_3$, $X^1$ is CH, $R^9$ is $NR^{11}R^{12}$ and $R^8$ is $NR^{11}R^{12}$, $R^1$ is $CH_3$, $X^1$ is CH, $R^9$ is $NR^{11}R^{12}$ and $R^8$ is $NH_2$. $R^1$ is H, $X^1$ is N, $R^9$ is $NR^{11}R^{12}$ and $R^8$ is $NR^{11}R^{12}$. $R^1$ is H, $X^1$ is N, $R^9$ is $NR^{11}R^{12}$ and $R^8$ is $NH_2$. $R^1$ is $CH_3$, $X^1$ is N, $R^9$ is $NR^{11}R^{12}$ and $R^8$ is $NR^{11}R^{12}$. $R^1$ is $CH_3$, $X^1$ is N, $R^9$ is $NR^{11}R^{12}$ and $R^8$ is $NH_2$.

(k) $R^1$ is H, $X^1$ is CH, and $R^8$ and $R^9$ are independently $SR^{11}$. $R^1$ is $CH_3$, $X^1$ is CH, and $R^8$ and $R^9$ are independently $SR^{11}$. $R^1$ is H, $X^1$ is N, and $R^8$ and $R^9$ are independently $SR^{11}$. $R^1$ is $CH_3$, $X^1$ is N, and $R^8$ and $R^9$ are independently $SR^{11}$.

In one embodiment of the compound of Formula VIb, $R^{17}$ is $-OR^{18}$. The following are additional independent aspects of this embodiment:

(a) $R^1$ is H. $R^1$ is $CH_3$.
(b) $X^1$ is $C-R^{10}$. $X^1$ is $C-H$. $X^1$ is N.
(c) $R^8$ is $NR^{11}R^{12}$. $R^8$ is $OR^{11}$. $R^8$ is $SR^{11}$.
(d) $R^9$ is H. $R^9$ is $NR^{11}R^{12}$. $R^9$ is $SR^{11}$.
(e) $R^{2b}$ is $OR^4$. $R^{2b}$ is F. Each $R^{2a}$ and $R^{2b}$ is independently $OR^4$. $R^{2a}$ is $OR^4$ and $R^{2b}$ is F. $R^{2a}$ is $OR^4$, $R^{2b}$ is F and $R^4$ is $C(O)R^5$. $R^{2a}$ is $OR^4$, $R^{2b}$ is F and $R^4$ is $C(O)R^5$ wherein $R^5$ is phenyl or substituted phenyl. $R^{2b}$ is $OR^4$ wherein $R^4$ is $C(R^5)_2R^6$ and $R^6$ is phenyl or substituted phenyl. $R^{2b}$ is $OR^4$ wherein $R^4$ is $CH_2R^6$ and $R^6$ is phenyl. $R^{2b}$ is $OR^4$ wherein $R^4$ is $CH_2R^6$ and $R^6$ is substituted phenyl. Each $R^{2a}$ and $R^{2b}$ is $OR^4$ wherein each $R^4$ is independently $C(R^5)_2R^6$ and $R^6$ is phenyl or substituted phenyl. Each $R^{2a}$ and $R^{2b}$ is $OR^4$ wherein each $R^4$ is $CH_2R^6$ and $R^6$ is phenyl. Each $R^{2a}$ and $R^{2b}$ is $OR^4$ wherein each $R^4$ is $CH_2R^6$ and each $R^6$ is independently substituted phenyl. Each $R^{2a}$ and $R^{2b}$ is $OR^4$ wherein the two $R^4$ taken together are $-C(R^{19})_2-$. Each $R^{2a}$ and $R^{2b}$ is $OR^4$ wherein the two $R^4$ taken together are $-C(CH_3)_2-$. Each $R^{2a}$ and $R^{2b}$ is $OR^4$ wherein the two $R^4$ taken together are $-CH(R^{19})-$. Each $R^{2a}$ and $R^{2b}$ is $OR^4$ wherein the two $R^4$ taken together are $-CH(R^{19})-$ wherein $R^{19}$ is phenyl or substituted phenyl. $R^{2a}$ is $OR^4$ wherein $R^4$ is $C(R^5)_2R^6$, $R^6$ is phenyl or substituted phenyl and $R^{2b}$ is F. $R^{2a}$ is H.

(f) $R^7$ is $C(O)R^5$. $R^7$ is $C(R^5)_2R^6$ and $R^6$ is phenyl or substituted phenyl. $R^7$ is $CH_2R^6$ and $R^6$ is phenyl. $R^7$ is $CH_2R^6$ and $R^6$ is substituted phenyl. $R^7$ is $C(R^5)_2R^6$ and each $R^5$ and $R^6$ is independently phenyl or substituted phenyl. $R^7$ is $Si(R^3)_3$. $R^7$ is $Si(R^3)_2$(t-butyl) wherein each $R^3$ is $CH_3$. $R^7$ is $Si(R^3)_2$(t-butyl) wherein each $R^3$ is independently phenyl or substituted phenyl. $R^7$ is tetrahydro-2H-pyran-2-yl. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $-C(CH_3)_2-$. $R^7$ is $Si(R^3)_3$ and each $R^{2a}$ and $R^{2b}$ is $OR^4$ wherein the two $R^4$ taken together are $-C(CH_3)_2-$. $R^7$ is $Si(R^3)_2$(t-butyl) wherein each $R^3$ is $CH_3$ and each $R^{2a}$ and $R^{2b}$ is $OR^4$ wherein the two $R^4$ taken together are $-C(CH_3)_2-$. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are $-C(CH_3)_2-$. $R^7$ is tetrahydro-2H-pyran-2-yl and each $R^{2a}$ and $R^{2b}$ is $OR^4$ wherein the two $R^4$ taken together are $-C(CH_3)_2-$. $R^7$ is $C(O)R^5$ and each $R^{2a}$ and $R^{2b}$ is $OR^4$ wherein the two $R^4$ taken together are $-C(CH_3)_2-$. $R^7$ is $C(R^5)_2R^6$ wherein each $R^5$ and $R^6$ is independently phenyl or substituted phenyl and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $Si(R^3)_3$ and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $Si(R^3)_2$(t-butyl) wherein each $R^3$ is $CH_3$ and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $Si(R^3)_2$(t-butyl) wherein each $R^3$ is independently phenyl or substituted phenyl and each $R^{2a}$ and $R^{2b}$ is $OR^4$ wherein the two $R^4$ taken together are $-CH(R^{19})-$ wherein $R^{19}$ is phenyl or substituted phenyl. $R^7$ is tetrahydro-2H-pyran-2-yl and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $C(O)R^5$ and each $R^{2a}$ and $R^{2b}$ is $OR^4$ wherein the two $R^4$ taken together are $-CH(R^{19})-$ wherein $R^{19}$ is phenyl or substituted phenyl. $R^7$ is $C(O)R^5$ wherein $R^5$ is phenyl or substituted phenyl and $R^{2b}$ is F.

(g) $R^{18}$ is $(C_1-C_8)$alkyl or substituted $(C_1-C_8)$alkyl. $R^{18}$ is $(C_1-C_8)$alkyl. $R^{18}$ is methyl.

(h) $R^1$ is H, $X^1$ is CH, and $R^8$ is $NR^{11}R^{12}$. $R^1$ is H, $X^1$ is CH, and $R^8$ is $NH_2$. $R^1$ is $CH_3$, $X^1$ is CH, and $R^5$ is $NR^{11}R^{12}$. $R^1$ is $CH_3$, $X^1$ is CH, and, $R^8$ is $NH_2$. $R^1$ is H, $X^1$ is N, and $R^8$ is $NR^{11}R^{12}$. $R^1$ is H, $X^1$ is N, and $R^8$ is $NH_2$. $R^1$ is $CH_3$, $X^1$ is N, and $R^8$ is $NR^{11}R^{12}$. $R^1$ is $CH_3$, $X^1$ is N, and $R^8$ is $NH_2$. $R^1$ is H, $X^1$ is CH, and $R^9$ is $NR^{11}R^{12}$. $R^1$ is H, $X^1$ is CH, and $R^9$ is $NH_2$. $R^1$ is H, $X^1$ is CH, and $R^9$ is $SR^{11}$. $R^1$ is $NR^{11}R^{12}$. $R^1$ is H, $X^1$ is CH, and $R^9$ is $NH_2$. $R^1$ is H, $X^1$ is CH, and $R^9$ is $SR^{11}$. $R^1$ is H, $X^1$ is CH, and $R^9$ is $R^9$ is SH. $R^1$ is H, $X^1$ is CH, and $R^9$ is H. $R^1$ is $CH_3$, $X^1$ is CH, and $R^9$ is $NR^{11}R^{12}$. $R^1$ is $CH_3$, $X^1$ is CH, and $R^9$ is $NH_2$. $R^1$ is $CH_3$, $X^1$ is CH, and $R^9$ is $SR^{11}$. $R^1$ is $CH_3$, $X^1$ is CH, and $R^9$ is SH. $R^1$ is $CH_3$, $X^1$ is CH, and $R^9$ is H.

(i) $R^1$ is H, $X^1$ is CH, and $R^8$ is $OR^{11}$. $R^1$ is H, $X^1$ is CH, and $R^8$ is OH. $R^1$ is $CH_3$, $X^1$ is CH, and $R^8$ is $OR^{11}$. $R^1$ is $CH_3$, $X^1$ is CH, and $R^8$ is OH. $R^1$ is H, $X^1$ is N, and $R^8$ is $OR^{11}$. $R^1$ is H, $X^1$ is N, and $R^8$ is OH. $R^1$ is $CH_3$, $X^1$ is N, and $R^8$ is $OR^{11}$. $R^1$ is $CH_3$, $X^1$ is N, and $R^8$ is OH.

(j) $R^1$ is H, $X^1$ is CH, and $R^8$ is $SR^{11}$. $R^1$ is H, $X^1$ is CH, and $R^8$ is SH. $R^1$ is $CH_3$, $X^1$ is CH, and $R^8$ is $SR^{11}$. $R^1$ is $CH_3$, $X^1$ is CH, and $R^8$ is SH. $R^1$ is H, $X^1$ is N, and $R^8$ is $SR^{11}$. $R^1$ is H, $X^1$ is N, and $R^8$ is SH. $R^1$ is $CH_3$, $X^1$ is N, and $R^8$ is $SR^{11}$. $R^1$ is $CH_3$, $X^1$ is N, and $R^8$ is SH.

(k) $R^1$ is H, $X^1$ is CH, $R^9$ is H and $R^8$ is $NR^{11}R^{12}$. $R^1$ is H, $X^1$ is CH, $R^9$ is H and $R^8$ is $NH_2$. $R^1$ is $CH_3$, $X^1$ is CH, $R^9$ is H and $R^8$ is $NR^{11}R^{12}$. $R^1$ is $CH_3$, $X^1$ is CH, $R^9$ is H and $R^8$ is $NH_2$. $R^1$ is H, $X^1$ is N, $R^9$ is H and $R^8$ is $NR^{11}R^{12}$. $R^1$ is H, $X^1$ is N, $R^9$ is H and $R^8$ is $NH_2$. $R^1$ is $CH_3$, $X^1$ is N, $R^9$ is H and $R^8$ is $NR^{11}R^{12}$. $R^1$ is $CH_3$, $X^1$ is N, $R^9$ is H and $R^8$ is $NH_3$. $R^1$ is H, $X^1$ is CH, $R^9$ is $NR^{11}R^{12}$ and $R^8$ is $NR^{11}R^{12}$. $R^1$ is H, $X^1$ is CH, $R^9$ is $NR^{11}R^{12}$ and $R^8$ is $NH_2$. $R^1$ is $CH_3$, $X^1$ is CH, $R^9$ is $NR^{11}R^{12}$ and $R^8$ is $NR^{11}R^{12}$. $R^1$ is $CH_3$, $X^1$ is CH, $R^9$ is $NR^{11}R^{12}$ and $R^8$ is $NH_2$. $R^1$ is H, $X^1$ is N, $R^9$ is $NR^{11}R^{12}$ and $R^8$ is $NR^{11}R^{12}$. $R^1$ is H, $X^1$ is N, $R^9$ is $NR^{11}R^{12}$ and $R^8$ is $NH_2$. $R^1$ is $CH_3$, $X^1$ is N, $R^9$ is $NR^{11}R^{12}$ and $R^8$ is $NR^{11}R^{12}$. $R^1$ is $CH_3$, $X^1$ is N, $R^9$ is $NR^{11}R^{12}$ and $R^8$ is $NH_2$.

(l) $R^1$ is H, $X^1$ is CH, and $R^8$ and $R^9$ are independently $SR^{11}$. $R^1$ is $CH_3$, $X^1$ is CH, and $R^8$ and $R^9$ are independently $SR^{11}$. $R^1$ is H, $X^1$ is N, and $R^8$ and $R^9$ are independently $SR^{11}$. $R^1$ is $CH_3$, $X^1$ is N, and $R^8$ and $R^9$ are independently $SR^{11}$.

In another embodiment, the compound of Formula VIb is a compound of Formula VIc

Formula VIc

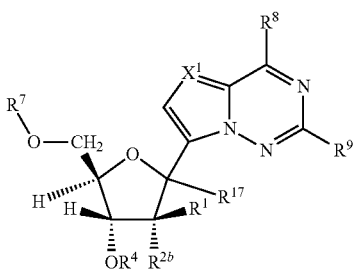

or an acceptable salt thereof,
wherein:
$R^{2b}$ is $OR^4$ or F;
each $R^4$ is independently —$CH_2R^6$ or $C(O)R^5$ wherein $R^5$ is phenyl or substituted phenyl;
$R^7$ is $Si(R^3)_3$, $C(O)R^5$ or —$C(R^5)_2R^6$ wherein each $R^5$ is independently H, phenyl, or substituted phenyl;
$R^6$ is phenyl or substituted phenyl; and
the remaining variables are defined as in Formula VI.

In one aspect of this embodiment, $R^{2b}$ is $OR^4$. In another aspect of this embodiment, $R^{2b}$ is F. In another aspect of this embodiment, $R^7$ is —$CH_2R^6$. In another aspect of this embodiment, $R^7$ is $C(O)R^5$ wherein $R^5$ is phenyl or substituted phenyl. In another aspect of this embodiment, $R^{2b}$ is F and each $R^4$ and $R^7$ is $C(O)R^5$ wherein each $R^5$ is independently phenyl or substituted phenyl. In another aspect of this embodiment, $R^{17}$ is OH. In another aspect of this embodiment, $R^{17}$ is $OR^{18}$. In another aspect of this embodiment, $R^{17}$ is —$OC(O)R^{18}$. In another aspect of this embodiment, $R^{17}$ is —$OC(O)CH_3$. In another aspect of this embodiment, $R^{17}$ is ethoxy or methoxy. In another aspect of this embodiment, $X^1$ is C—$R^{10}$. In another aspect of this embodiment, $X^1$ is C—H. In another aspect of this embodiment, $X^1$ is N. In another aspect of this embodiment, $R^1$ is H. In another aspect of this embodiment, $R^1$ is $CH_3$. In another aspect of this embodiment, $R^{17}$ is OH and $X^1$ is C—$R^{10}$. In another aspect of this embodiment, $R^{17}$ is —$OC(O)R^{18}$ and $X^1$ is C—$R^{10}$. In another aspect of this embodiment, $R^{17}$ is —$OC(O)CH_3$ and $X^1$ is C—$R^{10}$. In another aspect of this embodiment, $R^{17}$ is $OR^{18}$ and $X^1$ is C—$R^{10}$. In another aspect of this embodiment, $R^{17}$ is OH and $X^1$ is C—H. In another aspect of this embodiment, $R^{17}$ is —$OC(O)R^{18}$ and $X^1$ is C—H. In another aspect of this embodiment, $R^{17}$ is —$OC(O)CH_3$ and $X^1$ is C—H. In another aspect of this embodiment, $R^{17}$ is $OR^{18}$ and $X^1$ is C—H, in another aspect of this embodiment, $R^{17}$ is OH and $X^1$ is N. In another aspect of this embodiment, $R^{17}$ is —$OC(O)R^{18}$ and $X^1$ is N. In another aspect of this embodiment, $R^{17}$ is —$OC(O)CH_3$ and $X^1$ is N. In another aspect of this embodiment, $R^{17}$ is $OR^{18}$ and $X^1$ is N. In another aspect of this embodiment, $R^{17}$ is OH, $R^1$ is H, and $X^1$ is C—$R^{10}$. In another aspect of this embodiment, $R^{17}$ is —$OC(O)R^{18}$, $R^1$ is H and $X^1$ is C—$R^{10}$. In another aspect of this embodiment, $R^{17}$ is —$OC(O)CH_3$ $R^1$ is H and $X^1$ is C—$R^{10}$. In another aspect of this embodiment, $R^{17}$ is $OR^{18}$, $R^1$ is H and $X^1$ is C—$R^{10}$. In another aspect of this embodiment, $R^{17}$ is OH, $R^1$ is H and $X^1$ is C—H. In another aspect of this embodiment, $R^{17}$ is —$OC(O)R^{18}$, $R^1$ is H and $X^1$ is C—H. In another aspect of this embodiment, $R^{17}$ is —$OC(O)CH_3$, $R^1$ is H and $X^1$ is C—H. In another aspect of this embodiment, $R^{17}$ is $OR^{18}$, $R^1$ is H and $X^1$ is C—H. In another aspect of this embodiment, $R^{17}$ is OH, $R^1$ is H and $X^1$ is N. In another aspect of this embodiment, $R^{17}$ is —$OC(O)R^{18}$, $R^1$ is H and $X^1$ is N. In another aspect of this embodiment, $R^{17}$ is —$OC(O)CH_3$, $R^1$ is H and $X^1$ is N. In another aspect of this embodiment, $R^{17}$ is $OR^{18}$, $R^1$ is H and $X^1$ is N. In another aspect of this embodiment, $R^{17}$ is —$OC(O)CH_3$, $R^1$ is H and $X^1$ is N. In another aspect of this embodiment, $R^{17}$ is $OR^{18}$, $R^1$ is H and $X^1$ is N. In another aspect of this embodiment, $R^{17}$ is OH, $R^1$ is $CH_3$, and $X^1$ is C—$R^{10}$. In another aspect of this embodiment, $R^{17}$ is —$O(O)R^{18}$, $R^1$ is $CH_3$ and $X^1$ is C—$R^{10}$. In another aspect of this embodiment, $R^{17}$ is —$OC(O)CH_3$ $R^1$ is $CH_3$ and $X^1$ is C—$R^{10}$. In another aspect of this embodiment, $R^{17}$ is $OR^{18}$, $R^1$ is $CH_3$ and $X^1$ is C—$R^{10}$. In another aspect of this embodiment, $R^{17}$ is OH, $R^1$ is $CH_3$ and $X^1$ is C—H. In another aspect of this embodiment, $R^{17}$ is —$OC(O)R^{18}$, $R^1$ is $CH_3$ and $X^1$ is C—H. In another aspect of this embodiment, $R^{17}$ is —$OC(O)CH_3$, $R^1$ is $CH_3$ and $X^1$ is C—H. In another aspect of this embodiment, $R^{17}$ is $OR^{18}$, $R^1$ is $CH_3$ and $X^1$ is C—H. In another aspect of this embodiment, $R^{17}$ is OH, $R^1$ is $CH_3$ and $X^1$ is N. In another aspect of this embodiment, $R^{17}$ is —$OC(O)R^{18}$, $R^1$ is $CH_3$ and $X^1$ is N. In another aspect of this embodiment, $R^{17}$ is —$OC(O)CH_3$, $R^1$ is $CH_3$ and $X^1$ is N. In another aspect of this embodiment, $R^{17}$ is $OR^{18}$, $R^1$ is $CH_3$ and $X^1$ is N.

In another embodiment, the compound of Formula VIb is a compound of Formula VId

Formula VId

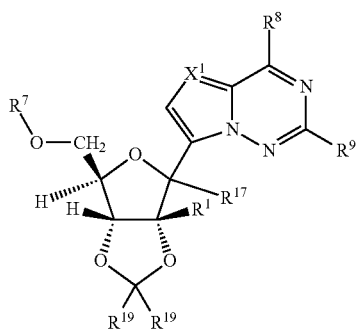

or an acceptable salt thereof,
wherein:
each $R^{19}$ is independently H, phenyl, substituted phenyl, or methyl and
$R^7$ is —$C(R^5)_2R^6$, $Si(R^3)_3$, $C(O)R^5$, or

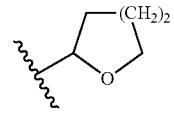

and the remaining variables are defined as in Formula VI.
In one aspect of this embodiment, $R^7$ is $CH_2R^6$ wherein $R^6$ is phenyl or substituted phenyl. In one aspect of this embodiment, $R^7$ is $C(R^5)_2R^6$ wherein each $R^5$ or $R^6$ is independently phenyl or substituted phenyl. In one aspect of this embodiment, $R^7$ is $Si(R^3)_3$. In one aspect of this embodiment, $R^7$ is $Si(R^3)_2$(t-butyl) wherein each $R^3$ is independently phenyl or substituted phenyl. In one aspect of this embodiment, $R^7$ is $Si(R^3)_2$(t-butyl) wherein each $R^3$ is methyl. In one aspect of this embodiment, $R^7$ is $C(O)R^5$. In one aspect of this embodiment, $R^7$ is $C(O)CH_3$. In one aspect of this embodiment, $R^7$ is tetrahydro-2H-pyran-2-yl. In one aspect of this embodiment, each $R^{19}$ is $CH_3$. In one aspect of this embodiment, one of $R^{19}$ is H and the other of $R^{19}$ is phenyl or substituted phenyl. In one aspect of this embodiment, $R^7$ is $CH_2R^6$ wherein $R^6$ is phenyl or substituted phenyl each $R^{19}$ is $CH_3$. In one aspect of this embodiment, $R^7$ is $C(R^5)_2R^6$ wherein each $R^5$ or $R^6$ is independently phenyl or substituted phenyl and each $R^{19}$ is $CH_3$. In one aspect of this embodiment, $R^7$ is $Si(R^3)_3$ and each $R^{19}$ is $CH_3$. In one aspect of this embodiment, $R^7$ is $Si(R^3)_2$(t-butyl) wherein each $R^3$ is independently phenyl or substituted phenyl and each $R^{19}$ is $CH_3$. In one aspect of this embodiment, $R^7$ is $Si(R^3)_2$(t-butyl) wherein each $R^3$ is methyl and each $R^{19}$ is $CH_3$. In one aspect of this embodiment, $R^7$ is $C(O)R^5$ and each $R^{19}$ is $CH_3$. In one aspect of this embodiment, $R^7$ is $C(O)CH_3$ and each $R^{19}$ is $CH_3$. In one aspect of this embodiment, $R^7$ is tetrahydro-2H-pyran-2-yl and each $R^{19}$ is $CH_3$.

In another embodiment of Formula VId, $R^{17}$ is OH. In another embodiment of Formula VId, $R^{17}$ is —OC(O)$R^{18}$. In another embodiment of Formula VId, $R^{17}$ is —OC(O)$CH_3$. In another embodiment of Formula VId, $R^{17}$ is $OR^{18}$. In another aspect of this embodiment, $X^1$ is C—$R^{10}$. In another embodiment of Formula VId, $X^1$ is C—H. In another embodiment of Formula VId, $X^1$ is N. In another embodiment of Formula. VId, $R^1$ is H. In another embodiment of Formula VId, $R^1$ is $CH_3$. In another embodiment of Formula VId, $R^{17}$ is OH and $X^1$ is C—$R^{10}$. In another embodiment of Formula VId, $R^{17}$ is —OC(O)$R^{18}$ and $X^1$ is C—$R^{10}$. In another embodiment of Formula VId, $R^{17}$ is —OC(O)$CH_3$ and $X^1$ is C—$R^{10}$. In another embodiment of Formula VId, $R^{17}$ is $OR^{18}$ and $X^1$ is C—$R^{10}$. In another embodiment of Formula VId, $R^{17}$ is OH and $X^1$ is C—H. In another embodiment of Formula VId, $R^{17}$ is —OC(O)$R^{18}$ and $X^1$ is C—H. In another embodiment of Formula VId, $R^{17}$ is —OC(O)$CH_3$ and $X^1$ is C—H. In another embodiment of Formula VId, $R^{17}$ is $OR^{18}$ and $X^1$ is C—H. In another embodiment of Formula VId, $R^{17}$ is OH and $X^1$ is N. In another embodiment of Formula VId, $R^{17}$ is —OC(O)$R^{18}$ and $X^1$ is N. In another embodiment of Formula VId, $R^{17}$ is —OC(O)$CH_3$ and $X^1$ is N. In another embodiment of Formula VId, $R^{17}$ is $OR^{18}$ and $X^1$ is N. In another embodiment of Formula VId, $R^{17}$ is OH, $R^1$ is H, and $X^1$ is C—$R^{10}$. In another embodiment of Formula VId, $R^{17}$ is —OC(O)$R^{18}$, $R^1$ is H and $X^1$ is C—$R^{10}$. In another embodiment of Formula VId, $R^{17}$ is —OC(O)$CH_3$ $R^1$ is H and $X^1$ is C—$R^{10}$. In another embodiment of Formula VId, $R^{17}$ is $OR^{18}$, $R^1$ is H and $X^1$ is C—$R^{10}$. In another embodiment of Formula VId, $R^{17}$ is OH, $R^1$ is H and $X^1$ is C—H. In another aspect of this embodiment, $R^{17}$ is —OC(O)$R^{18}$, $R^1$ is H and $X^1$ is C—H. In another embodiment of Formula VId, $R^{17}$ is —OC(O)$CH_3$, $R^1$ is H and $X^1$ is C—H. In another embodiment of Formula VId, $R^{17}$ is $OR^{18}$, $R^1$ is H and $X^1$ is C—H. In another embodiment of Formula VId, $R^1$ is H and $X^1$ is N. In another embodiment of Formula VId, $R^{17}$ is —OC(O)$R^{18}$, $R^1$ is H and $X^1$ is N. In another embodiment of Formula VId, $R^{17}$ is —OC(O)$CH_3$, $R^1$ is H and $X^1$ is N. In another embodiment of Formula VId, $R^{17}$ is $OR'^8$, $R^1$ is H and $X^1$ is N. In another embodiment of Formula VId, $R^{17}$ is OH, $R^1$ is $CH_3$, and $X^1$ is C—$R^{10}$. In another embodiment of Formula VId, $R^{17}$ is —OC(O)$R^{18}$, $R^1$ is $CH_3$ and $X^1$ is C—$R^{10}$. In another embodiment of Formula VId, $R^{17}$ is —OC(O)$CH_3$ $R^1$ is $CH_3$ and $X^1$ is C—$R^{10}$. In another embodiment of Formula. VId, $R^{17}$ is $OR^{18}$, $R^1$ is $CH_3$ and $X^1$ is C—$R^{10}$. In another embodiment of Formula VId, $R^{17}$ is OH, $R^1$ is $CH_3$ and $X^1$ is C—H. In another embodiment of Formula VId, $R^{17}$ is —OC(O)$R^{18}$, $R^1$ is $CH_3$ and $X^1$ is C—H. In another embodiment of Formula VId, $R^{17}$ is —OC(O)$CH_3$, $R^1$ is $CH_3$ and $X^1$ is C—H. In another embodiment of Formula VId, $R^{17}$ is $OR^{18}$, $R^1$ is $CH_3$ and $X^1$ is C—H. In another embodiment of Formula VId, $R^{17}$ is OH, $R^1$ is $CH_3$ and $X^1$ is N. In another embodiment of Formula VId, $R^{17}$ is —OC(O)$R^{18}$, $R^1$ is $CH_3$ and $X^1$ is N. In another embodiment of Formula VId, $R^{17}$ is —OC(O)$CH_3$, $R^1$ is $CH_3$ and $X^1$ is N. In another embodiment of Formula VId, $R^{17}$ is $OR^{18}$, $R^1$ is $CH_3$ and $X^1$ is N.

In another embodiment, the compound of Formula VIb is

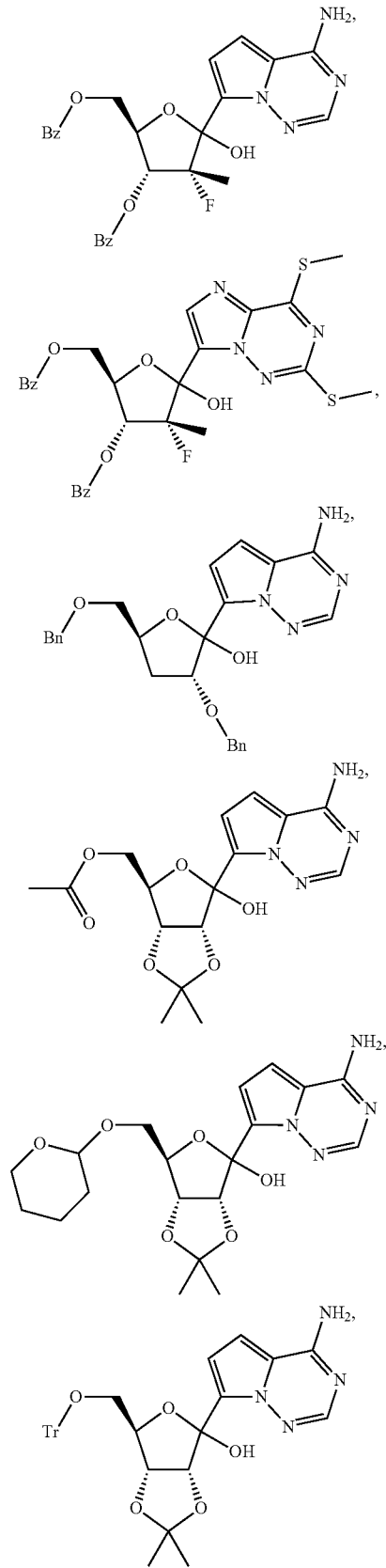

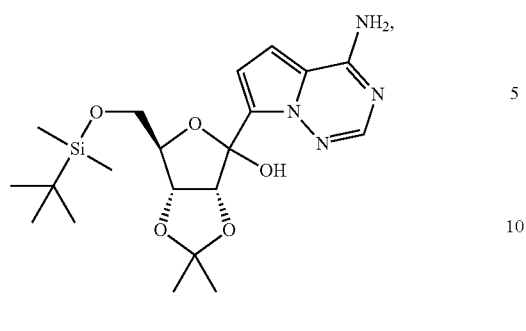
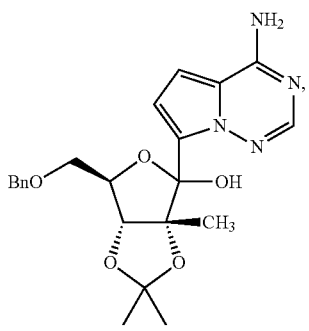
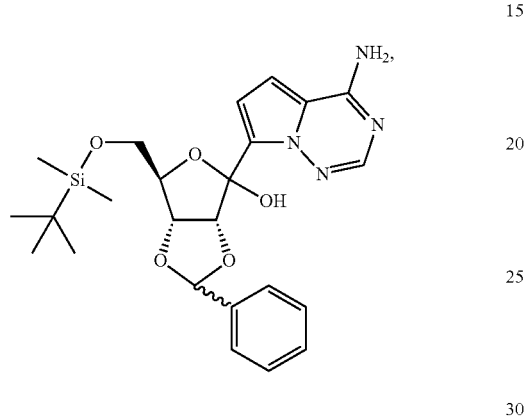
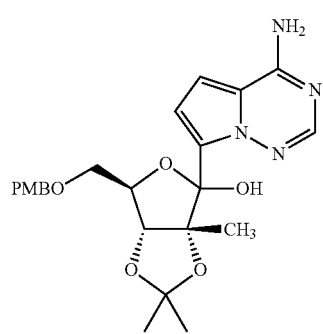
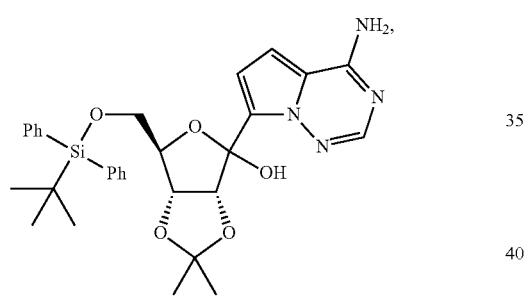
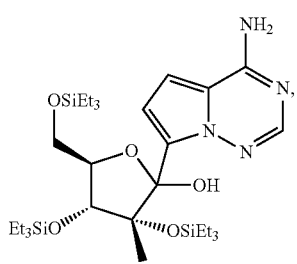
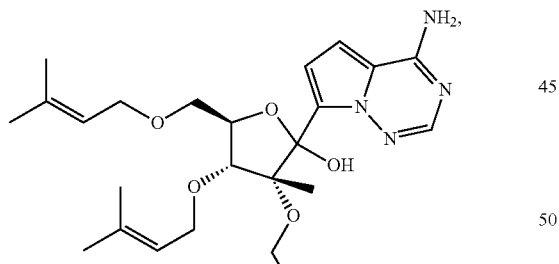
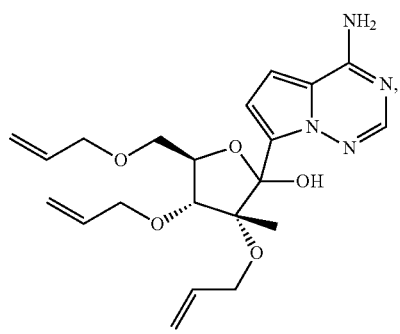
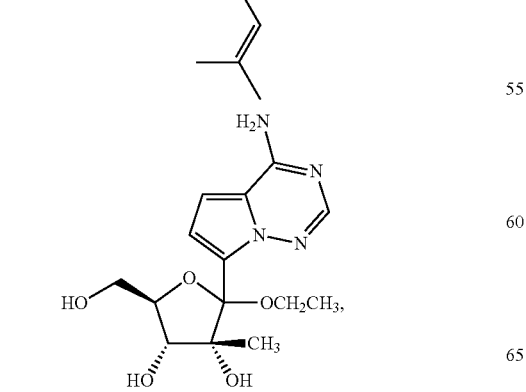
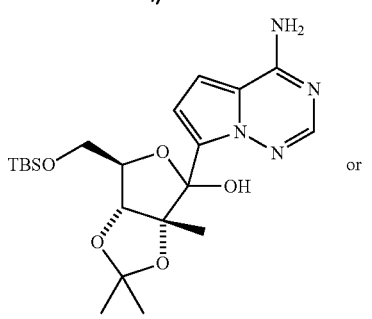

-continued

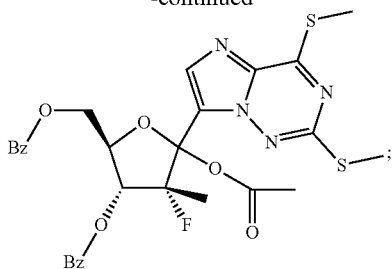

or an acceptable salt thereof.

Definitions

Unless stated otherwise, the following terms and phrases as used herein are intended to have the following meanings:

When trade names are used herein, applicants intend to independently include the tradename product and the active ingredient(s) of the tradename product.

As used herein, "a compound of the invention" or "a compound of Formula I" means a compound of Formula I or an acceptable salt, thereof. Similarly, with respect to isolatable intermediates, the phrase "a compound of Formula (number)" means a compound of that formula and an acceptable salts, thereof.

"Alkyl" is hydrocarbon containing normal, secondary, tertiary or cyclic carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 6 carbon atoms (i.e., $C_1$-$C_6$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, and octyl (—$(CH_2)_2CH_3$).

"Alkoxy" means a group having the formula —O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), to 12 carbon atoms (i.e., alkoxy), or 1 to 6 carbon atoms (i.e., $C_1$-$C_6$ alkoxy). Examples of suitable alkoxy groups include, but are not limited to, methoxy (—O—$CH_3$ or —OMe), ethoxy (—$OCH_2CH_3$ or —OEt), t-butoxy (—O—$C(CH_3)_3$ or —OtBu) and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 6 carbon atoms (i.e., $C_1$-$C_6$ alkyl). Examples of suitable haloalkyl groups include, but are not limited to, —$CF_3$, —$CHF_2$, —$CFH_2$, —$CH_2CF_3$, and the like. The term "haloalkyl" includes "polyfluoroalkyl". The term "polyfluoroalkyl" is an alkyl group, as defined above, in which two or more hydrogen atoms of the alkyl group is replaced with a fluorine atom.

"Alkenyl" is a hydrocarbon containing normal, secondary, tertiary or cyclic carbon atoms with at least one site of unsaturation, i.e. a carbon-carbon, $sp^2$ double bond. For example, an alkenyl group can have 2 to 20 carbon atoms (i.e., $C_2$-$C_{20}$ alkenyl), 2 to 8 carbon atoms (i.e., $C_2$-$C_8$ alkenyl), or 2 to 6 carbon atoms (i.e., $C_2$-$C_6$ alkenyl). Examples of suitable alkenyl groups include, but are not limited to, ethylene or vinyl (—CH=$CH_2$), allyl (—$CH_2$CH=$CH_2$), cyclopentenyl (—$C_5H_7$), and 5-hexenyl (—$CH_2CH_2CH_2CH_2$CH=$CH_2$).

"Alkynyl" is a hydrocarbon containing normal, secondary, tertiary or cyclic carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 8 carbon atoms (i.e., $C_2$-$C_8$ alkyne,), or 2 to 6 carbon atoms (i.e., $C_2$-$C_6$ alkynyl). Examples of suitable alkynyl groups include, but are not limited to, acetylenic (—C≡CH), propargyl (—$CH_2$C≡CH), and the like.

"Alkylene" refers to a saturated, branched or straight chain or cyclic hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene (—$CH_2$—), 1,1-ethyl (—CH($CH_3$)—), 1,2-ethyl (—$CH_2CH_2$—), 1,1-propyl (—CH($CH_2CH_3$)—), 1,2-propyl (—$CH_2$CH($CH_3$)—), 1,3-propyl (—$CH_2CH_2CH_2$—), 1,4-butyl (—$CH_2CH_2CH_2CH_2$—), like.

"Alkenylene" refers to an unsaturated, branched or straight chain or cyclic hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene (—CH=CH—).

"Alkynylene" refers to an unsaturated, branched or straight chain or cyclic hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene propargyl (—$CH_2$C≡C—), and 4-pentynyl (—$CH_2CH_2CH_2$C≡C—).

"Amino" refers generally to a nitrogen radical which can be considered a derivative of ammonia, having the formula —N(X)$_2$, where each "X" is independently H, substituted or unsubstituted alkyl, substituted or unsubstituted carbocyclyl, substituted or unsubstituted heterocyclyl, etc. The hybridization of the nitrogen is approximately $sp^3$. Nonlimiting types of amino include —$NH_2$, —N(alkyl)$_2$, —NH(alkyl), —N(carbocyclyl)$_2$, —NH(carbocyclyl), —N(heterocyclyl)$_2$, —NH(heterocyclyl), —N(aryl)$_2$, —NH(aryl), —N(alkyl)(aryl), —N(alkyl)(heterocyclyl), —N(carbocyclyl)(heterocyclyl), —N(aryl)(heteroaryl), —N(alkyl)(heteroaryl), etc. The term "alkylamino" refers to an amino group substituted with at least one alkyl group. Nonlimiting examples of amino groups include —NH$_2$, —NH(CH$_3$), —N(CH$_3$)$_2$, —NH(CH$_2$CH$_3$), —N(CH$_2$CH$_3$)$_2$, —NH(phenyl), —N(phenyl)$_2$, —NH(benzyl), —N(benzyl)$_2$, etc. Substituted alkylamino refers generally to alkylamino groups, as defined above, in which at least one substituted alkyl, as defined herein, is attached to the amino nitrogen atom. Non-limiting examples of substituted alkylamino includes —NH(alkylene-C(O)—OH), —NH(alkylene-C(O)—O-alkyl), —N(alkylene-C(O)—OH)$_2$, —N(alkylene-C(O)—O-alkyl)$_2$, etc.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Arylalkyl" refers to an acyclic alkyl radical in which one of the hydrogen atoms bonded to a carbon atom, typically a terminal or sp$^3$ carbon atom, is replaced with an aryl radical. Typical arylalkyl groups include, but are not limited to, benzyl, 2-phenyl ethan-1-yl, naphthylmethyl, 2-naphthylethan-1-yl, naphthobenzyl, 2-naphthophenylethan-1-yl and the like. The arylalkyl group can comprise 7 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp$^3$ carbon atom, but also an sp$^2$ carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 8 to 20 carbon atoms, e.g., the alkenyl moiety is 2 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp$^3$ carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 8 to 20 carbon atoms, e.g., the alkynyl moiety is 2 to 6 carbon atoms and the aryl moiety is 6 to 14 carbon atoms.

The term "substituted" in reference to alkyl, alkylene, aryl, arylalkyl, alkoxy, heterocyclyl, heteroaryl, carbocyclyl, etc., for example, "substituted alkyl", "substituted alkylene", "substituted aryl", "substituted arylalkyl", "substituted heterocyclyl", and "substituted carbocyclyl", unless otherwise indicated, means alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R$^b$, —O$^-$, =O, —OR$^b$, —SR$^b$, —S$^-$, —NR$^b_2$, —N$^+$R$^b_3$, =NR$^b$, —CX$_3$, —CN, —OCN, —SCN, —N=C=O, —NCS, —NO, —NO$_2$, =N$_2$, —N$_3$, —NHC(=O)R$^b$, —OC(=O)R$^b$, —NHC(=O)NR$^b_2$, —S(=O)$_2$—, —S(=O)$_2$OH, —S(=O)$_2$R$^b$, —OS(=O)$_2$OR$^b$, —S(=O)$_2$NR$^b_2$, —S(=O)R$^b$, —OP(=O)(OR$^b$)$_2$, P(=O)(OR$^b$)$_2$, —P(=O)(O$^-$)$_2$, —P(=O)(OH)$_2$, —P(O)(OR$^b$)(O$^-$), —C(=O)R$^b$, —C(=O)X, —C(S)R$^b$, —C(O)OR$^b$, —C(O)O$^-$, —C(S)OR$^b$, —C(O)SR$^b$, —C(S)SR$^b$, —C(O)NR$^b_2$, —C(S)NR$^b_2$, —C(=NR$^b$)NR$^b_2$, where each X is independently a halogen: F, Cl, Br, or I; and each R$^b$ is independently H, alkyl, aryl, arylalkyl, a heterocycle, or a protecting group or prodrug moiety. Alkylene, alkenylene, and alkynylene groups may also be similarly substituted. Unless otherwise indicated, when the term "substituted" is used in conjunction with groups such as arylalkyl, which have two or more moieties capable of substitution, the substituents can be attached to the aryl moiety, the alkyl moiety, or both.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; *The Chemistry of Heterocyclic Compounds, A Series of Monographs*" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, or S). The terms "heterocycle" or "heterocyclyl" includes saturated rings, partially unsaturated rings, and aromatic rings (i.e., heteroaromatic rings). Substituted heterocylyls include, for example, heterocyclic rings substituted with any of the substituents disclosed herein including carbonyl groups. A non-limiting example of a carbonyl substituted heterocyclyl is:

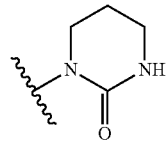 [SMILES: *N1CCCNC1=O]

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, isatinoyl, and bis-tetrahydrofuranyl:

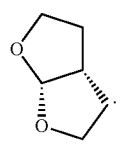

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heteroaryl" refers to an aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those aromatic rings listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, etc.

"Carbocycle" or "carbocyclyl" refers to a saturated (i.e., cycloalkyl), partially unsaturated (e.g., cycloakenyl, cycloalkadienyl, etc.) or aromatic ring having 3 to 7 carbon atoms as a monocycle, 7 to 12 carbon atoms as a bicycle, and up to about 20 carbon atoms as a polycycle. Monocyclic carbocycles have 3 to 7 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system, or spiro-fused rings. Non-limiting examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and phenyl. Non-limiting examples of bicyclo carbocycles includes naphthyl, tetrahydronapthalene, and decaline.

"Carbocyclylalkyl" refers to an acyclic akyl radical in which one of the hydrogen atoms bonded to a carbon atom is replaced with a carbocyclyl radical as described herein. Typical, but non-limiting, examples of carbocyclylalkyl groups include cyclopropylmethyl, cyclopropylethyl, cyclobutylmethyl, cyclopentylmethyl and cyclohexylmethyl.

"Heteroarylalkyl" refers to an alkyl group, as defined herein, in which a hydrogen atom has been replaced with a heteroaryl group as defined herein. Non-limiting examples of heteroaryl alkyl include —CH$_2$-pyridinyl, —CH$_2$-pyrrolyl, —CH$_2$-oxazolyl, —CH$_2$-indolyl, —CH$_2$-isoindolyl, —CH$_2$-purinyl, —CH$_2$-furanyl, —CH$_2$-benzofuranyl, —CH$_2$-benzothiophen yl, —CH$_2$-carbazolyl, —CH$_2$-imidazolyl, —CH$_2$-thiazolyl, —CH$_2$-isoxazolyl, —CH$_2$-pyrazolyl, —CH$_2$-isothiazolyl, —CH$_2$-quinolyl, —CH$_2$-isoquinolyl, —CH$_2$-pyridazyl, —CH$_2$-pyrimidyl, —CH$_2$-pyrazyl, —CH(CH$_3$)-pyridinyl, —CH(CH$_3$)-pyrrolyl, —CH(CH$_3$)-oxazolyl, —CH (CH$_3$)-indolyl, —CH(CH$_3$)-isoindolyl, —CH(CH$_3$)-purinyl, —CH(CH$_3$)-furanyl, —CH(CH$_3$)-thienyl, —CH(CH$_3$)-benzofuranyl, —CH(CH$_3$)-benzothiophenyl, —CH(CH$_3$)-carbazolyl, —CH(CH$_3$)-imidazolyl, —CH(CH$_3$)-thiazolyl, —CH(CH$_3$)-isoxazolyl, —CH (CH$_3$)-pyrazolyl, —CH(CH$_3$)-isothiazolyl, —CH(CH$_3$)-quinolyl, —CH(CH$_3$)-isoquinolyl, —CH(CH$_3$)-pyridazyl, —CH(CH$_3$)-pyrimidyl, —CH(CH$_3$)-pyrazyl, etc.

The term "optionally substituted" in reference to a particular moiety of the compound of Formula I, Ib, Ic, II, IIb, IIc, III, IIIb, IIIc, IV, V, VI, or VIb-d (e.g., an optionally substituted aryl group) refers to a moiety wherein all substituents are hydrogen or wherein one or more of the hydrogens of the moiety may be replaced by substituents such as those listed under the definition of "substituted" or as otherwise indicated.

The term "optionally replaced" in reference to a particular moiety of the compound of Formula I, Ib, Ic, II, IIb, IIc, III, IIIb, IIIc, IV, V, VI, or VIb-d (e.g., the carbon atoms of said (C$_1$-C$_8$)alkyl may be optionally replaced by —O—, —S—, or —NR$^a$—) means that one or more of the methylene groups of the (C$_1$-C$_8$)alkyl may be replaced by 0, 1, 2, or more of the groups specified (e.g., —O—, —S—, or —NR$^a$—).

The term "non-terminal carbon atom(s)" in reference to an alkyl, alkenyl, alkynyl, alkylene, alkenylene, or alkynylene moiety refers to the carbon atoms in the moiety that intervene between the first carbon atom of the moiety and the last carbon atom in the moiety. Therefore, by way of example and not limitation, in the alkyl moiety —CH$_2$(C*) H$_2$(C*)H$_2$CH$_3$ or alkylene moiety —CH$_2$(C*)H$_2$(C*) H$_2$CH$_2$— the C* atoms would be considered to be the non-terminal carbon atoms.

The term "transition metal" or "transition element" is defined following the nomenclature of the International Union of Pure and Applied Chemistry in the *Compendium of Chemical Terminology*, Internet edition.

The term "lanthanide" means the elements La, Ce, Pr, Nd, Pm, Sm, Eu, Gd, Tb, Dy, Ho, Er, Tin, Yb and Lu.

The term "alkaline earth or alkaline earth metal" means the elements Be, Mg, Ca, Sr, Ba and Ra.

The transition metals, lanthanides, alkaline earth metals and other metals such as aluminum, gallium, indium, thallium, tin, lead or bismuth referred to herein may form salts with acidic compounds. For example, they may form salts of triflic acid (CF$_3$SO$_2$OH). Many of these metals can exist in multiple oxidation states and thus form more than one salt with acid compounds. When reference is made to a salt of a metal, all such oxidation states are contemplated as being included in this invention so long as they are stable oxidation states of the metal.

The term "treating", in reference to the method claims described herein, means combining the reagents described in the claim under conditions wherein a reaction occurs. A non-limiting example is "treating a compound of Formula IIIb with a compound of Formula IV" would mean combining the compound of Formula IIIb with a compound of Formula IV" under conditions wherein the two molecules would react. The ordering of the combining step, i.e., adding a compound of Formula IIIb to a compound of Formula IV or adding a compound of Formula IV to a compound of Formula IIIb, is dependent upon the substituents and stability of the respective compounds being combined. The choice of the order of combination would be well understood by one skilled in the art based on the knowledge imparted with the instant disclosure. Both orders of combining the reagents are encompassed by the instant invention.

Unless otherwise specified, the carbon atoms of the compounds of Formula I, Ib, Ic, II, IIb, IIIc, III, IIIb, IIIc, IV, V, VI, or VIb-d are intended to have a valence of four. In some chemical structure representations where carbon atoms do not have a sufficient number of variables attached to produce a valence of four, the remaining carbon substitutents needed to provide a valence of four should be assumed to be hydrogen. For example,

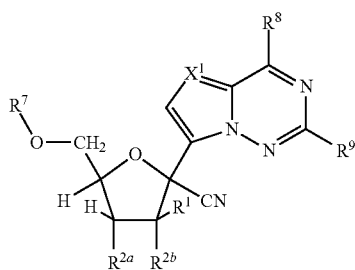

has the same meaning as

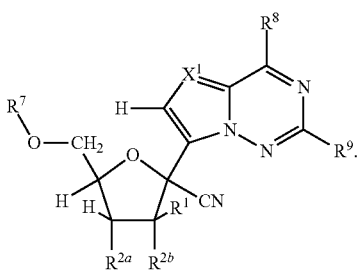

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. Protecting groups are often utilized to mask the reactivity of certain functional groups, to assist in the efficiency of desired chemical reactions, e.g. making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools.

It is to be noted that all enantiomers, diastereomers, and racemic mixtures, tautomers, polymorphs, pseudopolymorphs of compounds within the scope of Formula I, Ib, Ic, II, IIb, IIc, III, IIIb, IIIc, IV, V, VI, or VIb-d and acceptable salts thereof are embraced by the present invention. All mixtures of such enantiomers and diastereomers are within the scope of the present invention.

A compound of Formula I, Ib, Ic, II, IIb, IIc, III, IIIb, IIIc, IV, V, VI, or VIb-d and acceptable salts thereof may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I, Ib, Ic, II, IIb, IIc, III, IIIb, IIIc, IV, V, VI, or VIb-d and their acceptable salts.

A compound of Formula I, Ib, Ic, II, IIb, IIc, III, IIIb, IIIc, IV, V, VI, or VIb-d and acceptable salts thereof may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I, Ib, Ic, II, IIb, IIc, III, IIIb, IIIc, IV, V, VI, or VIb-d and their acceptable salts.

The modifier "about" used in connection with a quantity is inclusive of the stated value and has the meaning dictated by the context (e.g., includes the degree of error associated with measurement of the particular quantity).

The compounds of the invention, exemplified by Formula I, Ib, Ic, II, IIb, IIc, III, IIIb, IIIc, IV, V, VI, or VIb-d may have chiral centers, e.g. chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of Formula I, Ib, Ic, II, IIb, IIc, VI, and VIb-d are nucleosides with an anomeric carbon atom at position 1 of the carbohydrate ring. A non-limiting example would be Formula VIb wherein the $R^{17}$ substituent is in the 1 position of the carbohydrate. Thus Formula VIb is actually a representation of at least two compounds of Formula VIb1 (β riboside) and VIb2 (α riboside) with respect to the anomeric carbon atom. It is intended that Formula I, Ib, II, IIb, VI, and VIb-d are inclusive of both anomeric carbon isomers.

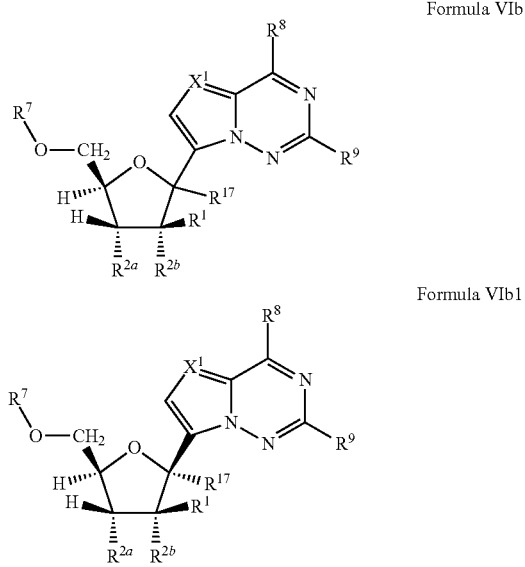

Formula VIb

Formula VIb1

Formula VIb2

The method of preparing a compound of Formula I, Ib or Ic from a compound of Formula II, IIb, or IIc, respectively, provides different ratios of the β riboside to α riboside depending upon the reaction conditions and particularly the Lewis acid used to promote the reaction. In preferred embodiments, the amount of β riboside exceeds the amount of α riboside. In one preferred embodiment, the ratio of β riboside to α riboside is at least about 3:1; in another preferred embodiment, the ratio is at least about 3.5:1; in another preferred embodiment, the ratio is at least about 4:1; in another preferred embodiment, the ratio is at least about 5:1; in another preferred embodiment, the ratio is at least about 6:1; in another preferred embodiment, the ratio is at least about 7:1; in another preferred embodiment, the ratio is at least about 8:1; and in a particular preferred embodiment, the ratio is at least 9:1 or more.

Whenever a compound described herein is substituted with more than one of the same designated group, e.g., "R" or "$R^1$", then it will be understood that the groups may be the same or different, i.e., each group is independently selected. Wavy lines, ∿∿, indicate the site of covalent bond attachments to the adjoining substructures, groups, moieties, or atoms.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

One skilled in the art will recognize that the pyrrolo[1,2-f][1,2,4]triazinyl and imidazo[1,2-f][1,2,4]triazinyl heterocycles can exist in tautomeric forms. For example, but not by way of limitation, structures (a) and (b) can have equivalent tautomeric forms as shown below:

-continued

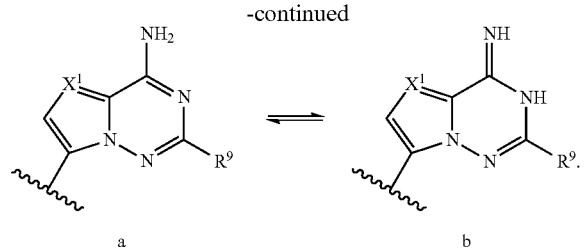

a       b

All possible tautomeric forms of the heterocycles in all of the embodiments disclosed herein are within the scope of the invention.

All publications, patents, and patent documents cited herein above are incorporated by reference herein, as though individually incorporated by reference.

EXAMPLES

Certain abbreviations and acronyms are used in describing the experimental details. Although most of these would be understood by one skilled in the art, Table 1 contains a list of many of these abbreviations and acronyms.

TABLE 1

List of abbreviations and acronyms.

| Abbreviation | Meaning |
| --- | --- |
| Ac$_2$O | acetic anhydride |
| AIBN | 2,2'-azobis(2-methylpropionitrile) |
| Bn | unsubstituted benzyl |
| BnBr | benzylbromide |
| BSA | bis(trimethylsilyl)acetamide |
| Bz | benzoyl |
| BzCl | benzoyl chloride |
| CDI | carbonyl diimidazole |
| DABCO | 1,4-diazabicyclo[2.2.2]octane |
| DBN | 1,5-diazabicyclo[4.3.0]non-5-ene |
| DDQ | 2,3-dichloro-5,6-dicyano-1,4-benzoquinone |
| DBU | 1,5-diazabicyclo[5.4.0]undec-5-ene |
| DCA | dichloroacetamide |
| DCC | dicyclohexylcarbodiimide |
| DCM | dichloromethane |
| DMAP | 4-dimethylaminopyridine |
| DME | 1,2-dimethoxyethane |
| DMTCl | dimethoxytrityl chloride |
| DMSO | dimethylsulfoxide |
| DMTr | 4,4'-dimethoxytrityl |
| DMF | dimethylformamide |
| EtOAc | ethyl acetate |
| ESI | electrospray ionization |
| HMDS | hexamethyldisilazane |
| HPLC | High pressure liquid chromatography |
| LDA | lithium diisopropylamide |
| LRMS | low resolution mass spectrum |
| MCPBA | meta-chloroperbenzoic acid |
| MeCN | acetonitrile |
| MeOH | methanol |
| MMTC | mono methoxytrityl chloride |
| m/z or m/e | mass to charge ratio |
| MH$^+$ | mass plus 1 |
| MH$^-$ | mass minus 1 |
| MsOH | methanesulfonic acid |
| MS or ms | mass spectrum |
| NBS | N-bromosuccinimide |
| PMB | para-methoxybenzyl |
| Ph | phenyl |
| rt or r.t. | room temperature |
| TBAF | tetrabutylammonium fluoride |
| TMSCl | chlorotrimethylsilane |
| TMSBr | bromotrimethylsilane |
| TMSI | iodotrimethylsilane |

TABLE 1-continued

List of abbreviations and acronyms.

| Abbreviation | Meaning |
| --- | --- |
| TMSOTf | (trimethylsilyl)trifluoromethylsulfonate |
| TEA | triethylamine |
| TBA | tributylamine |
| TBAP | tributylammonium pyrophosphate |
| TBSCl | t-butyldimethylsilyl chloride |
| TEAB | triethylammonium bicarbonate |
| TFA | trifluoroacetic acid |
| TLC or tlc | thin layer chromatography |
| Tr | triphenylmethyl |
| Tol | 4-methylbenzoyl |
| Turbo Grignard | 1:1 mixture of isopropylmagnesium chloride and lithium chloride |
| δ | parts per million down field from tetramethylsilane |

Compound 1c

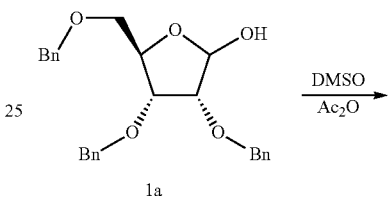

1a

1b

Compound 1a (prepared according to *J. Org. Chem.*, 1961, 26, 4605; 10.0 g, 23.8 mmol) was dissolved in anhydrous DMSO (30 mL) and placed under nitrogen. Acetic anhydride (20 mL) was added, and the mixture was stirred for 48 h at room temperature. When the reaction was complete by LC/MS, it was poured onto 500 mL ice water and stirred for 20 min. The aqueous layer was extracted with ethyl acetate (3×200 mL). The organic extracts were combined and washed with water (3×200 mL). The aqueous layers were discarded and the organic was dried over anhydrous MgSO$_4$ and evaporated to dryness. The residue was taken up in DCM and loaded onto a silica gel column. The final product 1b was purified by elution with 25% EtOAc/hexanes; 96% yield. $^1$H-NMR (CD$_3$CN): δ 3.63-3.75 (m, 2H), 4.27 (d, 1H), 4.50-4.57 (m, 3H), 4.65 (s, 3H), 4.69-4.80 (m, 2H), 7.25 (d, 2H), 7.39 (m, 13H).

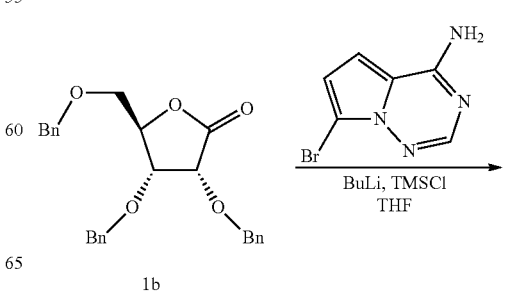

1b

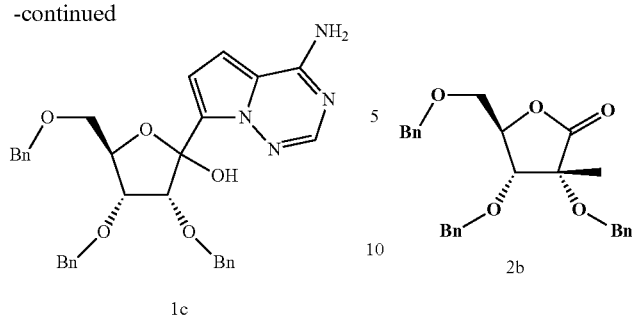

1c

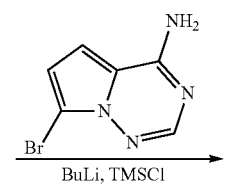

2b

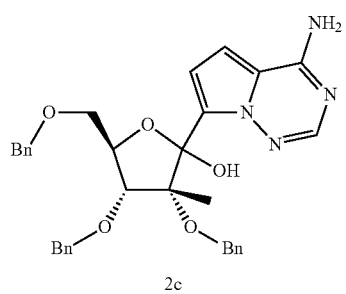

2c

7-Bromo-pyrrolo[2,1-f][1,2,4]triazin-4-ylamine (prepared according to WO2007/056170, 0.5 g, 2.4 mmol) was suspended in anhydrous THF (10 mL). Under nitrogen with stirring, TMSCl (0.668 mL, 5.28 mml) was added and the mixture was stirred for 20 min. at room temperature. The reaction was then cooled to −78° C. and a solution of BuLi (6.0 mL, 1.6 M in hexanes) was added slowly. The reaction was stirred for 10 min. at −78° C. and then a solution of the lactone 1b (1.0 g, 2.4 mmol in THF) was added via syringe. When the reaction was complete by LC/MS, acetic acid (0.5 mL) was added to quench the reaction. Solvents were removed by rotary evaporation and the residue was taken up in a mixture of 50:50 dichloromethane/water (100 mL). The organic layer was collected and washed with 50 mL additional water, dried over anhydrous MgSO$_4$ and filtered. Evaporation and purification by column chromatography (0-50% EtOAc:hexanes) provided a 1:1 mixture of anomers 1c; 25% yield. LC/MS (m/z: 553, M+H$^+$).

Compound 2c

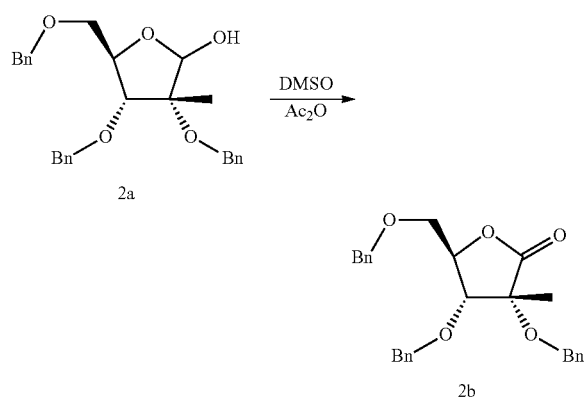

2a

2b

To a dry, argon purged round bottom flask (100 mL) were added anhydrous DMSO (6 mL) and anhydrous acetic anhydride (4 mL, 42.4 mmol). Compound 2a (1.0 g, 2.3 mmol) was then added and the reaction mixture was allowed to stir at room temperature until complete disappearance of the starting material. After 17 h, the flask was placed into an ice bath and sat. NaHCO$_3$ (6 mL) was added to neutralize the reaction mixture. The organic material was then extracted using EtOAc (3×10 mL) and the combined organic layers were dried using MgSO$_4$, The solvent was removed under reduced pressure and the crude material was purified using flash silica gel chromatography (hexanes EtOAc). 955 mg (96%) of the desired material 2b was isolated. LC/MS=433.2 (M+H$^+$). $^1$H NMR (300 MHz, CDCl$_3$): δ 7.33 (m, 15H), 4.80 (d, 1H), 4.64 (m, 6H), 4.06 (d, 1H), 3.79 (dd, 1H), 3.64 (dd, 1H), 1.54 (s, 3H).

To a dry, argon purged round bottom flask (100 mL) were added 7-bromo-pyrrolo[2,1-f][1,2,4]triazin-4-ylamine (234 mg, 1.10 mmol) and anhydrous THF (1.5 mL). TMSCl (276 μL, 2.2 mmol) was then added and the reaction mixture stirred for 2 h. The flask was placed into a dry ice/acetone bath (∼−78° C.) and BuLi (2.5 mL, 4.0 mmol, 1.6 M in hexanes) was added dropwise. After 1 h, a solution of 2b (432 mg, 1.0 mmol) in THF was cooled to 0° C. and then added to the reaction flask dropwise. After 1 h of stirring at −78° C., the flask was warmed to 0° C. and sat. NH$_4$Cl (5 mL) was added to quench the reaction. The organics were extracted using EtOAc (3×10 mL) and the combined organic layers were dried using MgSO$_4$, The solvent was removed under reduced pressure and the crude material was purified using flash silica gel chromatography (hexanes/EtOAc). 560 mg (90%) of the desired material 2c was isolated. LC/MS=567.2 (M+H$^+$). $^1$H NMR (300 MHz, CDCl$_3$): δ 7.85 (m, 1H), 7.27 (m, 15H), 7.01 (m, 1H), 6.51 (m, 1H), 4.66 (in, 8H), 4.40 (m, 2H), 3.79 (m, 3H), 1.62 (s, 2'-CH$_3$ from the one anomer), 1.18 (s, 2'-CH$_3$ from the other anomer).

Alternative Procedures for 2c

To a dry, argon purged round bottom flask were added 7-bromo-pyrrolo[2,1-f][1,2,4]triazin-4-ylamine (9.6 g, 45 mmol) and anhydrous THF (60 mL). TMSCl (12.4 mL, 99 mmol) was then added and the reaction mixture stirred for 2 h. The flask was placed into a dry ice/acetone bath (∼−78° C.) and BuLi (98 mL, 158 mmol, 1.6M in hexanes) was added dropwise. After 1 h, this reaction mixture was added to a solution of 2b (13.0 g, 30 mmol) in THF at −78° C. via cannula. After 2 h of stirring at −78° C., the flask was warmed to 0° C. Saturated NH$_4$Cl (150 mL) was added to quench the reaction. The organics were extracted using EtOAc (3×100 mL) and the combined organic layers were dried using MgSO$_4$, The solvent was removed under reduced pressure and the crude material was purified using flash silica gel chromatography (hexanes/EtOAc). 7.5 g (44%) of the desired material 2c was isolated. LC/MS=567.2 (M−H$^+$).

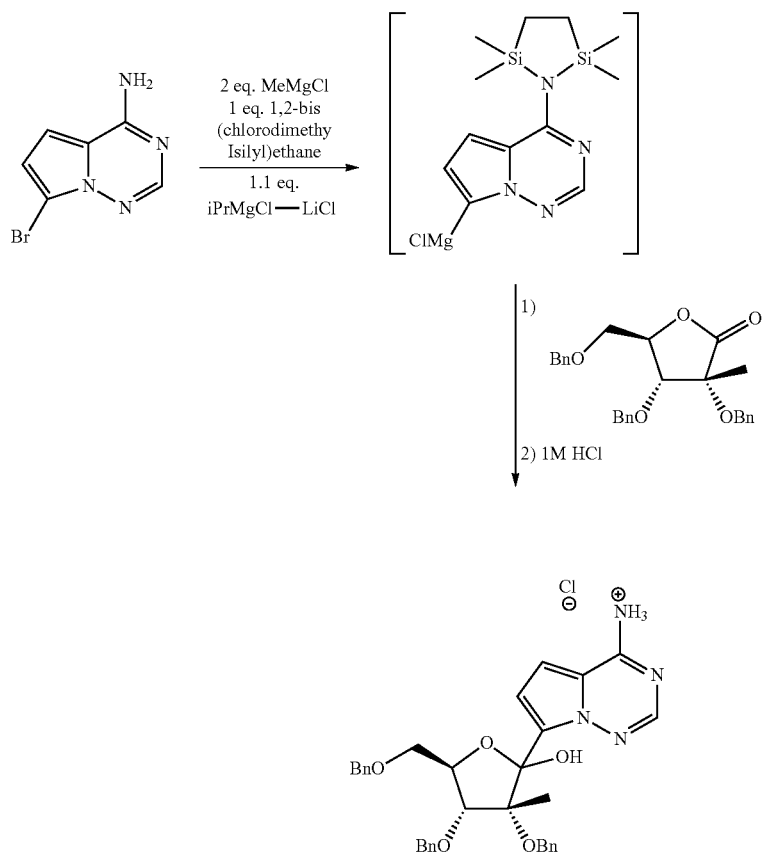

To a 500 ml jacketed 3-necked flask fitted with a thermocouple, vacuum/N₂ inlet and overhead stirring apparatus was added 7-bromo-pyrrolo[2,1-f][1,2,4]triazin-4-ylamine (20 g, 1.0 equiv., 94 mmol). This was suspended in dry THF (200 ml) and cooled to 0° C. To this was added dropwise 31 ml of MeMgCl solution (3M in THF, 1.0 equiv.). This proceeded with bubbling and a significant exotherm. The rate of addition was controlled to maintain internal temperature below 10° C. Following completion of addition and cooling to 0° C., 1,2-bis(chlorodimethylsilyl)ethane (20.2 g, 1.0 equiv.) was added in a single portion, with exotherm to about 5° C. Once the temperature had returned to 0° C., a second portion of 31 ml MeMgCl (3M in THF, 1.0 equiv.) was added as before. Once the temperature returned to 0° C., 80 ml of iPrMgCl.LiCl solution (1.3 M in THF, 1.1 equiv.) was added. The resulting dark solution was allowed to warm to room temperature, and conversion was checked by HPLC, with sample preparation in MeOH to provide the des-bromo heterocycle. Once the conversion of 7-bromo-pyrrolo[2,1-f][1,2,4]triazin-4-ylamine was >95% complete (5 hrs), the solution was cooled to 0° C., and a solution of 2b (40.6 g, 94 mmol) in 100 ml THF was added via cantina. The resulting orange solution was allowed to warm to room temperature and stirred overnight. After 12 hrs, the reaction was found to be complete by HPLC (sample prepared in 1120/MeCN 1:1). At this point 200 ml of 13% NH₄Cl solution was added and briskly stirred for 15 min. After this time, agitation was ceased, and the two layers were allowed to separate. The organic layer was then reduced to roughly 70 ml, and MeCN (100 ml) was added, followed by 300 ml 1M aqueous HCl solution. The resulting slurry was stirred at room temperature for 2 hrs, then filtered through a sintered glass funnel. The resulting solid was dried overnight under vacuum at 45° C. to give 2c. Yield 37.6 g (66%)

To a suspension of 7-bromo-pyrrolo[2,1-f][1,2,4]triazin-4-ylamine (2.14 g, 10 mmol) in 0.5 M LiCl solution of anhydrous THF (20 mL) was added TMSCl (2.53 mL, 20 mmol) and stirred at room temperature for 2 h. After cooling to −20° C., 3.0 M methyl magnesium chloride in diethyl ether (6.67 mL) was added dropwise while stirring. The mixture was then allowed to warm to room temperature over a period of 1 h. After cooling back to −20° C., Turbo Grignard (1.3 M in THF) was added in portions until the magnesium-bromine exchange was nearly complete (~15.5 mL over a period of 2 h). A solution of 2b (5.2 g, 12 mmol) was then added. The resulting mixture was allowed to warm to room temperature. The reaction was quenched with methanol, affording 2c.

Compound 3a and 3b

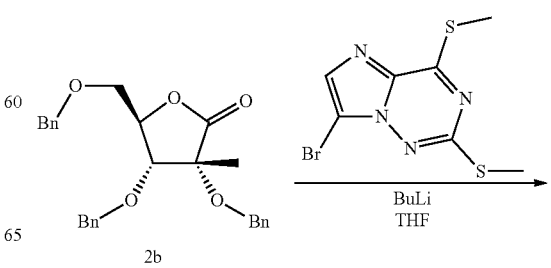

-continued

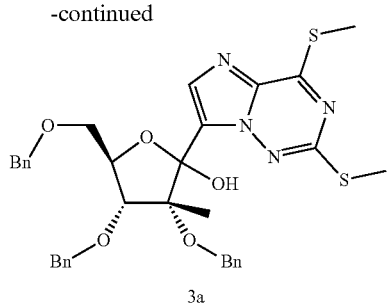

3a

To a suspension of 7-bromo-2,4-bis-methylsulfanyl-imidazo[2,1-f][1,2,4]triazine (prepared according to WO2008116064, 600 mg, 2.06 mmol) in anhydrous THF (6 mL) was dropwise added BuLi (1.6 M in hexanes, 1.75 mL, 2.81 mmol) at −78° C. The suspension became red brown solution after 5 min, and then a solution of 2b (810 mg, 1.87 mmol) in THF (0.6 mL) was added dropwise to the mixture. The mixture was then allowed to warm up to room temperature. After 30 min, saturated NH$_4$Cl was added to quench the reaction. The mixture was diluted with ethyl acetate; the organic layer was washed with brine and concentrated in vacuo. The residue was purified by silica gel column chromatography (~40% EtOAc/hexanes), affording 3a as an isomeric mixture (0.77 g, 64%). MS=645.2 (M+H$^+$).

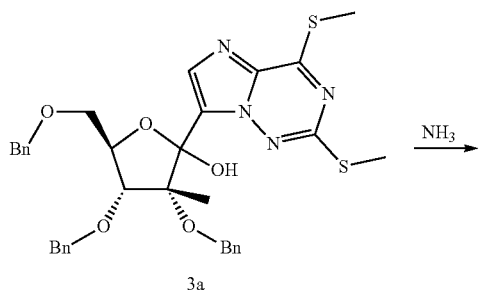

3a

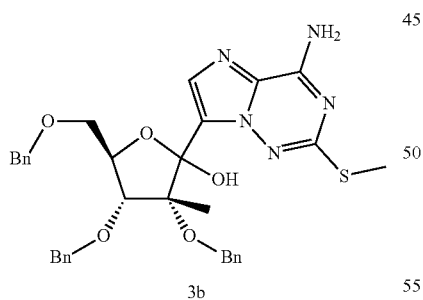

3b

Compound 3a (2.0 g, 3.10 mmol) was transferred to a steel bomb reactor, and cooled at −78° C. Liquid ammonia (~20 mL) was collected at −78° C. and added to the bomb reactor. The bomb reactor was tightly sealed and warmed up to room temperature. The mixture was then heated at 50° C. for 20 h. Complete conversion occurred. After the ammonia gas was vented, the residue was purified by silica gel column chromatography (EtOAc/hexanes), affording the product 3b as a pale yellow solid (1.78 g, 94%). MS=614.3 (M+H$^+$).

Compound 4

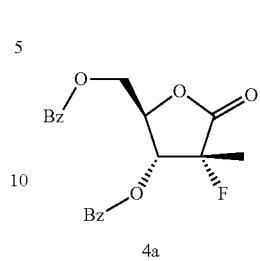 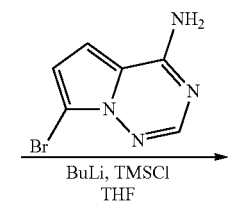

4a

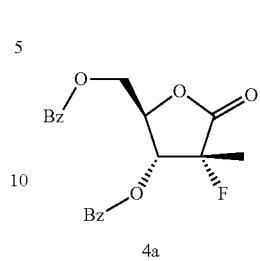

4

To a suspension of 7-bromo-pyrrolo[2,1-f][1,2,4]triazin-4-ylamine (2.13 g, 10 mmol) in THF (20 mL) was added TMSCl (2.66 mL, 21 mmol) and stirred at room temperature for 16 h under argon. After cooling to −78° C. solution of BuLi (1.6 M, 21 mL, 33 mmol) in hexanes was added dropwise. The mixture was stirred for 1 h at the same temperature. A solution of 4a (prepared according to WO 200631725, 4.46 g, 12 mmol) in THF (10 mL) was then added. After stirring for 2 h at −78° C., saturated ammonium chloride was added to quench the reaction. The mixture was extracted with ethyl acetate. The organic extract was concentrated in vacuo. The residue was purified by silica gel chromatography (ethyl acetate/hexanes), affording 4 as a yellow solid (1.6 g, 32%). MS=507.1 (M+H$^+$).

Alternative Procedure for Compound 4 using 1,2-bis-[(chlorodimethyl)silanyl]ethane Instead of Chlorotrimethylsilane To a suspension of 7-bromo-pyrrolo[2,1-f][1,2,4]triazin-4-ylamine (500 mg, 2.35 mmol) in THF (6.5 mL) was added BuLi (1.6 M in hexanes, 1.6 mL) at −78° C. After 30 min., a solution of 1,2-bis-[(chlorodimethyl)silanyl]ethane (538 mg, 2.4 mmol) in THF (1.2 mL) was added. After 45 min., BuLi (1.6 mL) was added. After an additional 30 min., BuLi (1.5 mL) was added. After 30 min., a solution of 4a (610 mg, 1.64 mmol) in THF (2 mL) was then added dropwise. The resulting mixture was stirred at −78° C. for 2 h under argon. Acetic acid (0.7 mL) was added dropwise to quench the reaction, followed by addition of saturated ammonium chloride. The mixture was extracted with ethyl acetate. The organic extract was concentrated in vacuo. The residue was purified by silica gel chromatography (ethyl acetate/hexanes), affording 4 (320 mg, 40%). The starting 4a was also recovered (350 mg) from the chromatography.

Compound 5

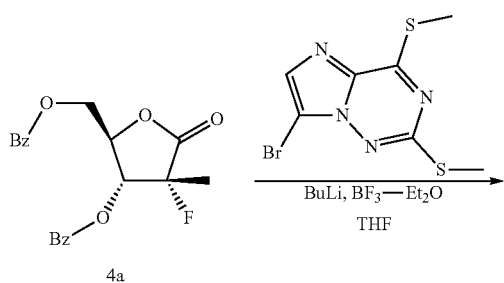

To a suspension of 7-bromo-2,4-bis-methylsulfanyl-imidazo[2,1-f][1,2,4]triazine (prepared according to WO2008116064, 500 mg, 1.72 mmol) in anhydrous THF (5 mL) was dropwise added BuLi (1.6 M in hexanes, 1.61 mL, 2.41 mmol) at −78° C. The suspension became red brown solution after 5 min, and then a mixture of 4a (675 mg, 1.81 mmol) and boron trifluoride etherate (2.40 mL, 1.89 mmol) in THF (5 mL) was added dropwise to the mixture. After stirring for 2 h at −78° C., saturated NH$_4$Cl was added to quench the reaction. The mixture was diluted with ethyl acetate; the organic layer was washed with brine and concentrated in vacuo. The residue was purified by silica gel column chromatography (EtOAc/hexanes), affording 5 as a rich yellow foam (650 mg, 67%). $^1$H NMR (400 MHz, CDCl$_3$): δ 8.13 (d, 2H), 8.03 (d, 2H), 7.81 (d, 1H), 7.59 (t, 1H), 7.45 (in, 3H), 7.36 (t, 2H), 6.40 (brs, 1H), 6.01 (dd, 1H), 4.78 (m, 2H), 4.60 (dd, 1H), 2.68 (s, 3H), 2.45 (s, 3H), 1.62 (d, 3H). $^{19}$F NMR (376 MHz, CDCl$_3$): δ −167.5. MS=585.1 (M+H$^+$).

Compound 6

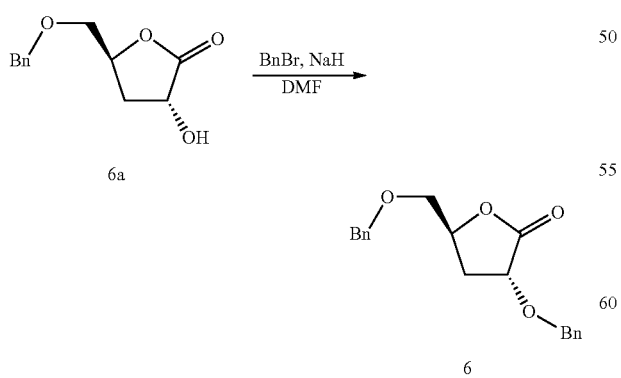

To a suspension of sodium hydride (about 60% suspension in oil, 400 mg, 10 mmol) in DMF (about 20 mL) is added dropwise a solution of 6a (prepared according to *J.* *Chem. Soc., Perkin Trans* 1, 1991, 490, about 2.2 g, 10 mmol) in DMF (10 mL) at about 0° C. The mixture is then stirred at about room temperature until the gas evolution ceases. Benzyl bromide (about 1 eq.) is added and the mixture is stirred for about 1 to 16 h at about 0 to 100° C. The mixture is poured into ice-water (300 mL) and extracted with ethyl acetate. The organic extract may be purified by silica gel chromatography to give 6.

Compound 7

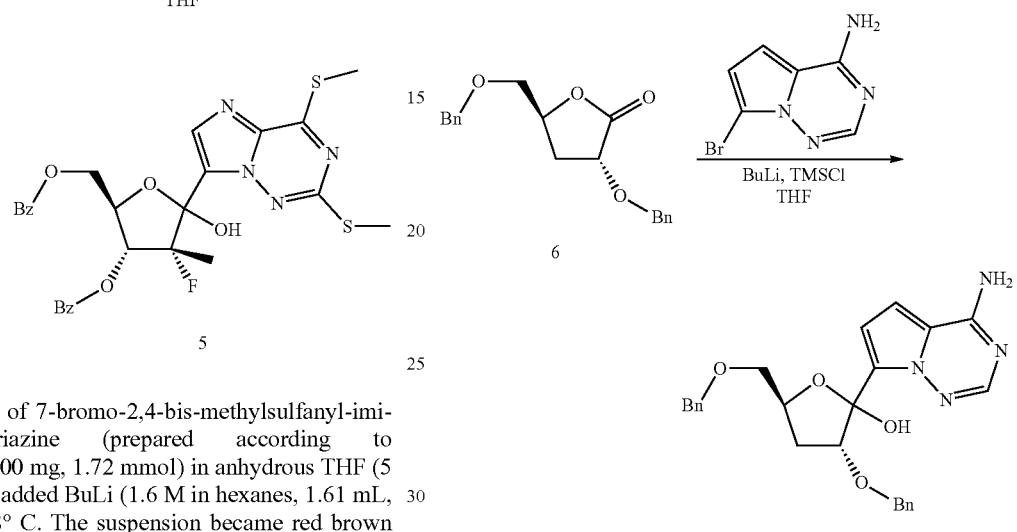

To a suspension of 7-bromo-pyrrolo[2,1-f][1,2,4]triazin-4-ylamine (about 10 mmol) in THF (about 20 mL) is added TMSCl (about 21 mmol) and the mixture is stirred at about room temperature for about 1 to 16 h under argon. After cooling to about −78° C., a solution of BuLi (about 1.6 M in hexanes, about 33 mmol) is added dropwise. The mixture is stirred for about 1 to 5 h at about the same temperature. A solution of 6 (about 12 mmol) in THF (about 10 mL) is then added. After stirring for about 2 h at about −78° C., saturated ammonium chloride is added to quench the reaction. The mixture is extracted with ethyl acetate. The organic extract is concentrated in vacuo. The residue may be purified by silica gel chromatography (ethyl acetate/hexanes), to give 7.

Lactone B

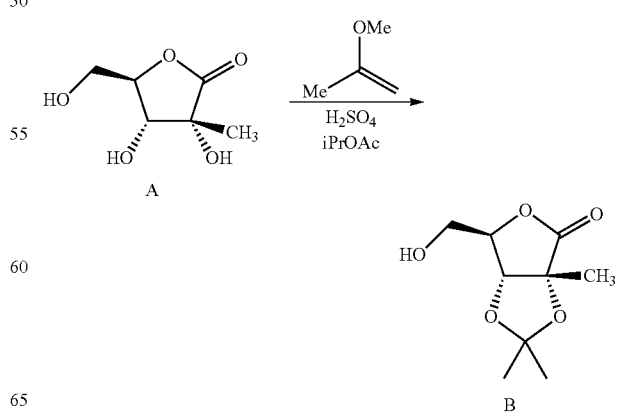

20.0 g lactone A (123.4 mmol) is suspended in 200 mL iPrOAc and to this mixture is added 65 µL H₂SO₄ (1.23 mmol, 0.01 equiv.). This mixture is cooled to 15 CC. To the cooled mixture is added 11.8 mL 2-methoxypropene (123.4 mmol, 1.0 equiv.) over a period of 2 h. Upon completion of addition the mixture is allowed to stir for 12 h at 15° C. Following age, the mixture is warmed to 20° C. and another 6.0 mL 2-methoxypropene (0.5 equiv) is added to the reaction mixture. The mixture is aged with stirring at 20° C. for an additional 7 h. Following age, The solids are removed by filtration, rinsed with 100 mL iPrOAc. The combined organic washes are washed 1× with 100 mL water, and the organic layer is concentrated to a colorless oil. This oil is diluted with 100 mL heptane, and upon concentration affords colorless solids, which are collected by filtration, and rinsed with 100 mL heptane giving 8.36 g (36% yield) of desired compound, (M+H)/Z=203.

Lactone C

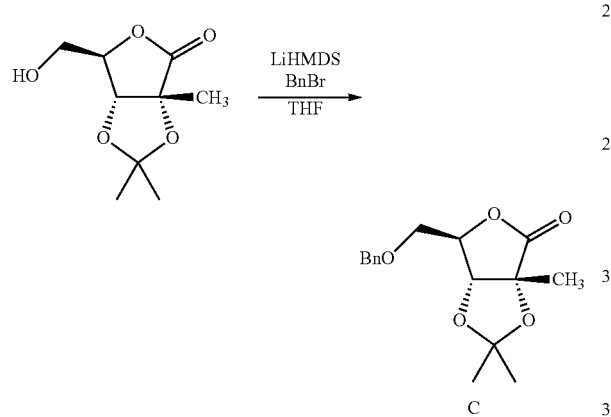

0.50 g lactone acetonide B (2.47 mmol), 0.294 mL benzyl bromide (2.47 mmol, 1.0 equiv.) and 5.0 mL tetrahydrofuran are combined and the mixture is cooled to 0° C. To the cooled mixture is added 2.47 mL of a 1.0 M LiHMDS in THF solution (2.47 mmol, 1.0 equiv.) over a period of 2.0 h. The mixture is allowed to slowly warm to 22° C., and is aged with stirring over 16 h. Following age, to the mixture is added 5.0 mL water, and the layers are split. The organic layer is concentrated, and the oil is purified by SiO₂ chromatography (0→40% EtOAc/Hexanes) affording 88.4 mg desired product as a colorless oil, (M+H)/Z=293.

Lactone D

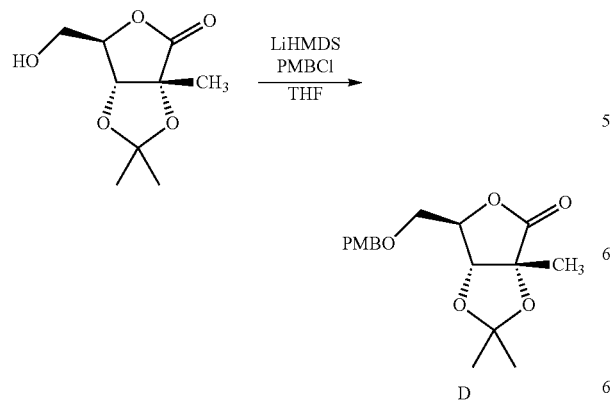

0.50 g lactone acetonide B (2.47 mmol), 0.335 mL PMBBr (2.47 mmol, 1.0 equiv.) and 5.0 mL tetrahydrofuran are combined and the mixture is cooled to 0° C. To the cooled mixture is added 2.0 mL of a 1.0 M LiHMDS in THF solution (2.0 mmol, 0.8 equiv.) over a period of 2.0 h. The mixture is allowed to slowly warm to 22° C., and is aged with stirring over 16 h. Following age, the mixture is cooled to 0 C and to the cooled mixture is added the remaining 0.5 mL 1.0 M LiHMDS/THF solution (0.2 equiv.) over a period of 40 min. Following completion of base addition, the mixture is warmed to 23 C and aged for 1 h with stirring. Following age, the mixture is cooled to 0° C., and to the cooled mixture is added 0.6 mL 4 N sulfuric acid solution, followed by 0.6 mL water, and the resulting layers are separated (aq. pH ~9). The combined organic washes are concentrated to a colorless oil, and the oil is purified by SiO₂ chromatography (0→40% EtOAc/Hexanes) affording 23.4 mg desired product D as a colorless oil, (M+H)/Z=323.

Lactone E

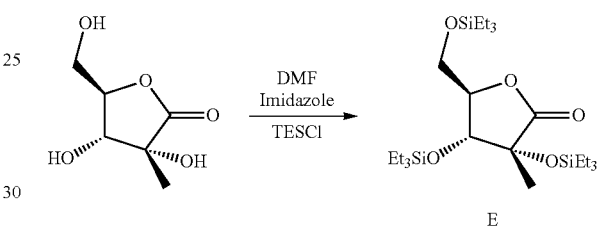

Lactone A (4.82 g, 29.7 mmol, 1.0 eq) was dissolved in 50 mL DMF. Imidazole (8.1 g, 119 mmol, 4 eq) was added. Triethylsilylchloride (17.9 g, 119 mmol, 4 eq) was then added over ~5 min and the mixture heated to 50° C. 2 mL methanol was added to quench the reaction. 50 mL toluene was added and the mixture washed sequentially with 40 mL water, 2×30 mL 5% NaHCO₃, and 25 mL sat'd. NaCl. The organics were dried over Na₂SO₄, filtered and concentrated to 14 g of a crude oil. The oil was purified by silica gel chromatography eluting with 10% EtOAc:hexanes to yield 9 g of Lactone E, (M+H)/Z=505.

Lactone F

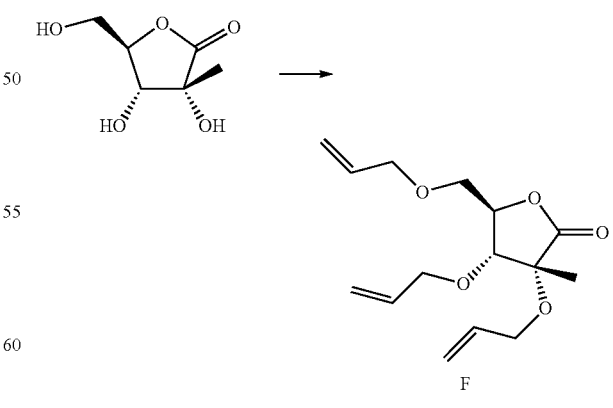

To a flask was charged NaH (1.60 g) and N,N-dimethylformamide (15 mL). The solution was cooled in an ice bath and lactone A (1.56 g) was added in DMF (3 mL) followed by a wash with DMF (1 mL) and the ice bath was removed.

After 1 h, DMF (5 mL) was added to promote better stirring. The mixture was placed in an ice bath and allyl bromide (3.7 mL) was added and the ice bath removed. After stirring overnight the mixture was cooled in an ice bath and the reaction mixture carefully quenched with water (10 mL). To the mixture was added EtOAc (65 mL) and after agitation and separation the organics were washed with water and brine. The organics were dried over a mixture of Na₂SO₄ and MgSO₄, concentrated, and column purified on silica gel to give 1.1 g of the tri-allyl derivative, (M+H)/Z=283.
Lactone G

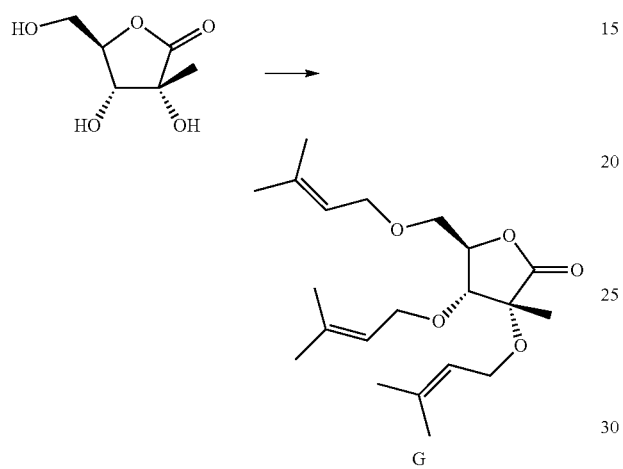

G

To a flask was charged NaH (1.7 g) and N,N-dimethylformamide (30 mL). The solution was cooled in an ice bath and Lactone A (1.57 g) was added in DMF (4 mL) followed by a wash with DMF (1 mL). The ice bath was removed and after 1.5 h the reaction mixture was cooled in an ice bath and 3,3-dimethylallyl bromide (5.2 mL) was added. The ice bath removed and the reaction left to stir overnight. The reaction mixture was cooled to 0° C. and was quenched with saturated NH₄Cl (3 mL) followed by diluting with water (27 mL) and EtOAc (100 mL). The organics were then washed with water and brine (30 mL each) and then dried over Na₂SO₄, filtered and concentrated. The residue was purified by column chromatography on silica gel giving 1.42 g (40%) of the tri-prenyl Lactone G, (M+H)/Z=367.
Lactone H

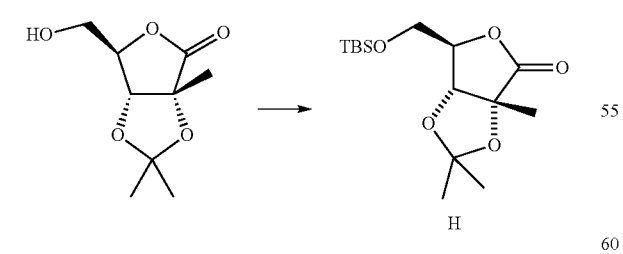

H

To a flask was charged the Lactone B (1.99 g) and DMF (20 mL). To the solution was added imidazole (1.00 g) and TBSCl (1.93 g) and the mixture was left to stir overnight. The next day water (20 mL) and EtOAc (50 mL) were added. The organics were then separated and washed with brine (20 mL), dried over Na₂SO₄, filtered and concentrated. The residue was purified by column chromatography on silica gel giving 2.75 g (88%) of the Lactone H, (M+H)/Z=317.
Compound 9

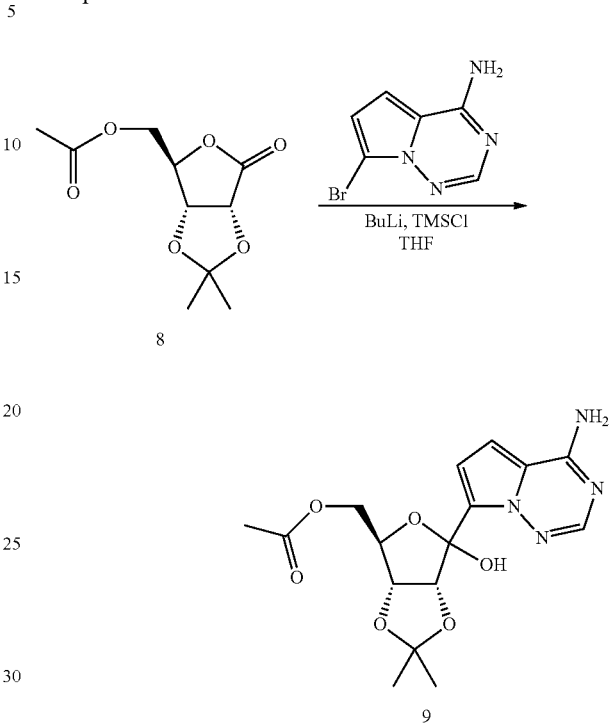

8

9

Compound 9 may be synthesized in the same manner as 1c by substituting Compound 8 (Ogura, et al. *J. Org, Chem.* 1972, 37, 72-75) for 1b in the reaction.
Compound 11

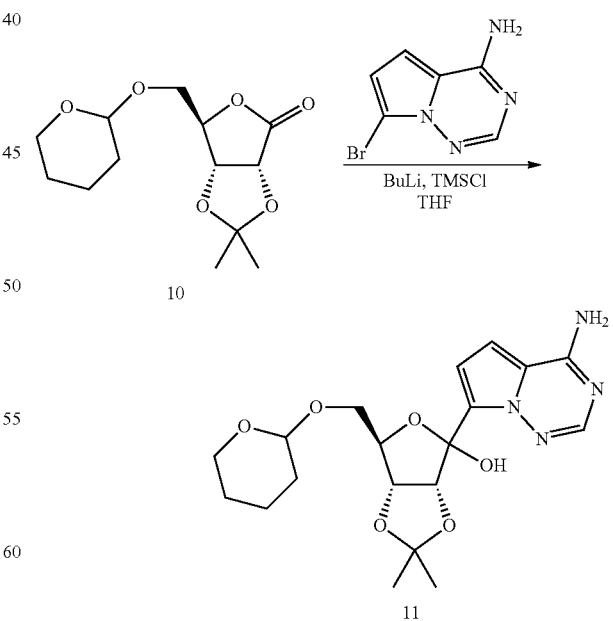

10

11

Compound 11 may be synthesized in the same manner as 1c by substituting Compound 10 (Ogura, et al. *J. Org. Chem.* 1972, 37, 72-75) for 1b in the reaction.

Compound 13

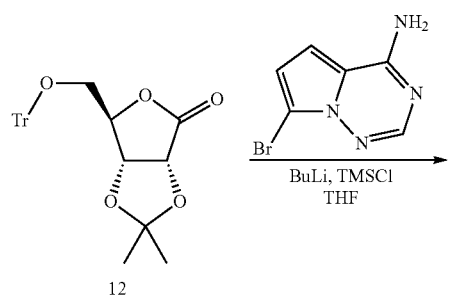

Compound 13 may be synthesized in the same manner as 1c by substituting Compound 12 (Camps, et al.; *Tetrahedron* 1982, 38, 2395-2402) for 1b in the reaction.

Compound 14

To 7-bromo-pyrrolo[2,1-f][1,2,4]triazin-4-ylamine (0.501 g) and THF (31.5 mL) was added 1,2-bis(chloromethylsilyl)ethane (0.518 g). To the cloudy solution was added NaH (60% in mineral oil, 0.235 g). After 10 minutes the solution was cooled in a −40° C. bath and nBuLi (2.16 Min hexanes, 3.6 mL) was added. After 13 min the lactone (1.031 g) was added in THF (3 mL) followed by a wash with 0.1 mL of THF. After 3 h the reaction mixture was at −20° C. and was quenched with saturated NH$_4$Cl (3 mL) followed by the addition of water (7 mL). The solution was left to warm to room temperature overnight. The next day EtOAc (32 mL) was added and after separating the organics they were washed with water and brine (10 mL each). The organics were dried over Na$_2$SO$_4$, filtered, concentrated and the resulting residue purified by column chromatography on silica gel giving 0.567 g (48%) of the tri-prenyl protected lactol 14, (M+H)/Z=501.

Compound 15

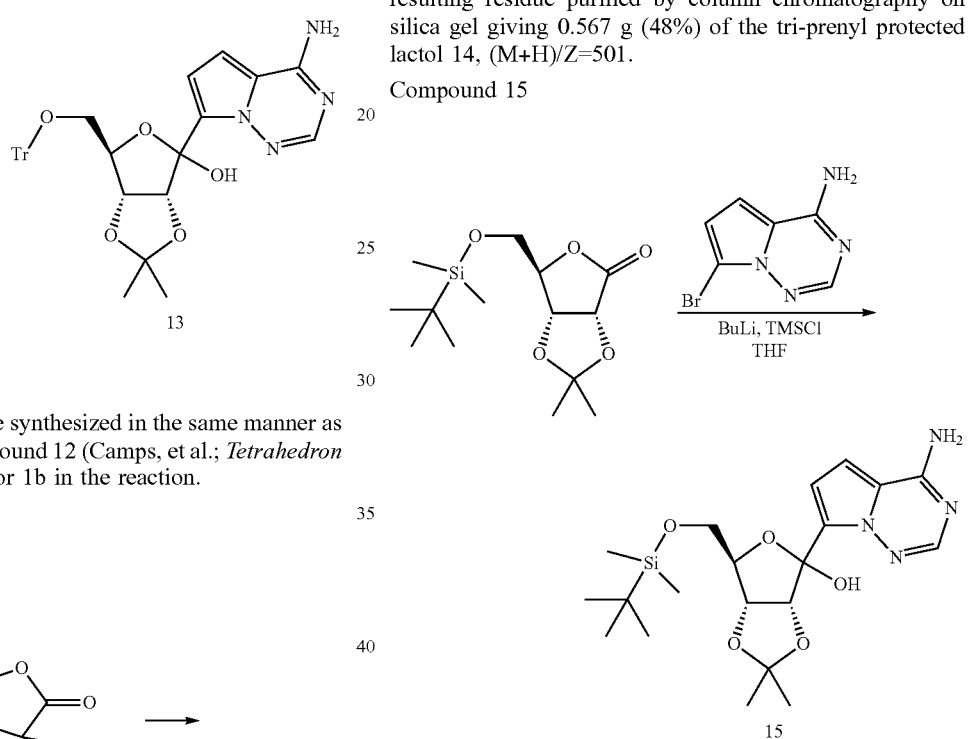

Compound 15 may be synthesized in the same manner as 1c by substituting the t-butylsilyl lactone depicted (Alessandrini, et al.; *J. Carbohydrate Chem.* 2008, 27, 322-344) for 1b in the reaction.

Compound 17

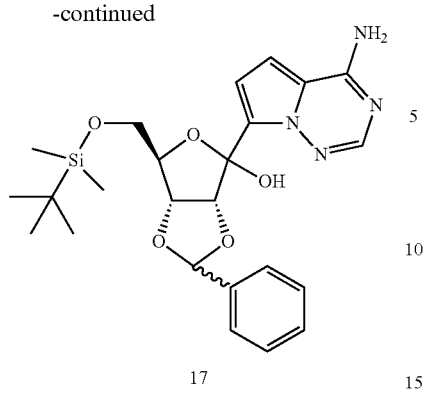

17

Compound 17 may be synthesized in the same manner as 1e by substituting Compound 16 (Alessandrini, et al.; *J. Carbohydrate Chem.* 2008, 27, 322-344) for 1b in the reaction.

Compound 19

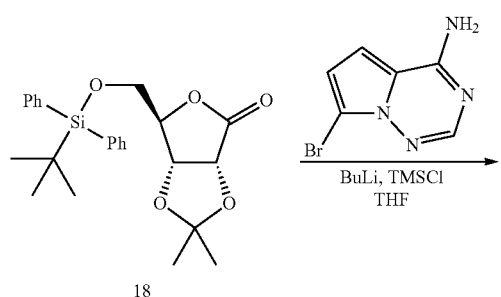

18

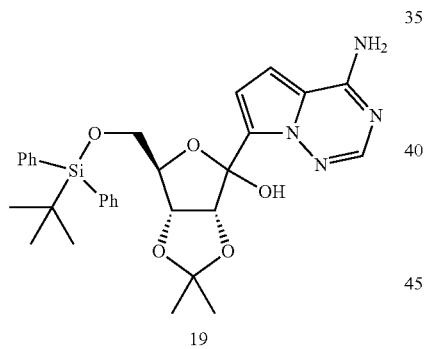

19

Compound 19 may be synthesized in the same manner as 1e by substituting Compound 18 (Piccirilli, et al.; *Helvetica Chimica Acta* 1991, 74, 397-406) for 1b in the reaction.

Compound 20

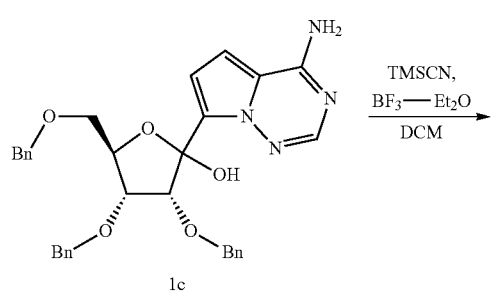

1c

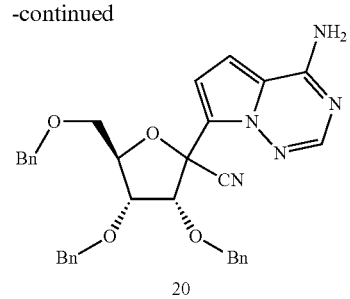

20

Compound 1c (0.28 g, 0.51 mmol) was dissolved in anhydrous dichloromethane (10 mL) and placed under nitrogen. Trimethylsilyl cyanide (0.35 mL) was added and the mixture was cooled to 0° C. After stirring for 10 min., boron trifluoride etherate (50 uL) was added and the reaction was allowed to warm to room temperature. When the reaction was complete by LC/MS, triethylamine was added to quench the reaction and solvents were removed by rotary evaporation. The residue was taken up in dichloromethane and loaded onto a silica gel column. A mixture of anomers was eluted using a gradient of 0-75% ethyl acetate and hexanes; 37% yield of 20. $^1$H-NMR (300 MHz, CD$_3$CN): δ 3.61-3.90 (n, 2H), 4.09-4.19 (m, 2H), 4.30-4.88 (m, 7H), 4.96 (d, 0.5H), 5.10 (d, 0.5H), 6.41 (bs, 2H), 6.73-6.78 (m, 1H), 6.81-6.88 (an, 1H), 7.17 (m, 2H), 7.39 (m, 13H), 7.86 (s, 0.5H), 7.93 (s, 0.5H).

Alternative Preparation of Compound 4 Using Trimethylsilyl Triflate as the Lewis Acid

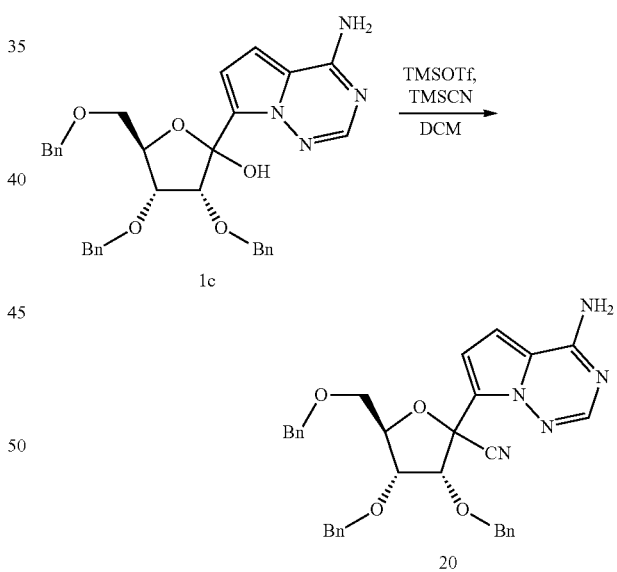

Compound 1c (1.1 g, 2.0 mmol) was dissolved in anhydrous dichloromethane (35 mL) and placed under nitrogen. Trimethylsilyl cyanide (1.21 mL, 9.1 mmol) was added and the mixture was cooled to 0° C. After stirring for 10 min., trimethylsilyl triflate (2.0 mL, 11 mmol) was added. When the reaction was complete by LC/MS (~2 h), dichloromethane (70 mL) was added to dilute followed by saturated sodium bicarbonate (70 mL). The mixture was stirred for 10 min. and the organic layer was collected by separatory funnel. The aqueous layer was extracted with dichloromethane, which was combined with the first organic extract. The solvents were removed by rotary evaporation. The residue was taken up in dichloromethane and loaded onto a silica gel column. A mixture of anomers was eluted using a gradient of 0-75% ethyl acetate and hexanes; 90% yield of 20.
Compound 21

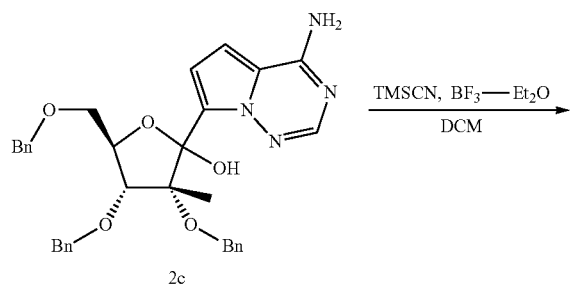

To a solution of compound 2c (1 g, 1.77 mmol) in CH$_2$Cl$_2$ (20 mL) at 0° C. was added TMSCN (1.4 mL, 10.5 mmol) and BF$_3$-Et$_2$O (1 mL, 8.1 mmol). The reaction mixture was stirred at 0° C. for 0.5 h, then at room temperature for additional 0.5 h. The reaction was quenched with NaHCO$_3$ at 0° C., and diluted with CH$_3$CO$_2$Et. The organic phase was separated, washed with brine, dried over Na$_2$SO$_4$, filtered and concentrated. The residue was purified by chromatography on silica gel, eluted with CH$_3$CO$_2$Et-hexanes (1:1 to 2:1), to give the desired compound 21 (620 mg, 61%). MS 576.1 (M+H$^+$).

Alternative Preparation of Compound 21

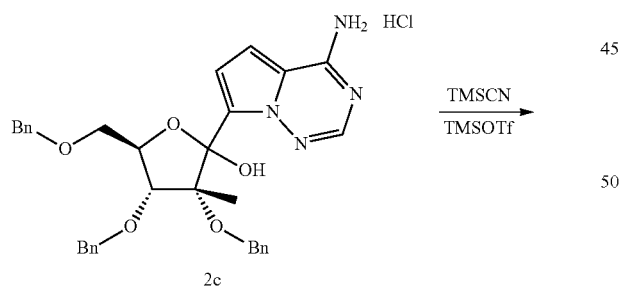

A flask was charged with 2c. HCl (53.2 g, 1 eq) and dichloromethane (530 mL). The slurry was cooled to −16° C. and TMSOTf (17.5 mL, 1.1 eq) was charged over 2 minutes while maintaining an internal temperature <−5 CC; the solution became homogeneous. When the reaction mixture was −14° C. the TMSCN (1.34 mL, 2.3 eq) was charged over 2 minutes. After 1 h, a solution of 10% (w/w) potassium carbonate/water (480 mL) was added followed by 45% (w/w) potassium hydroxide/water (53 mL) while maintaining a temperature of <0° C. The mixture was warmed to 20° C. and after the layers separated the organics were exchanged with acetonitrile followed by a wash with heptanes. The acetonitrile organics were concentrated and exchanged with DCM (200 mL) and concentrated to a foam giving 48.6 g (95%) of Compound 21, (M+H)/Z=576.

Compound 22

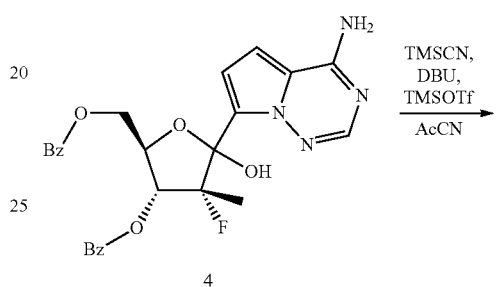

To a solution of compound 4 (50 mg, 0.1 mmol) and TMSCN (67 uL, 0.5 mmol) in acetonitrile (2.0 mL) at 0° C. was added TMSOTf (91 uL, 0.5 mmol). The reaction mixture was stirred at room temperature for 1 h, then at 65° C. for 3 d. The reaction was quenched with saturated NaHCO$_3$ at room temperature, and diluted with CH$_3$CO$_2$Et. The organic phase was separated, washed with brine, dried over Na$_2$SO$_4$, filtered and concentrated. The residue was purified by RP-HPLC (acetonitrile/water), to give the desired compound 22 (28 mg, 54%). MS=516.1 (M+H$^+$).

Alternative Preparation of Compound 22

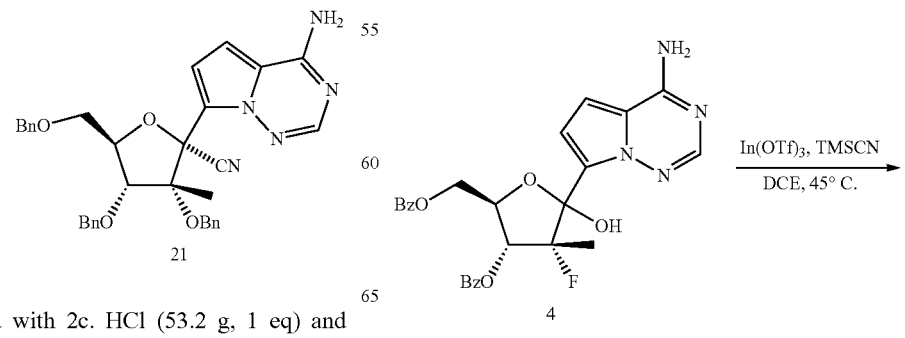

-continued

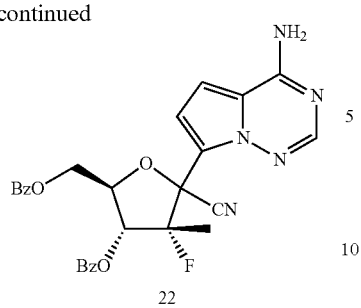

22

To a stirred solution of 4 (5 g, 10 mmol) in 1,2-dichloroethane (300 mL, 0.04M) under argon was added In(OTf)$_3$ (16.8 g, 30 mmol) and stirred for 5 min. The reaction mixture was then heated to 45° C. TMSCN (8.0 mL, 60 mmol) was added quickly. The reaction was allowed to progress overnight. The solvent was evaporated off, and the crude mixture was purified by silica gel chromatography (with Hex:EtOAc as eluent), affording compound 22 (~5 g). MS [M+H$^+$]=516.3

Compound 23

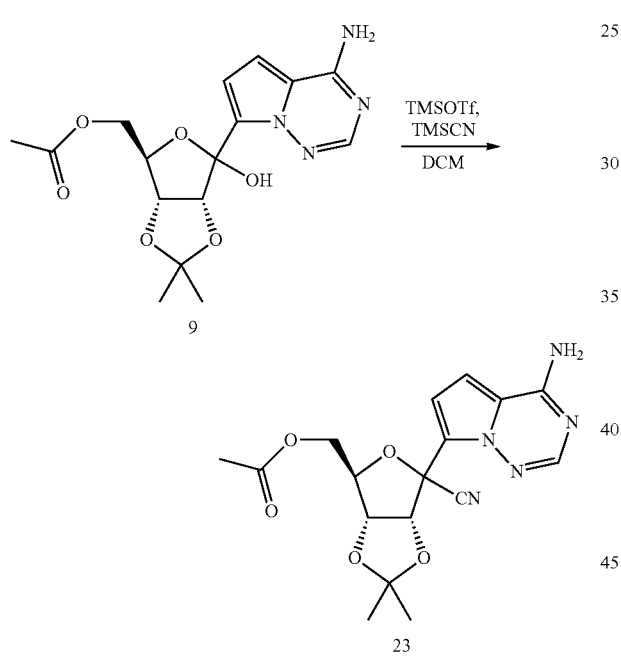

Compound 23 may be prepared in the same manner as Compound 20 by substituting Compound 9 for 1c.

Compound 24

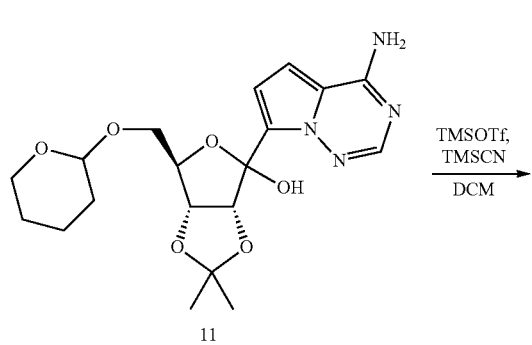

-continued

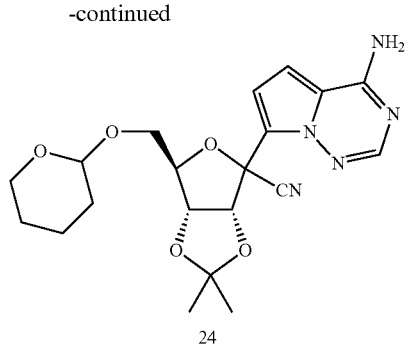

24

Compound 24 may be prepared in the same manner as Compound 20 by substituting Compound 11 for 1c.

Compound 25

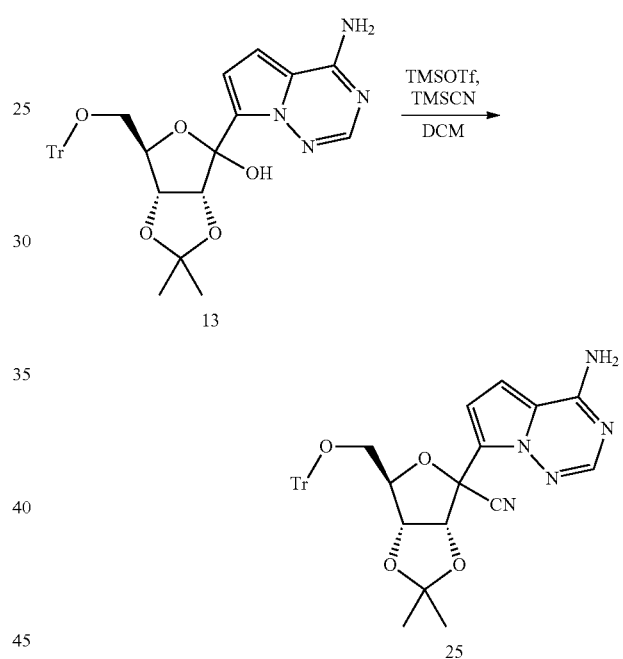

Compound 25 may be prepared in the same manner as Compound 20 by substituting Compound 13 for 1c.

Compound 26

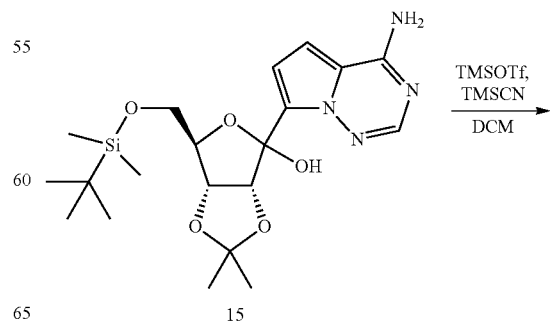

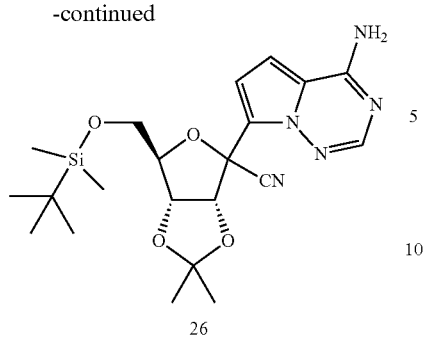

26

Compound 26 may be prepared in the same manner as Compound 20 by substituting Compound 15 for 1c.

Compound 27

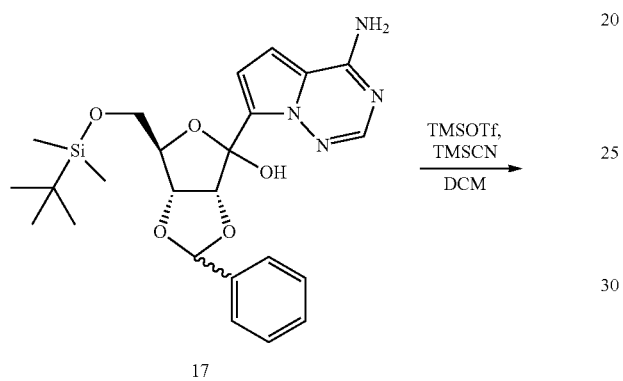

17

27

Compound 27 may be prepared in the same manner as Compound 20 by substituting Compound 17 for 1c.

Compound 28

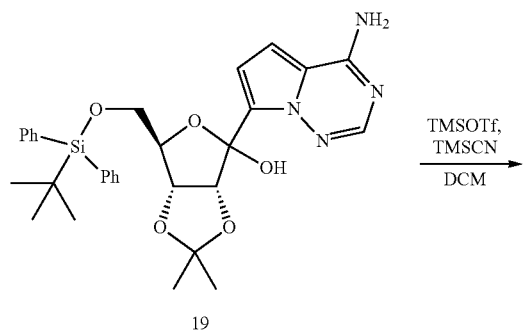

19

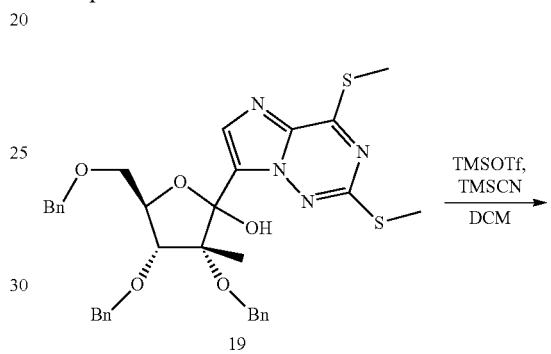

28

Compound 28 may be prepared in the same manner as Compound 20 by substituting Compound 19 for 1c.

Compound 29

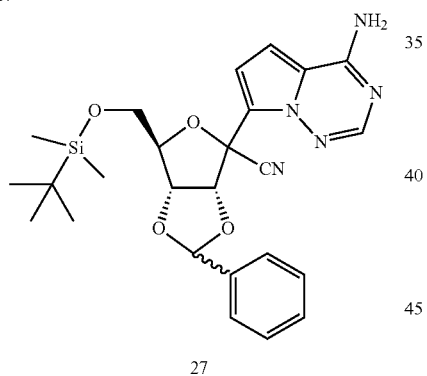

19

29

Compound 29 may be prepared in the same manner as Compound 20 by substituting Compound 3a for 1c.

Compound 30

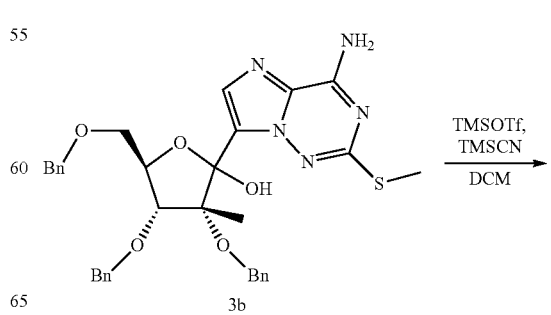

3b

-continued

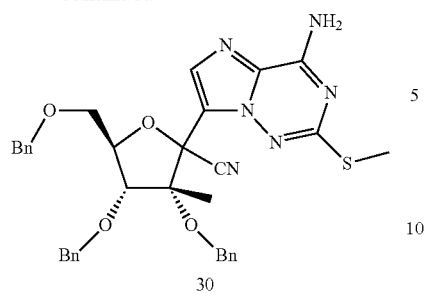
30

Compound 30 may be prepared in the same manner as Compound 20 by substituting Compound 3b for 1c.
Compound 31

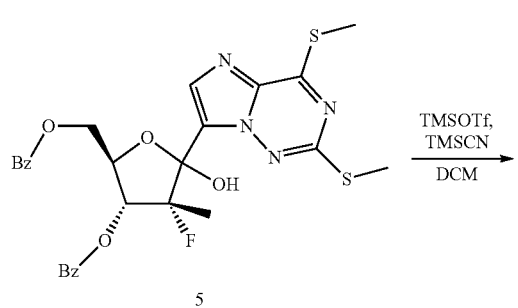
5

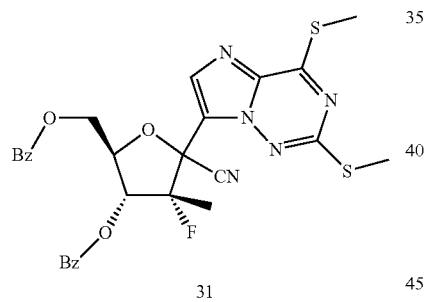
31

Compound 31 may be prepared in the same manner as Compound 20 by substituting Compound 5 for 1c.

Alternative Preparation of Compound 31

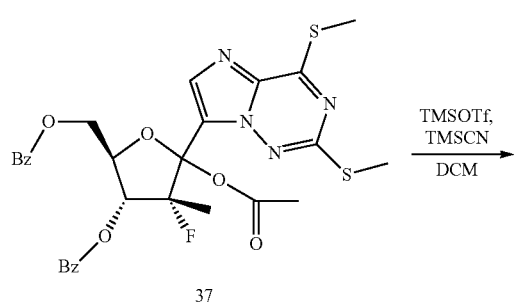
37

-continued

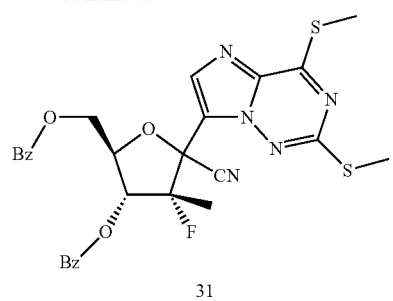
31

Compound 31 may also be prepared in the same manner as Compound 20 by substituting Compound 37 for 1c.
Compound 32

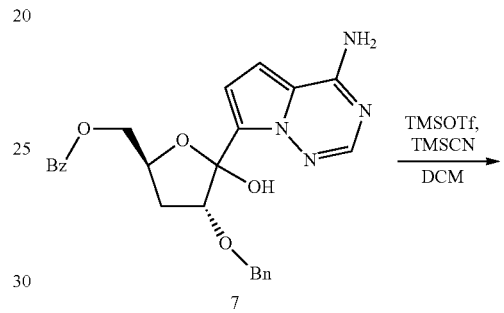
7

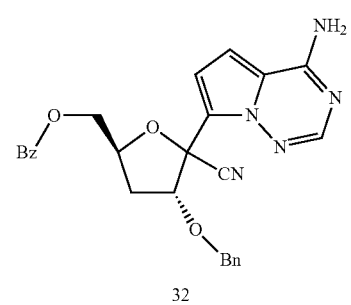
32

Compound 32 may be prepared in the same manner as Compound 20 by substituting Compound 7 for 1c.
Compound 33

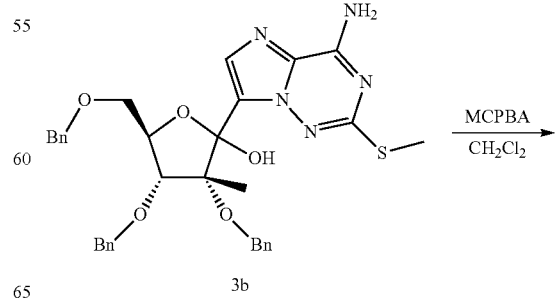
3b

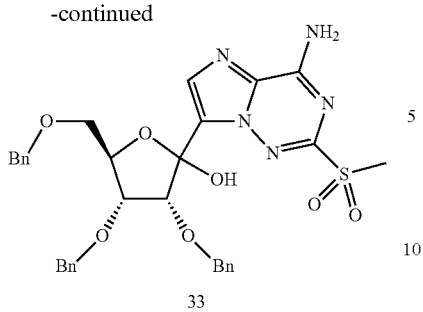

33

A solution of MCPBA (1.55 g, 8.96 mmol) in dichloromethane (20 mL) was dropwise added to a solution of 3b (2.5 g, 4.07 mmol) in dichloromethane (40 mL) while stirring. The resulting mixture was stirred at room temperature until complete disappearance of the starting material. After 3.5 h, the solvent was removed under reduced pressure and the crude material was purified using flash silica gel chromatography (hexanes/EtOAc). 2.0 g (77%) of the desired material 33 was isolated. LC/MS=646.2 (M+H$^+$).

Compound 34

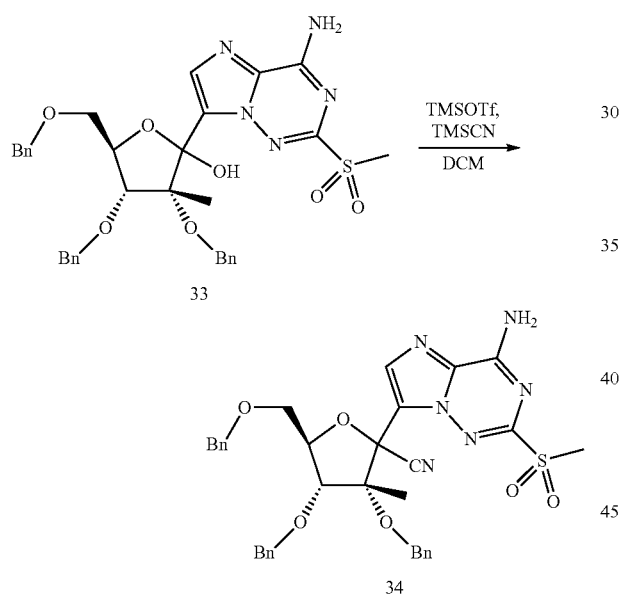

Compound 34 may be prepared in the same manner as Compound 20 by substituting Compound 33 for 1c.

Compound 35

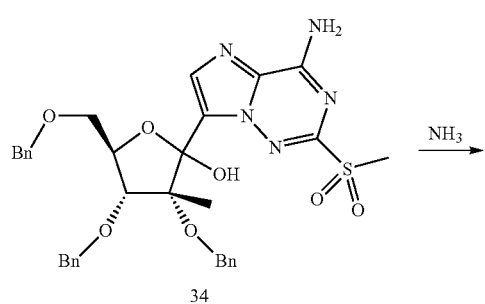

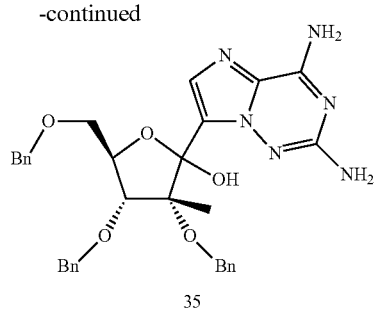

35

Compound 34 (2.0 g, 3.10 mmol) was dissolved in dichloromethane (15 mL) in a round bottom flask (50 mL) and then transferred to a steel bomb reactor. The solvent was removed under a positive flow of N$_2$ (g) and the solid material was treated with liquid NH$_3$ at −78° C. The tightly sealed bomb reactor was placed into a pre-heated oil bath at 110° C. and the reaction continued to proceed for 14 h. 1.8 g (100%) of the desired material 35 was isolated using MeOH and was used as is for the next reaction. LC/MS=583.3 (M+H$^+$)

Compound 36

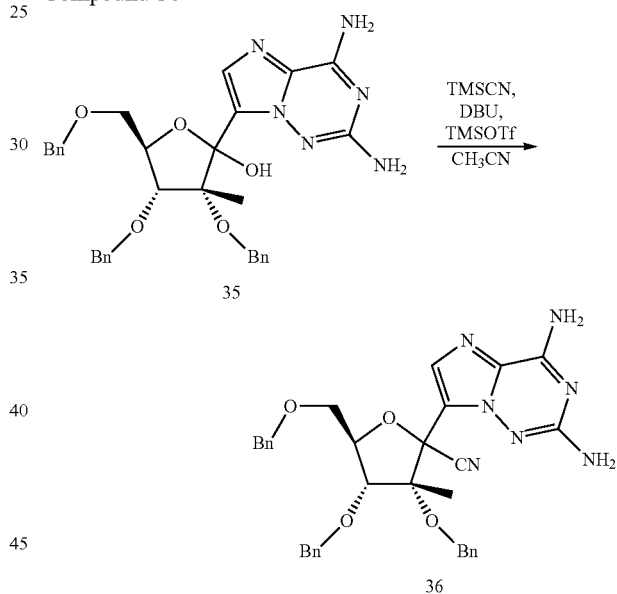

To a dry, argon purged round bottom flask (50 mL) were added 3,4-bis-benzyloxy-5-benzyloxymethyl-2-(2,4-diamino-imidazo[2,1-f][1,2,4]triazin-7-yl)-3-methyl-tetrahydro-furan-2-ol 35 (800 mg, 1.37 mmol) and anhydrous MeCN (18 mL). The flask was cooled to 0° C. and DBU (1.02 mL, 6.85 mmol) was added. After 5 min of stirring, TMSOTf (1.49 mL, 8.22 mmol) was added to the flask followed by dropwise addition of TMSCN (1.10 mL, 8.22 mmol). The reaction mixture was allowed to warm to room temperature and the flask was then equipped with a reflux condenser and placed into a vessel preheated at 65° C. After 2 days of stirring, the flask was cooled to room temperature and then placed into an ice bath and the reaction was quenched with saturated NaHCO$_3$, EtOAc (3×10 mL) was used to extract the organic material and the combined organic layers were washed with brine (3×10 mL) and dried using MgSO$_4$. The solvent was removed under reduced pressure and the crude material was purified using flash chromatography (hexanes/EtOAc). 750 mg (93%) of the desired material 36 was isolated. LC/MS=592.3 (M+H$^+$).

Compound 37

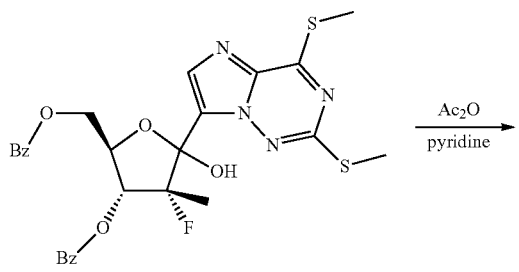

5

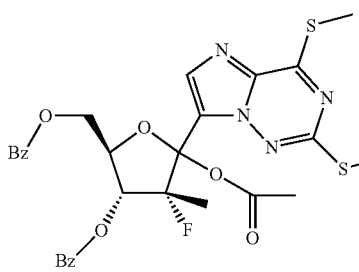

37

To a solution of 5 (300 mg, 0.51 mmol) in pyridine (1.5 mL) was added acetic anhydride (0.29 mL, 3.08 mmol) and stirred at 120° C. for 16 h. After cooling to room temperature, ethyl acetate and water were added. The ethyl acetate layer was taken, washed with dilute HCl followed by saturated ammonium chloride, dried over magnesium sulfate, and concentrated. The residue was purified by silica gel chromatography (dichloromethane/ethyl acetate), affording two stereoisomers of 37.

For fast moving isomer of 37; 26 mg, $^1$H NMR (400 MHz, CDCl$_3$): δ 8.39 (d, J=4.8 Hz, 1H), 8.00 (d, J=7.2 Hz, 2H), 7.98 (d, J=7.2 Hz, 2H), 7.59 (t, J=7.2 Hz, 1H), 7.51 (t, J=7.2 Hz, 1H), 7.45 (t, J=7.2 Hz, 2H), 7.38 (t, J=7.2 Hz, 2H), 5.39 (dd, J=8.2, 26.4 Hz, 1H), 5.61 (m, 1H), 4.77 (dd, J=2.6, 12.2 Hz, 1H), 4.25 (dd, J=4.8, 12.4 Hz, 1H), 2.68 (s, 3H), 2.61 (s, 3H), 1.68 (d, J=22.8 Hz, 3H), 1.54 (s, 3H). MS=627.0 (M+H$^+$).

For slow moving isomer of 37; 81 mg, $^1$H NMR (400 MHz, CDCl$_3$): δ 8.06 (d, J=7.2 Hz, 2H), 7.98 (d, J=7.2 Hz, 2H), 7.81 (d, J=4.8 Hz, 1H), 7.60 (t, J=7.2 Hz, 1H), 7.51 (t, J=7.2 Hz, 1H), 7.45 (t, J=7.2 Hz, 2H), 7.35 (t, J=7.2 Hz, 2H), 6.00 (dd, J=8.6, 23.8 Hz, 1H), 4.91 (m, 1H), 4.77 (dd, J=4.0, 12.4 Hz, 1H), 4.52 (dd, J=4.2, 12.2 Hz, 1H), 2.64 (s, 3H), 2.52 (s, 3H), 1.93 (s, 3H), 1.66 (d, J=22.4 Hz, 3H), MS=627.1 (M+H$^{3o}$).

Compound 38

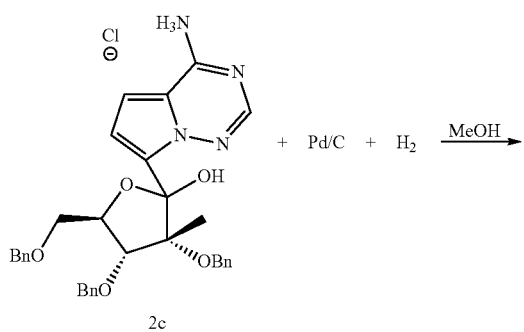

To a 3-neck flask under filled with N$_2$ was added 441 mg (0.2 mmol, 0.25 equiv.) Palladium (10% on C, Degussa type, 50% water content). This was suspended in MeOH (7.5 ml, 15 vol.), and then 500 mg (0.83 mmol, 1 equiv.) 2c-HCl was added. The reaction was placed under light vacuum, then under a Ft, atmosphere. After being stirred vigorously overnight, the reaction was found to be complete. The reaction mixture was filtered through celite, which was then rinsed several times with MeOH. The MeOH was removed under rotary evaporation, and the resulting oil was taken up in EtOAc, giving a white precipitate. This was filtered, providing Compound 38. Yield: 248 mg (90%), (M+H)/Z=297.

Compound 39

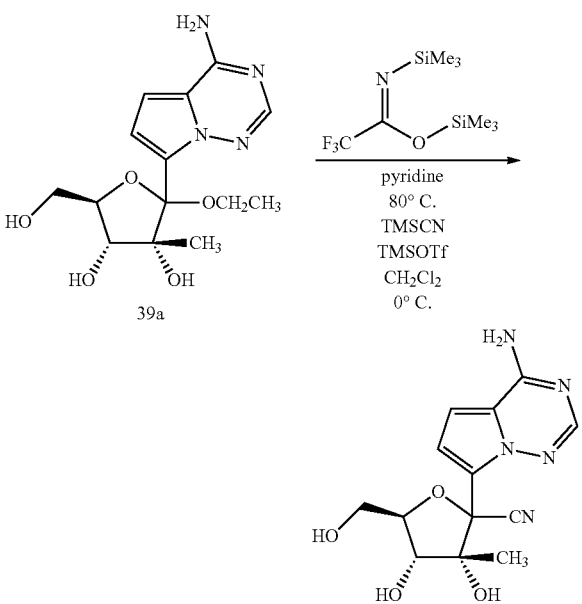

1.0 g of 39a (3.08 mmol) is combined with 10.0 mL pyridine (124.78 mmol) and 4.76 mL (N,O-bis(trimethylsilyl)trifluoroacetamide +1% TMSCl solution; 18.50 mmol, 6.0 equiv.). The mixture is heated to 80° C., and aged for on hour. Following 1.0 h age, the homogeneous yellow solution is cooled to 23° C., and aged with stirring for 18 h. Following aging, to the solution is added 10.0 mL toluene, and the mixture is concentrated by vacuum distillation to an orange oil. The oil is dissolved in 10.0 mL dichloromethane, and the solution is cooled to −10° C. To this cooled solution is added dropwise 2.51 mL TMSOTf (13.88 mmol, 4.5 equiv.) over a period of 30 min. Following TMSOTf addition, the mixture is aged at −5.0 C for 5 min. Following aging, 2.31 mL TMSCN (18.50 mmol, 6.0 equiv.) is added over 8 min. following TMSCN addition, the mixture is warmed to 23° C., and aged with stirring for 2.0 h. Following aging, the mixture is added to a solution of 7.0 g 25 wt % NaOMe/MeOH solution (32.0 mmol, 10.7 equiv.) cooled to 0° C. Following neutralization. the resulting mixture is concentrated to a viscous red oil. This oil is dissolved in 25 mL EtOAc, and to this solution is added 10 mL heptane. The precipitated solids are filtered, and washed with 20 mL EtOAc. The combined rinse and liquors are concentrated and purified by SiO₂ chromatography to afford the desired compound as a mixture of isomers, (M+H)/Z=306.
Compound 40

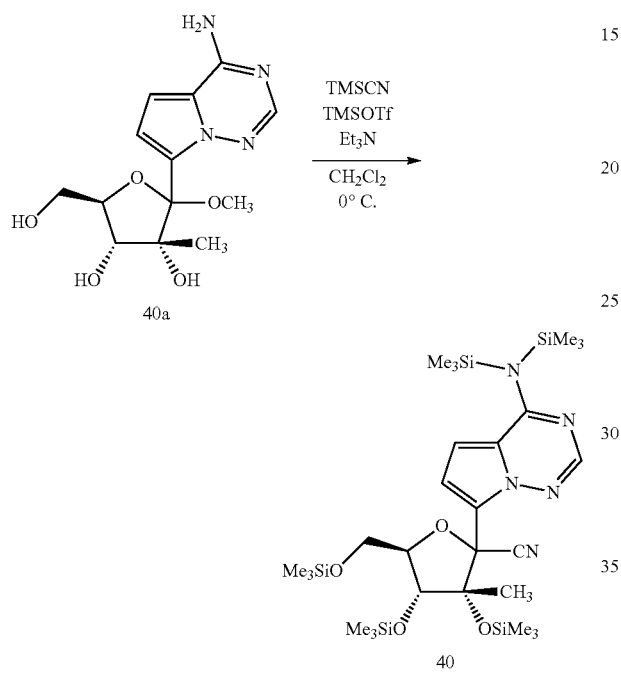

0.10 g 40a (0.232 mmol) is combined with 200.1 mg triethylamine (1.92 mmol, 6.0 equiv.) is suspended in 1.0 mL dichloromethane and this mixture is cooled to −5.0° C. To this heterogeneous suspension is added 470 μL TMSOTf (8.0 equiv.) over a period of 3 minutes with stirring. The mixture is aged @−5.0° C. for 10 minutes with stirring. Following age, to the cooled mixture is added 240 μL TMSCN (6.0 equiv.). The mixture is aged with stirring at 0° C. for an additional 2 h. The desired compound 40 is formed in ~50% by ANHPLC, (M+H)/Z=666.
Compounds 41-45

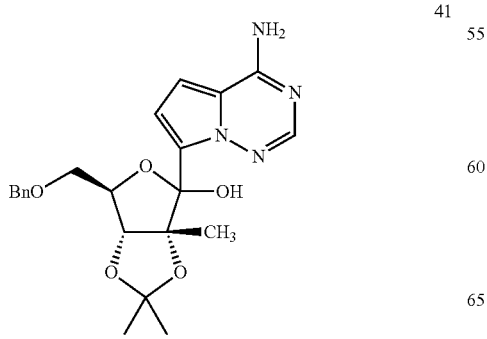

41

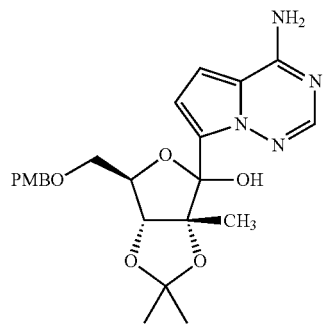

42

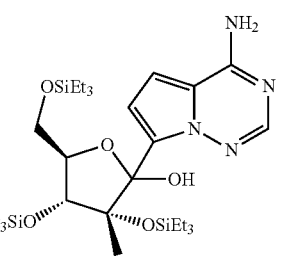

43

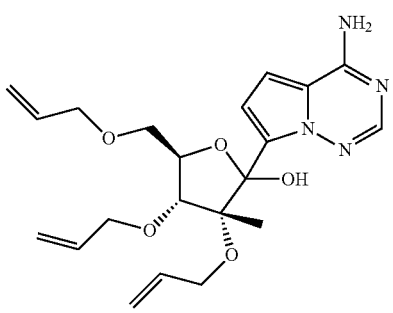

44

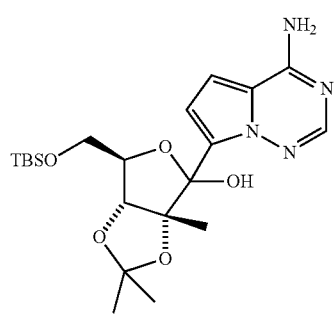

45

Using either Lactone C, D, E, F or H, Compounds 41, 42, 43, 44, or 45, respectively, may be prepared using the procedures described to prepare Compounds 2c or 14.
Compounds 46-51

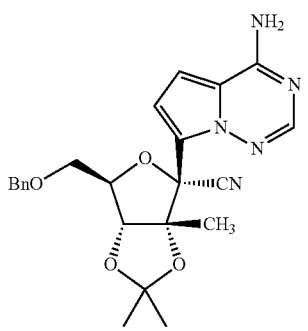

46

-continued

47

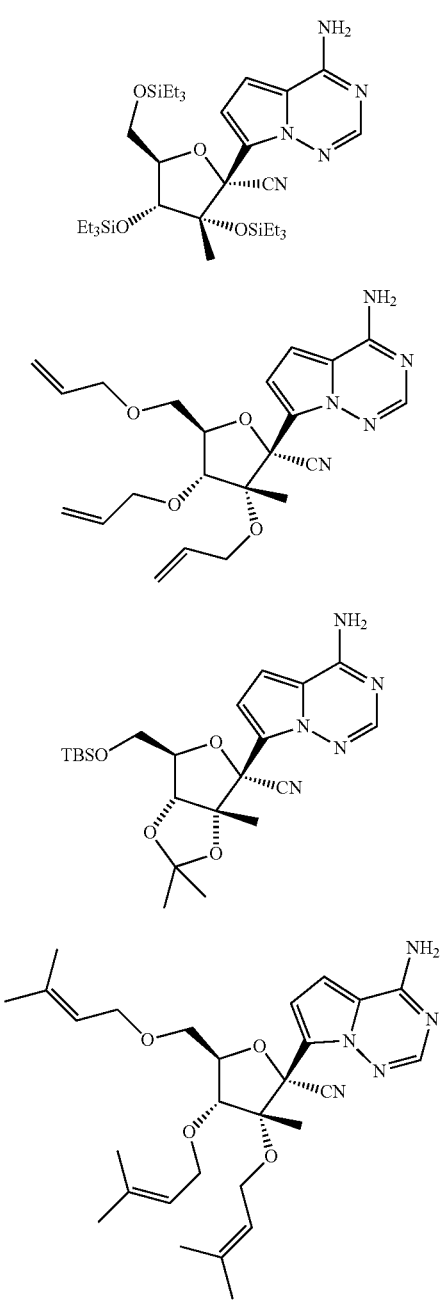

48

49

50

51

Using Compounds 41, 42, 43, 44, 45 or 14, respectively, Compounds 46, 47, 48, 49, 50 or 51, respectively, may be obtained using the cyanation procedures described for the examples disclosed herein.

All publications, patents, and patent applications cited herein above are incorporated by reference herein, as though individually incorporated by reference.

The invention has been described with reference to various specific and preferred embodiments and techniques. However, one skilled in the art will understand that many variations and modifications may be made while remaining within the spirit and scope of the invention.

What is claimed is:

1. A compound of Formula VId:

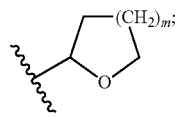

Formula VId or an acceptable salt, thereof;
wherein:
$R^1$ is H, or $(C_1\text{-}C_8)$alkyl;
$R^7$ is $-C(R^5)_2R^6$, $Si(R^3)_3$, or

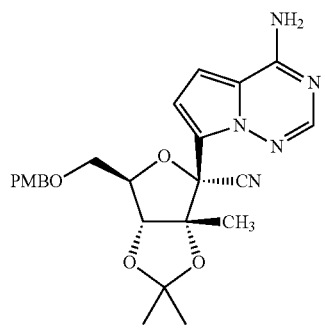

each $R^3$ is independently $(C_1\text{-}C_8)$alkyl, $(C_1\text{-}C_8)$ substituted alkyl, $C_6\text{-}C_{20}$ aryl, $C_6\text{-}C_{20}$ substituted aryl, $C_2\text{-}C_{20}$ heterocyclyl, $C_2\text{-}C_{20}$ substituted heterocyclyl, $C_7\text{-}C_{20}$ arylalkyl, $C_7\text{-}C_{20}$ substituted arylalkyl, $(C_1\text{-}C_8)$alkoxy, or $(C_1\text{-}C_8)$ substituted alkoxy;

each $R^5$ is independently H, $(C_1\text{-}C_8)$alkyl, $(C_1\text{-}C_5)$ substituted alkyl, $(C_2\text{-}C_8)$alkenyl, $(C_2\text{-}C_8)$ substituted alkenyl, $(C_2\text{-}C_8)$alkynyl, $(C_2\text{-}C_8)$ substituted alkynyl, $C_6\text{-}C_{20}$ aryl, $C_6\text{-}C_{20}$ substituted aryl, $C_2\text{-}C_{20}$ heterocyclyl, substituted heterocyclyl, $C_7\text{-}C_{20}$ arylalkyl, or $C_7\text{-}C_{20}$, substituted arylalkyl;

each $R^6$ is independently $C_6\text{-}C_{10}$ aryl, $C_2\text{-}C_{20}$ substituted aryl, or optionally substituted heteroaryl;

each $R^a$ is independently H, $(C_1\text{-}C_8)$alkyl, $(C_2\text{-}C_8)$alkenyl, $(C_2\text{-}C_8)$alkynyl, aryl$(C_1\text{-}C_8)$alkyl, $(C_4\text{-}C_8)$carbocyclylalkyl, $-C(=O)R^{11}$, $-C(=O)OR^{11}$, $-C(=O)NR^{11}R^{12}$, $-C(=O)SR^{11}$, $-S(O)R^{11}$, $-S(O)_2R^{11}$, $-S(O)(OR^{11})$, $-S(O)_2(OR^{11})$, or $-SO_2NR^{11}R^{12}$;

$X^1$ is CH;
each $X^2$ is O or $CH_2$;
each m is 1 or 2;
each n is independently 0, 1 or 2;
each $R^8$ is $NH_2$;
$R^9$ is H;

each $R^{11}$ or $R^{12}$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, optionally substituted aryl, optionally substituted heteroaryl, —C(=O)($C_1$-$C_8$)alkyl, —S(O)$_n$($C_1$-$C_8$)alkyl, aryl($C_1$-$C_8$)alkyl or Si($R^3$)$_3$; or $R^{11}$ and $R^{12}$ taken together are —Si($R^3$)$_2$($X^2$)$_m$Si($R^3$)$_2$—;

$R^{17}$ is OH;

each $R^{19}$ is methyl;

wherein each $(C_1-C_8)$alkyl, $(C_2-C_8)$alkenyl or $(C_2-C_8)$alkynyl of each $R^1$, $R^3$, $R^5$ or $R^6$ is independently, optionally substituted with one or more halo, hydroxy, CN, $N_3$, N($R^a$)$_2$ or OR$^a$, and wherein one or more of the non-terminal carbon atoms of each said $(C_1-C_8)$alkyl is optionally replaced with —O—, —S(O)$_n$— or —NR$^a$—.

2. The compound of claim 1 that is

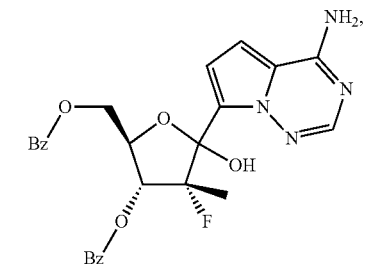

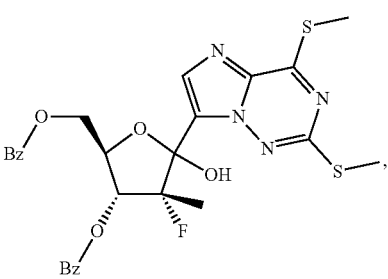

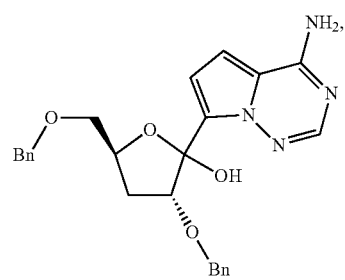

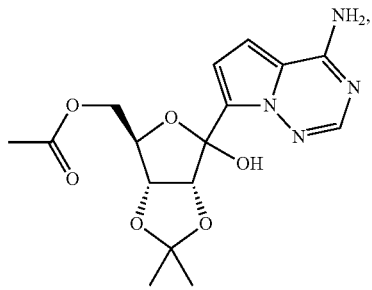

-continued

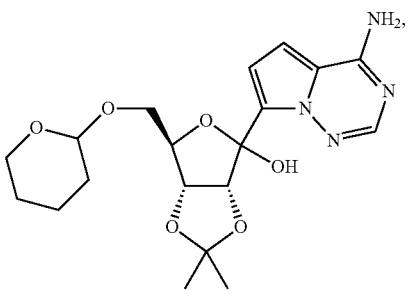

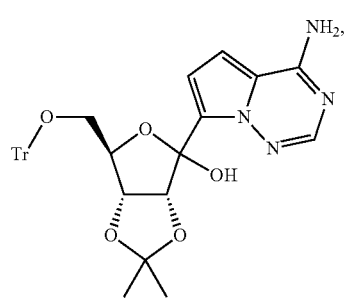

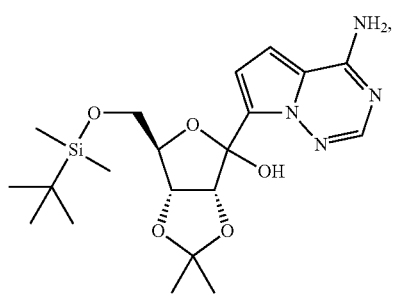

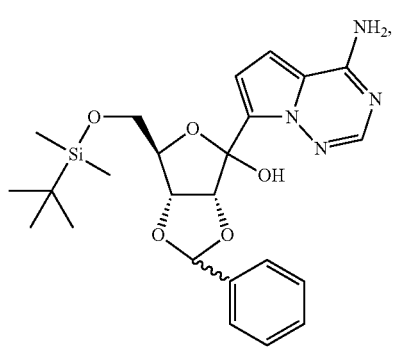

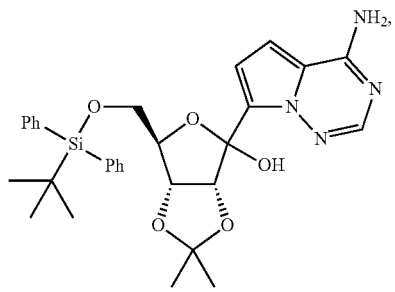

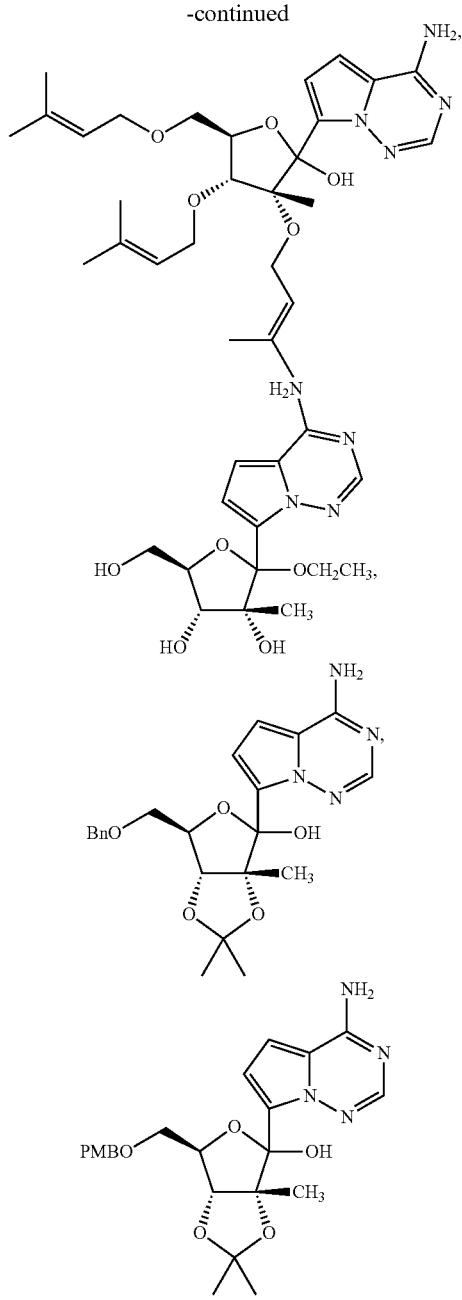
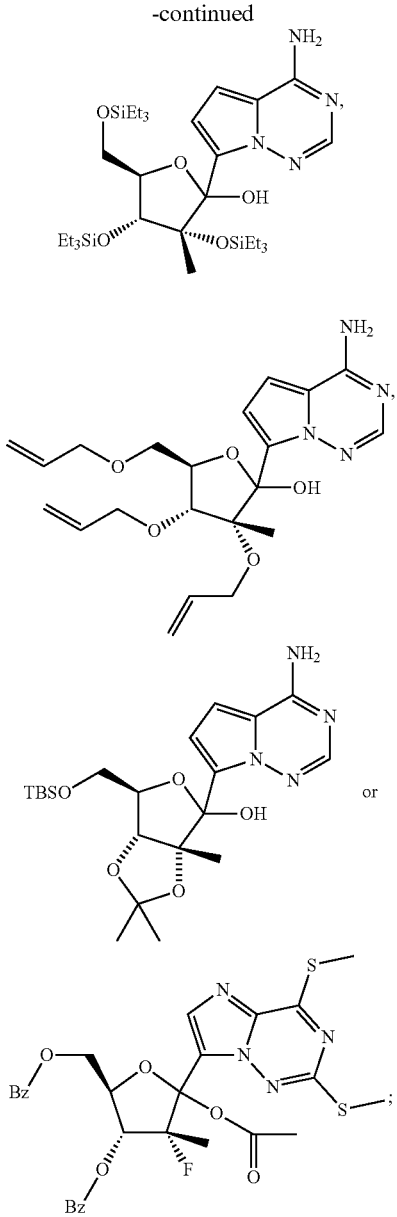
or an acceptable salt thereof.
* * * * *

UNITED STATES PATENT AND TRADEMARK OFFICE
CERTIFICATE OF CORRECTION

PATENT NO. : 10,023,600 B2
APPLICATION NO. : 12/886248
DATED : July 17, 2018
INVENTOR(S) : Thomas Butler et al.

Page 1 of 1

It is certified that error appears in the above-identified patent and that said Letters Patent is hereby corrected as shown below:

In the Claims

Column 81, Line 19, cancel the text beginning with "2. The compound of claim 1 that is" and ending at Column 84, Line 50, "or an acceptable salt thereof.", and insert the following claim:
-- 2. The compound of claim 1 that is

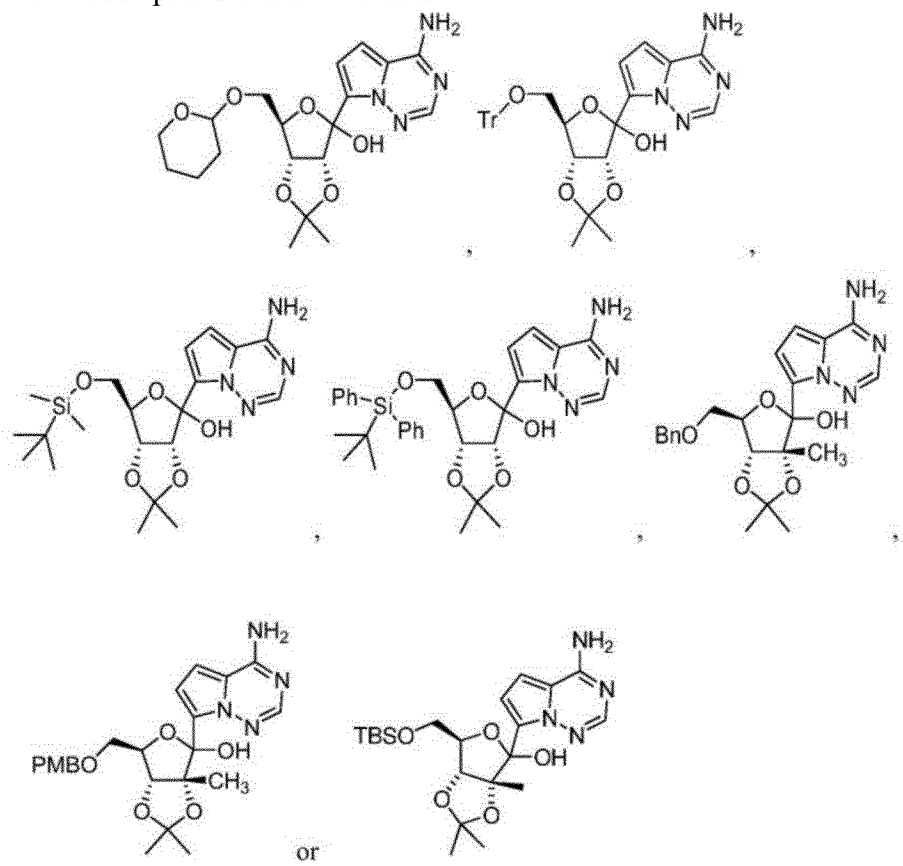

; or an acceptable salt thereof. --

Signed and Sealed this
Fifth Day of March, 2019

Andrei Iancu
*Director of the United States Patent and Trademark Office*